(12) United States Patent
Koral et al.

(10) Patent No.: US 11,793,631 B2
(45) Date of Patent: Oct. 24, 2023

(54) DEVICES FOR ASSISTING WITH HEART VALVE MANUFACTURING

(71) Applicant: Edwards Lifesciences Corporation, Irvine, CA (US)

(72) Inventors: Arthur I. Koral, Tustin, CA (US); James R. Cody, III, Tustin, CA (US); Ping-Yang Shih, Santa Ana, CA (US); Tiffany Diemtrinh Tran, Anaheim, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 17/652,441

(22) Filed: Feb. 24, 2022

(65) Prior Publication Data

US 2022/0183827 A1 Jun. 16, 2022

Related U.S. Application Data

(63) Continuation of application No. 16/842,620, filed on Apr. 7, 2020, now Pat. No. 11,259,917, which is a
(Continued)

(51) Int. Cl.
*A61F 2/24* (2006.01)
*A61B 90/50* (2016.01)
(Continued)

(52) U.S. Cl.
CPC ............ *A61F 2/2415* (2013.01); *A61B 90/50* (2016.02); *B25J 9/1689* (2013.01); *B25J 11/00* (2013.01);
(Continued)

(58) Field of Classification Search
CPC ........ A61F 2/24; A61F 2/2415; A61F 2/2412; A61F 2/2418–2496; A61F 2/403; A61F 2/406; A61F 2/497; A61F 2220/0075; A61F 2220/0025; A61B 90/50; A61B 90/20; A61B 34/25; A61B 2034/2059;
(Continued)

(56) References Cited

U.S. PATENT DOCUMENTS 3,347,190 A 10/1967 Roth
4,205,616 A 6/1980 Sugahara
(Continued)

FOREIGN PATENT DOCUMENTS

CN 103200900 A 7/2013
GB 781465 A 8/1957
(Continued)

*Primary Examiner* — Ismael Izaguirre
(74) *Attorney, Agent, or Firm* — Edwards Lifesciences

(57) ABSTRACT

An assistance system that can be used for prosthetic heart valve manufacturing or suturing procedures includes an automated fixture that can comprise an articulation arm and a target device holder. The target device holder can be positioned and oriented to reduce operator strain during a manufacturing or inspection process. The assistance system includes a user input device enabling the operator to move between positions to assist in such processes. The assistance system can also be trained by capturing sequences of position data corresponding to a manufacturing or inspection process.

20 Claims, 30 Drawing Sheets

Related U.S. Application Data continuation of application No. 15/900,672, filed on Feb. 20, 2018, now Pat. No. 10,624,738.

(60) Provisional application No. 62/462,554, filed on Feb. 23, 2017.

(51) Int. Cl.

| | | |
|---|---|---|
| *B25J 11/00* | (2006.01) | |
| *B25J 13/02* | (2006.01) | |
| *D05B 19/16* | (2006.01) | |
| *B25J 9/16* | (2006.01) | |
| *A61B 90/20* | (2016.01) | |
| *D05B 35/00* | (2006.01) | |
| *D05B 97/08* | (2006.01) | |
| *A61B 34/00* | (2016.01) | |
| *A61B 90/00* | (2016.01) | |
| *A61B 34/20* | (2016.01) | |

(52) U.S. Cl.
CPC .............. *B25J 13/02* (2013.01); *D05B 19/16* (2013.01); *A61B 34/25* (2016.02); *A61B 90/20* (2016.02); *A61B 2034/2059* (2016.02); *A61B 2090/371* (2016.02); *A61F 2220/0075* (2013.01); *D05B 35/00* (2013.01); *D05B 97/08* (2013.01); *D10B 2509/04* (2013.01); *D10B 2509/06* (2013.01); *Y10S 901/02* (2013.01); *Y10S 901/47* (2013.01)

(58) Field of Classification Search
CPC .. A61B 2034/25; A61B 2034/252–256; A61B 2090/371; B25J 9/1689; B25J 11/00; B25J 13/02–06; B25J 13/006–089; D05B 19/16; D05B 19/12; D05B 35/00; D05B 97/08; D10B 2509/04; D10B 2509/06; Y10S 901/00; Y10S 901/02; Y10S 901/46; Y10S 901/47

See application file for complete search history.

(56) References Cited

U.S. PATENT DOCUMENTS

| | | |
|---|---|---|
| 4,275,986 A | 6/1981 | Engelberger et al. |
| 4,692,164 A | 9/1987 | Dzemeshkevich et al. |
| 5,095,833 A | 3/1992 | Darrieux |
| 6,189,747 B1 | 2/2001 | Collingham et al. |
| 6,445,964 B1 | 9/2002 | White et al. |
| 6,453,062 B1 | 9/2002 | MacNutt et al. |
| 7,739,971 B2 | 6/2010 | Chambers et al. |
| 8,276,533 B2 | 10/2012 | Chambers et al. |
| 9,301,835 B2 | 4/2016 | Campbell et al. |
| 9,339,378 B2 | 5/2016 | Quadri et al. |
| 10,119,882 B2 | 11/2018 | Van Nest et al. |
| 10,624,738 B2 * | 4/2020 | Koral ................... D05B 19/16 |
| 11,259,917 B2 * | 3/2022 | Koral ................... A61F 2/2415 |
| 11,306,423 B2 * | 4/2022 | Cody, III ......... A61K 39/39575 |
| 11,471,225 B2 * | 10/2022 | Gorelik ................. A61B 34/70 |
| 2006/0276889 A1 | 12/2006 | Chambers et al. |
| 2008/0035038 A1 | 2/2008 | Ekholm et al. |
| 2011/0185556 A1 | 8/2011 | Hirano et al. |
| 2013/0046373 A1 * | 2/2013 | Cartledge ............... A61F 2/966 |
| | | 623/1.11 |
| 2014/0127660 A1 | 5/2014 | Rappel et al. |
| 2015/0352720 A1 | 12/2015 | Iizuka |
| 2016/0039093 A1 | 2/2016 | Abdallah et al. |
| 2017/0325976 A1 | 11/2017 | Nguyen et al. |

FOREIGN PATENT DOCUMENTS

| | | |
|---|---|---|
| JP | 2014525602 A * | 9/2014 |
| WO | 9530387 A1 | 11/1995 |
| WO | 0182781 A2 | 11/2001 |
| WO | 2008016760 A2 | 2/2008 |
| WO | 2015070249 A1 | 5/2015 |
| WO | 2016084178 A1 | 6/2016 |
| WO | 2019140293 A1 | 7/2019 |

* cited by examiner

FIG. 19
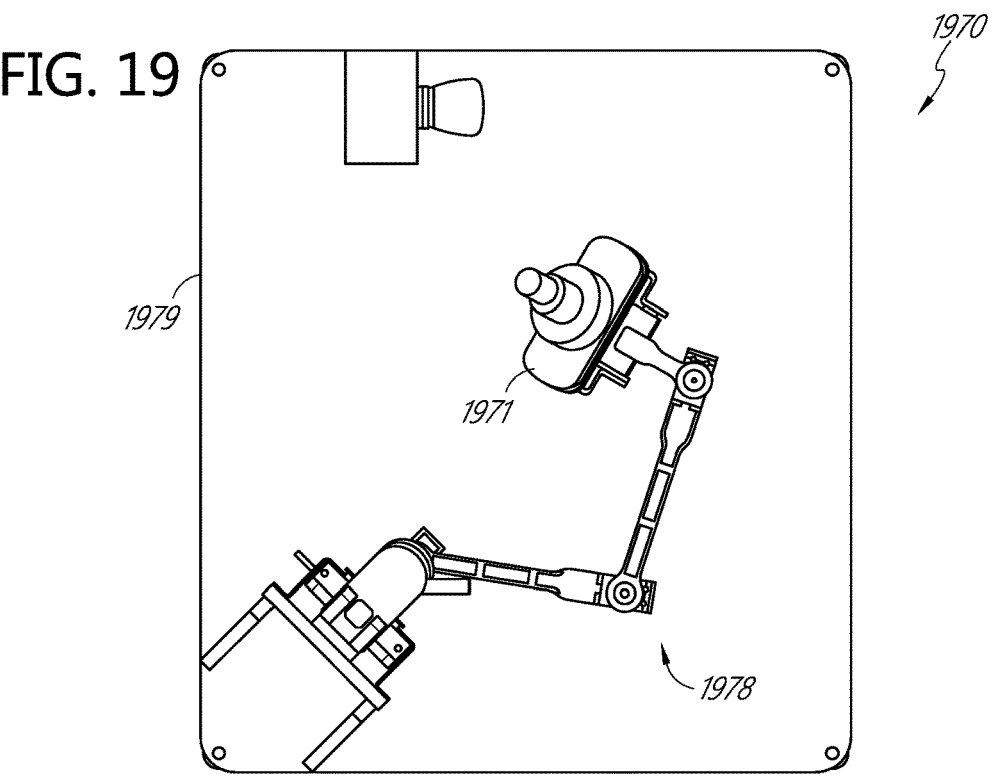
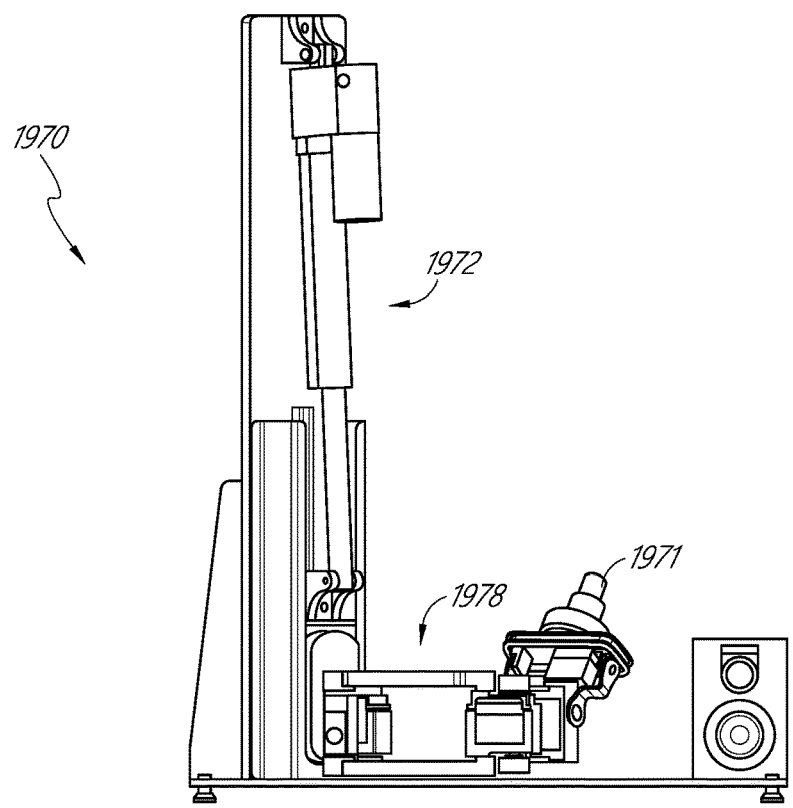
FIG. 20

FIG. 21
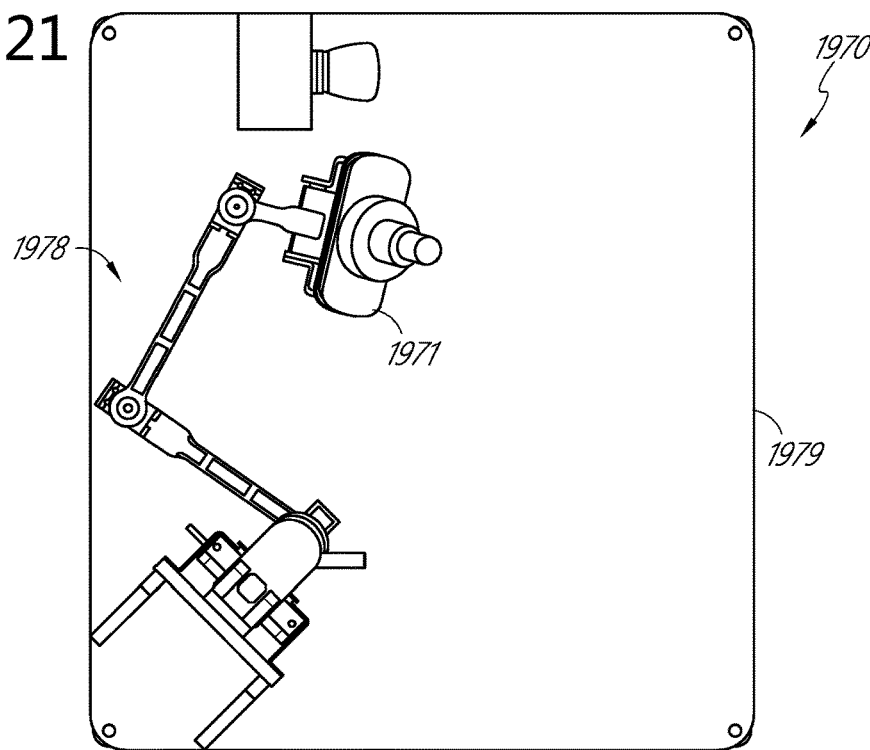
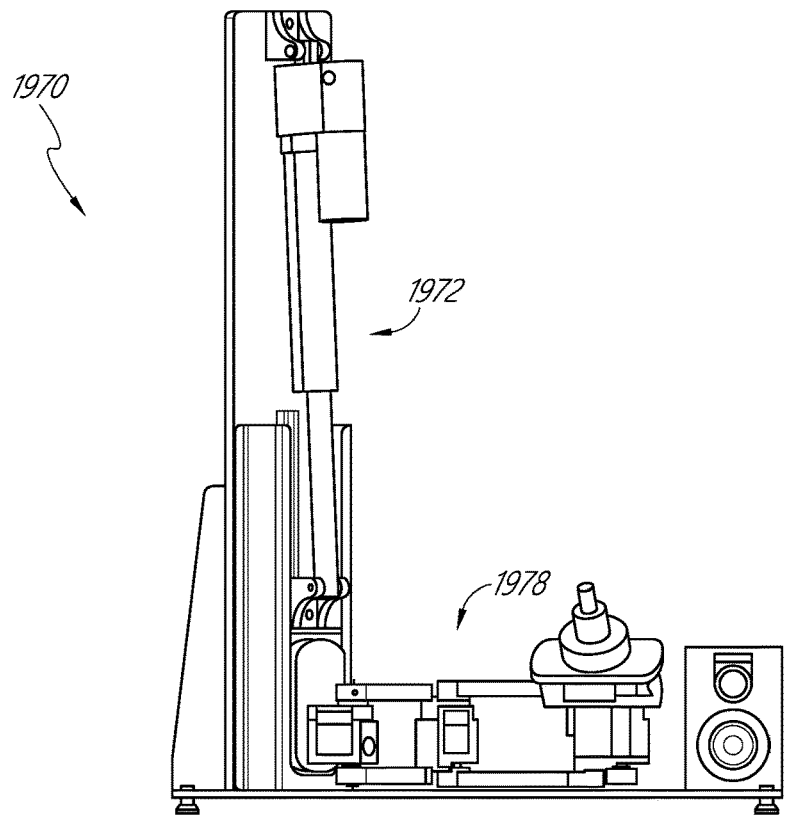
FIG. 22

FIG. 23
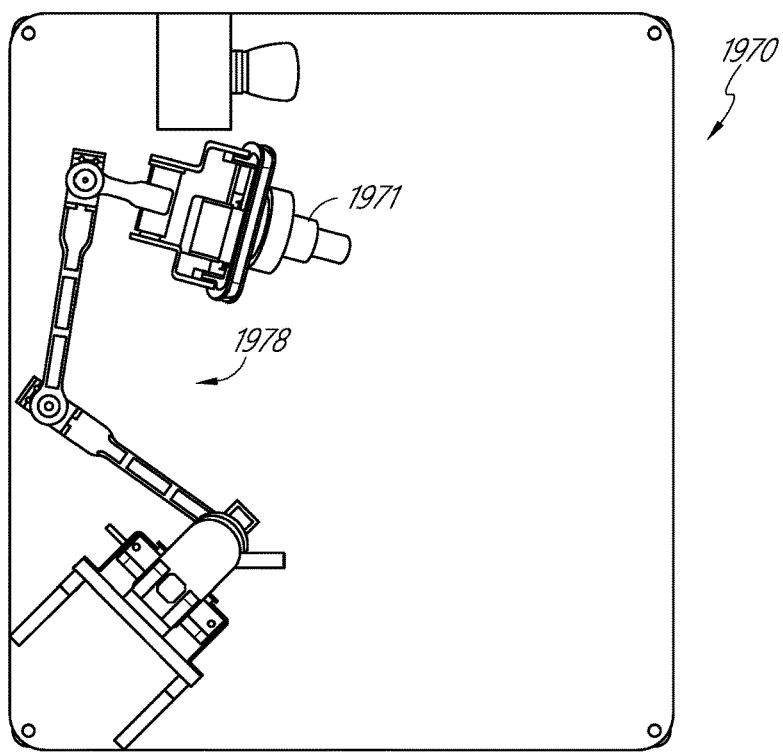
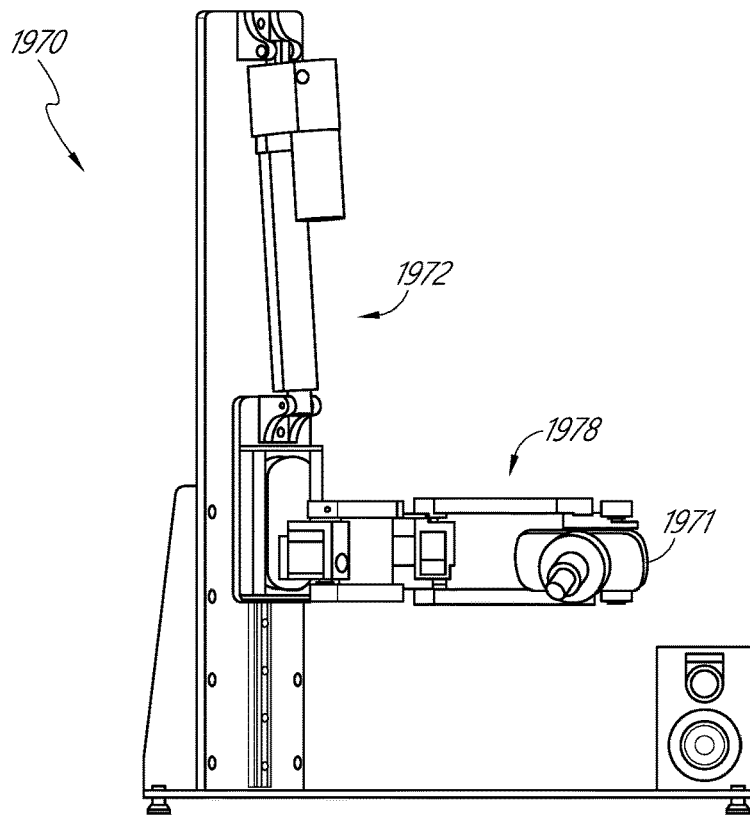
FIG. 24

DEVICES FOR ASSISTING WITH HEART VALVE MANUFACTURING

CROSS-REFERENCE TO RELATED APPLICATIONS

This application is a continuation of U.S. patent application Ser. No. 16/842,620, entitled "DEVICES FOR ASSISTING WITH HEART VALVE MANUFACTURING," filed Apr. 7, 2020, now granted as U.S. Pat. No. 11,259,917, which is a continuation of U.S. patent application Ser. No. 15/900,672, entitled "HEART VALVE MANUFACTURING DEVICES AND METHODS," filed Feb. 20, 2018, now granted as U.S. Pat. No. 10,624,738, which claims the benefit of priority to U.S. Provisional Application No. 62/462,554, entitled "HEART VALVE MANUFACTURING DEVICES AND METHODS," filed Feb. 23, 2017, the entire contents of each of which is expressly incorporated by reference herein for all purposes.

BACKGROUND

Field

The present disclosure generally relates to the field of heart valve manufacturing and associated systems, devices, and methods, including heart valve suturing systems, devices, and methods.

Background

Manufacturing prosthetic heart valves and other human prosthetic implant devices may require suturing, treatment, inspection, etc. of certain portions and/or components thereof. Accuracy and/or efficiency in execution of suturing operations or other operations for such devices can be important. Furthermore, certain heart valve suturing operations or other operations can result in operator strain.

SUMMARY

This summary is meant to provide some examples and is not intended to be limiting of the scope of the invention in any way. For example, any feature included in an example of this summary is not required by the claims, unless the claims explicitly recite the features. Also, the features, steps, concepts, etc. described in examples in this summary and elsewhere in this disclosure can be combined in a variety of ways. The description herein relates to devices, apparatuses, systems, assemblies, methods, combinations, etc. that can be utilized for manufacturing and processing heart valves and/or associated or related components, devices, apparatuses, etc. Among other features, these or elements of these can utilize or include logic that may receive a set of parameters as input. In some embodiments, the set of parameters may be graphically displayed to a user after the parameters have been received as input. In some embodiments, the set of parameters may be analyzed and new data generated. In some embodiments, the newly generated data may be graphically displayed to a user after the parameters have been received as input.

In some implementations, the present disclosure relates to a method of manufacturing a target device or component (e.g., to a method of manufacturing, or suturing, a prosthetic implant device, prosthetic human implant device, prosthetic heart valve, prosthetic human heart valve, etc.). The method can comprise disposing the target device (e.g., prosthetic human implant device, etc.) on a holder component of an automated fixture (e.g., an automated suture fixture). The method can also comprise directing or providing input to cause the automated fixture (e.g., automated suture fixture) to position the target device (e.g., prosthetic human implant device, etc.) in a first position, executing a first operation/procedure (e.g., a stitch, inspection, other operation/procedure) on the target device (e.g., prosthetic human implant device, etc.) using a first hand of the operator, directing or providing input to cause the automated fixture (e.g., automated suture fixture) to position the target device (e.g., prosthetic human implant device, etc.) in a second position, and executing a second operation/procedure (e.g., stitch, inspection, etc.) on the target device (e.g., prosthetic human implant device, etc.) using the first hand of the operator. The target device can be a prosthetic human implant device. The prosthetic human implant device can be a heart valve or other type of implant device.

The step of directing or providing input to cause the automated fixture (e.g., automated suture fixture) to position the target device (e.g., prosthetic human implant device, etc.) in the first position can involve directing or providing input to cause the automated fixture (e.g., automated suture fixture) to move the target device (e.g., prosthetic human implant device) to a desired focal length from a visualization or imaging system (e.g., a camera lens of an imaging system/camera, etc.). The method can also comprise directing or providing input to cause the automated fixture (e.g., automated suture fixture) to move or rotate (e.g., rotate; circumferentially rotate; flip; rotate with respect to an axis, such as an axis that passes through a center point of the device; etc.) the target device (e.g., prosthetic human implant device, etc.) in place, while maintaining at least some portion of an outer surface of the prosthetic human implant device in focus of a visualization or imaging system (e.g., a camera, etc.). This can be done with or without moving the visualization system (e.g., without moving a camera or camera lens). Operation of the automated fixture (e.g., automated suture fixture) can provide for reduced physical strain on the operator, e.g., it can replicate and/or remove the need for the operator to bend, twist, turn, etc. one hand to move the target device into place for an operation/procedure (e.g., for suturing, etc.).

The method can further comprise loading a procedure script (e.g., a pre-programmed suturing procedure script, suturing script, inspection script, other procedure script, etc.) using one or more processors configured to at least partially control the automated fixture (e.g., automated suture fixture). The method can comprise performing a pre-punch on the target device (e.g., prosthetic human implant device, etc.) using a handheld tool operated by a second hand of the operator, e.g., if the automated fixture replaces the need to use one hand both hands of the operator can be available, such as one for suturing and one for another operation. The target device (e.g., prosthetic human implant device, etc.) can comprise an outside surface and an inside surface defining an at least partially open inside cylinder cavity. The first operation/procedure can be a first stitch, and the first stitch can be an outside-to-inside stitch executed by puncturing a needle through the outside surface to the inside cylinder cavity. The second operation/procedure can be a second stitch, and the second stitch can be an inside-to-outside stitch executed by puncturing the inside surface. For example, the first position can present the outside surface (e.g., a portion of the outside surface) to the operator and the second position can present the inside surface (e.g., a portion of the inside surface) to the operator.

The method(s) described herein may include steps for and/or be part of a method for training a suture assistance system. The method can comprise manipulating a position of the/an automated fixture (e.g., automated suture fixture) to a first desired position, storing first data that indicates the first desired position, manipulating the position of the automated fixture (e.g., automated suture fixture) to a second desired position, and storing second data that indicates the second desired position, wherein the second data is stored in association with the first data (e.g., the first data and the second data can be associated with each other as part of a common procedure script, for example, representing different positions for different steps of a common procedure). The method can further comprise generating the first data at least in part by capturing position information indicative of the first desired position when the automated fixture (e.g., automated suture fixture) is in the first desired position, and generating the second data at least in part by capturing position information indicative of the second desired position when the automated fixture (e.g., automated suture fixture) is in the second desired position.

Manipulating the position of the automated fixture (e.g., automated suture fixture) can involve manually manipulating the automated suture fixture, manually manipulating an arm component of the automated suture fixture, and/or inputting positioning information using a user input device. For example, user input device(s) that can be used include a joystick device, pedal(s), button(s), electronic input(s), touchscreen control, other input device or mechanisms, or a combination of input devices and/or mechanisms. The method can further comprise, after said manipulating the position of the automated fixture (e.g., automated suture fixture) to the first desired position, providing user input to trigger said storing the first data. For example, the user input can involve pressing a foot pedal, button, electronic input, touchscreen control, etc.

The method can further comprise focusing a camera on a target device (e.g. a suture target device, prosthetic implant device, heart valve, etc.) held by the automated fixture (e.g., automated suture fixture) when the automated fixture (e.g., automated suture fixture) is in the first desired position, wherein the first data indicates a focus setting of the camera. The camera can be configured to remain focused on the suture target device when the automated fixture (e.g., automated suture fixture) is in the second position without adjustment of the camera's position or focus. In certain embodiments, the method further comprises positioning a camera to a first position when the automated fixture (e.g., automated suture fixture) is in the first desired position, and positioning the camera to a second position when the automated fixture (e.g., automated suture fixture) is in the second desired position, wherein the first data indicates the first position of the camera and the second data indicates the second position of the camera.

The disclosed methods can include using an assistance system (e.g., a manufacturing assistance system, a suturing assistance system, inspection assistance system, etc.).

An assistance system (e.g., a suturing assistance system, etc.) can comprise an automated fixture (e.g., automated suture fixture) comprising a plurality of motorized actuator devices and a holder (e.g., a target holder, suture target holder, holder assembly, holder device, holder component, etc.). The automated fixture (e.g., automated suture fixture) can be configured to rotate a target device (e.g., a target suture device, implant, heart valve, prosthetic human implant, etc.) connected to, mounted to, or otherwise supported by the holder. The assistance system (e.g., suturing assistance system, etc.) can include a visualization or imaging system (e.g., a camera system, etc.) configured to generate an enlarged image of the target device (e.g., target suture device, etc.) and a display, monitor, or screen (e.g., a suture target display) configured to display or show the enlarged image. The display (e.g., suture target display) can indicate a target position (e.g., a target suture position, target inspection position, target operation position, etc.) associated with the target device (e.g., target suture device, etc.). The target device (e.g., target suture device) can be a heart valve, implant, prosthetic human implant, etc., and/or a component thereof.

The assistance system (e.g., suturing assistance system, etc.) can further comprise a controller configured to direct the visualization system (e.g., camera system) to capture image data associated with a procedure (e.g., a suturing procedure, inspection procedure, other procedure, etc.) and store the image data. The image data can be stored with metadata identifying at least one of the suturing procedure and an operator associated with the suturing procedure, as well as other information.

The automated fixture (e.g., automated suture fixture) can be configured to adjust a tension of the automated fixture (e.g., automated suture fixture). The automated fixture (e.g., automated suture fixture) can include a pressure plate component configured to adjust the tension of the automated fixture (e.g., automated suture fixture).

The display (e.g., suture target display) can comprise a reticle. For example, the reticle can comprise a circular reticle, which can include notches for stitch counting, and/or a ruler. The display (e.g., suture target display) can be configured to display or show instructions (e.g., suturing instructions, step instruction, procedure instructions, etc.) in connection with a procedure (e.g., suturing procedure, inspection procedure, other procedure, etc.). The assistance system (e.g., suturing assistance system) can provide for reduced physical strain on an operator thereof compared to dual-hand or two-handed procedures (e.g., dual-hand or two-handed suturing procedures, etc.). The holder (e.g., target suture device holder, etc.) can be a gimbal holder assembly. For example, the gimbal holder assembly can comprise a three-axis gimbal.

The automated fixture (e.g., automated suture fixture) can be configured to move the target device (e.g., target suture device, etc.) in at least four directions. The automated fixture (e.g., automated suture fixture) can comprise a plurality of servo motor devices daisy-chained together. The plurality of servo motor devices can be configured to be mounted horizontally, vertically, or at another angle relative to the ground and/or other servo motor devices. The visualization system (e.g., the camera system) can comprise a first camera and a second camera, the first and second cameras collectively configured to provide images of two different views of the target device (e.g., target suture device) or two different views showing different portions of the target device. The automated fixture (e.g., automated suture fixture) can comprise an encoder associated with an articulation arm, the encoder configured to provide position information for the articulation arm.

The/an automated fixture (e.g., automated suture fixture) can comprise a plurality of actuator devices (e.g., motorized actuator devices). Each of the actuator devices (e.g., motorized actuator devices) can comprise a motor and a rotating support member coupled to a rotor component of the motor. A holder assembly or holder (e.g., a suture target holder assembly, etc.) can be attached to the rotating support member of a distal actuator device of the plurality of actuator devices (e.g., motorized actuator devices) and can be configured to hold a target device (e.g., a prosthetic heart valve device, implant device, etc.). Each of the plurality of actuator devices (e.g., motorized actuator devices) can be fixed to one or more other actuator devices of the plurality of actuator devices (e.g., plurality of motorized actuator devices). Furthermore, the automated fixture (e.g., automated suture fixture) can be configured to receive control signals and to rotate the rotating support members of one or more of the plurality of actuator devices (e.g., motorized actuator devices) based on the control signals.

Each of the plurality of actuator devices (e.g., motorized actuator devices) can further comprise a servo feedback component configured to generate a signal indicating a position of a respective rotor component. The servo feedback component can be a digital encoder. The plurality of actuator devices (e.g., motorized actuator devices) can comprise one or more base actuator devices and at least one intermediate-stage actuator device fixed at a base thereof to the rotating support members of the one or more base actuator devices, wherein the distal actuator device can be fixed at a base thereof to the rotating support member of the intermediate-stage actuator device. The base of the intermediate-stage actuator device can be fixed to the rotating support members of the one or more base actuator devices via a connector plate mounted to the rotating support members of the one or more base actuator devices. The rotating support members of the one or more base actuator devices can be fixed to one another. The one or more base actuator devices can consist of one motorized actuator device, or two motorized actuator devices, or more motorized actuator devices. The holder assembly or holder (e.g., suture target holder assembly) can comprise one or more components configured to rotate about an axis substantially orthogonal to an axis of rotation of the rotating support member of the distal actuator device. The holder assembly or holder (e.g., suture target holder assembly) can comprise one or more components configured to rotate about an axis substantially parallel to an axis of rotation of the rotating support member of the distal actuator device.

The/an assistance system (e.g., suturing assistance system, manufacturing assistance system, inspection assistance system, other procedure assistance system, etc.) can comprise an automated fixture (e.g., automated suture fixture) comprising a plurality of actuator devices (e.g., motorized actuator devices) and a holder (e.g., a suture target holder, etc.). The automated fixture (e.g., automated suture fixture) can be configured to position a target device (e.g., target suture device, implant, heart valve, etc.) mounted to the holder. The assistance system and/or automated fixture can include a data store (e.g., memory, database, etc.) storing procedure script data (e.g., suturing procedure script data, inspection script data, manufacturing script data, other procedure script data, etc.). The procedure script data (e.g., suturing procedure script data, etc.) can include a data set representing a plurality of positions of the automated fixture (e.g., automated suture fixture) for a procedure (e.g., for a suturing procedure, inspection procedure, manufacturing procedure, other procedure, etc.). The assistance system and/or automated fixture can include a controller configured to access the procedure script data (e.g., suturing procedure script data, etc.) and provide position control signals to the automated fixture (e.g., automated suture fixture) based at least in part on the procedure script data (e.g., suturing procedure script data, etc.). The target device (e.g., target suture device) can be a prosthetic human heart valve implant device, etc.

The controller can be further configured to select the data set from among a plurality of data sets of the procedure script data (e.g., suturing procedure script data). For example, the selecting can be based at least in part on operator profile information and/or user input received by the controller. Optionally, an operator profile can be applied to or combined with procedure script data to generate individualized procedure script data particular to the preference and/or characteristics of the operator. The plurality of data sets can include a first data set corresponding to a right-handed execution of the suturing procedure and a second data set corresponding to a left-handed execution of the suturing procedure.

Other steps, features, components, etc. not specifically mentioned in these examples, but described elsewhere herein or otherwise known can also be included and/or used with the examples described here.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 18, 19, 20, 21, 22, 23, 24, and 25 illustrate views of a snake-like configuration of an automated fixture in accordance with one or more embodiments.

DETAILED DESCRIPTION

Figure 1:
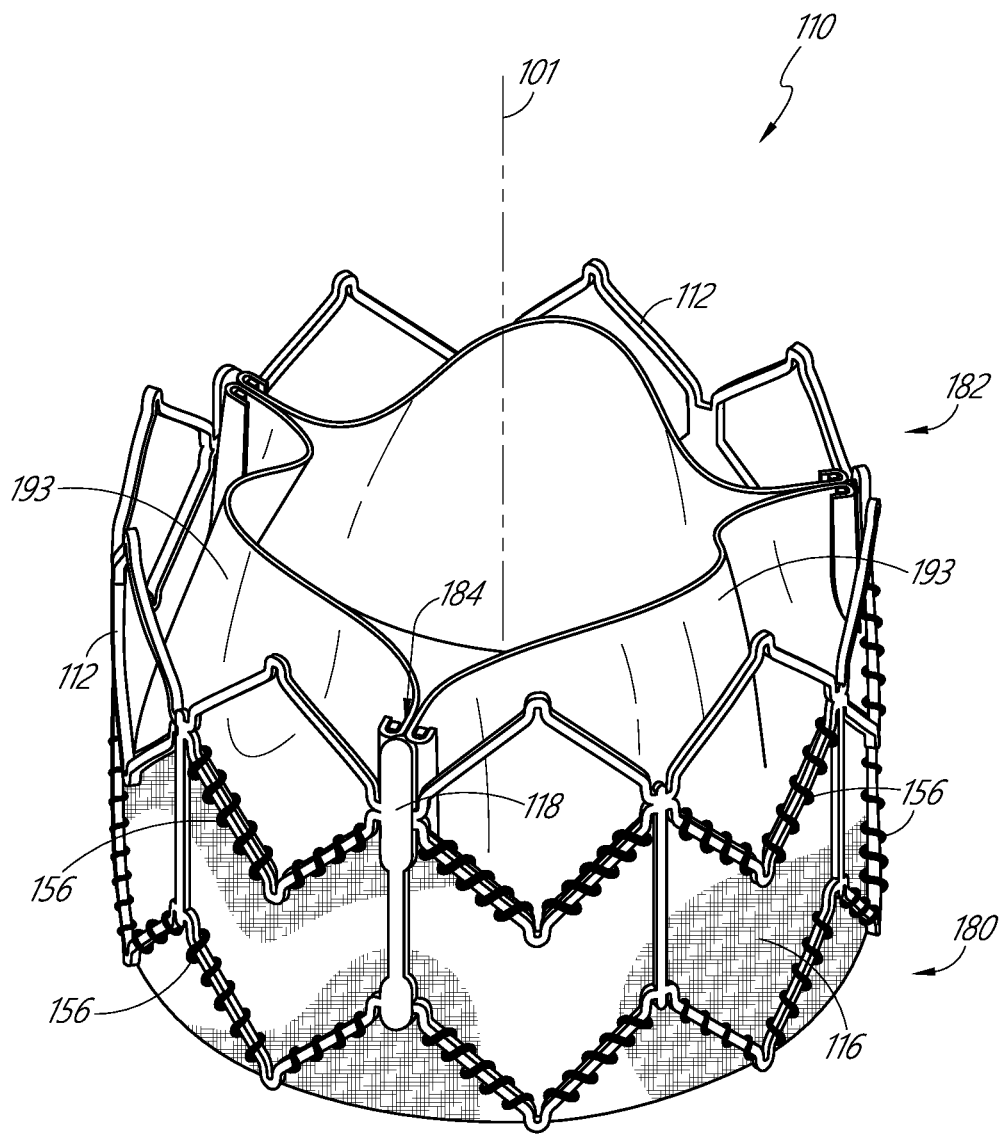
FIG. 1 illustrates an implantable prosthetic valve device according to one or more embodiments.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Further, one or more steps disclosed with respect to one method may be incorporated into other methods disclosed herein. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. Features described with respect to one exemplary embodiment may be incorporated into other embodiments disclosed herein even if not specifically described with respect to the embodiment.

Overview

Prosthetic heart valve implants, as well as many other types of prosthetic implant devices and other types of devices, can include various sutured components and/or portions. For example, a sealing portion, skirt, etc. can be sutured to a frame of a prosthetic heart valve to help prevent blood from leaking around the outer edges or circumference of the prosthetic heart valve. Execution of sutures by a human operator may be relatively difficult and/or cumbersome in certain conditions. For example, where small stitches are to be made with high precision, the complexity and/or associated operator burden may result in injury and/or undesirably low quality of products. Furthermore, certain heart valve implant devices may require upward of a thousand sutures, which can involve substantially labor-intensive and error-susceptible suturing procedures. Therefore, collaborative suturing aids can be desirable to improve quality and/or to reduce operator strain.

Certain embodiments disclosed herein provide collaborative heart valve suturing systems, devices, and/or methods for providing suturing assistance for point-by-point suturing procedures based on the physical manipulation and/or positioning of one or more automated mechanical articulating fixtures, components, and/or subassemblies. Such articulating fixture(s) or component(s) may be configured to hold or secure a prosthetic human heart valve implant device or other suturing subject or implant device having one or more components or portions that may advantageously be sutured together. Suture assistance systems, devices, and/or processes in accordance with the present disclosure may implement a focused visual display system configured to provide visual aids for stitch targeting, operator instruction communication, or the like. The various embodiments relating to heart valve suturing presented herein can be applicable to heart valves having any type of suturing and/or structural configuration or pattern. Examples of heart valve structures and heart valve suturing techniques that may be applicable to certain embodiments presented herein are disclosed in WIPO Publication No. WO 2015/070249, the entire contents of which is hereby expressly incorporated by reference for all purposes.

FIG. 1 illustrates an implantable prosthetic human valve device 110 according to one or more embodiments. The features of valve 110 described herein can apply to other valves, including other valves described elsewhere herein. The valve 110 can be, for example, a transcatheter heart valve (THV), balloon-expandable heart valve, and/or mechanically-expandable heart valve. The valve 110 in the illustrated embodiment can generally comprise a frame, or stent, 112, a leaflet structure 193 supported by the frame 112, and a sealing member or skirt 116 secured (e.g., sutured) to the outer surface of the leaflet structure 193. In certain embodiments, the valve 110 may be configured to be implanted in the annulus of a native heart valve of a human, such as an aortic valve. However, the valve 110 can additionally or alternatively be adapted to be implanted in other native valves of the heart, or in various other vasculature, ducts, or orifices of the body, or in grafts, docking stents, docking stations, rings, etc. implanted in the body. The lower end 180, according to the illustrated orientation, of the valve 110 may represent an inflow end, while the upper end 182, according to the illustrated orientation, of the valve 110 may represent an outflow end.

The valve 110 and the frame 112 may be configured to be radially collapsible to a collapsed or crimped state/configuration for introduction into the body using a delivery catheter, and further may be configured to be radially expandable to an expanded state/configuration for implanting the valve at a desired location in the body (e.g., the native aortic valve). In certain embodiments, the frame 112 may comprise a plastic, polymer, shape memory material, or metal expandable material that permits crimping of the valve 110 to a smaller profile for delivery and expansion of the valve. In one embodiment, an expansion device, such as the balloon of a balloon catheter or a tool for mechanical expansion, may be used to expand or help expand the valve. In certain embodiments, the valve 110 may be a self-expanding valve, wherein the frame is made of a self-expanding material such as a shape memory material or metal (e.g., Nitinol). Self-expanding valves may be able to be crimped to a smaller profile and held in the crimped state with a restraining device, such as a sheath covering the valve. When the valve is positioned at or near the target site, the restraining device may be removed or retracted to allow the valve to self-expand to its expanded, functional size or to a deployed configuration.

The sealing portion or skirt 116 may comprise a single piece or multiple pieces or material (e.g., cloth, polymer, etc.) with opposite ends that are secured to each other to form the annular shape shown in FIG. 1 or extend around a circumference of the valve. In certain embodiments, the upper edge of the sealing portion or skirt 116 can have an undulating shape that generally follows the shape of struts of the frame 112. In this manner, the upper edge portions of the sealing portion or skirt 116 can be tightly secured to respective struts with sutures 156. The sealing portion or skirt 116 may be placed on the outside of the frame 112 or on the inside of the frame 112 (as shown) and an upper edge portion of the sealing portion or skirt 116 may be wrapped around the upper surfaces of the frame struts and secured in place with sutures. The sutures 156 may serve to provide a durable attachment of the sealing portion or skirt 116 to the frame 112.

The leaflet structure 193 can comprise three leaflets (as shown in FIG. 1) in certain embodiments, which can be arranged to collapse in a tricuspid arrangement. Although a three-leaflet embodiment is illustrated, it should be understood that valve implants sutured according to embodiments disclosed herein may have any number of leaflets, such as, for example, two or four. The leaflets 193 may be formed from separate flaps of material or tissue, such as, for example, xenograft tissue (e.g., bovine pericardium), or all three leaflets can be derived from a single xenograft valve (e.g., a porcine valve). The lower edge of leaflet structure 193 may have a variety of shapes. In certain embodiments, the lower edge of the leaflet structure 193 may have an undulating, curved, and/or scalloped shape that may be sutured to the frame 112. The leaflets 193 can be secured to one another at their adjacent sides to form commissures 184 of the leaflet structure, where the edges of the leaflets come together. The leaflet structure 193 can be secured to the frame 112 using any suitable techniques and/or mechanisms. For example, the commissures 184 of the leaflet structure may be aligned with the support posts 118 and secured thereto, e.g., using sutures, adhesive, clamping portions, crimping, and/or other attachment means. In one embodiment, the point of attachment of the leaflets 193 to the posts 118 can be reinforced, e.g., with bars comprising a relatively rigid material, such as stainless steel.

Figure 2:
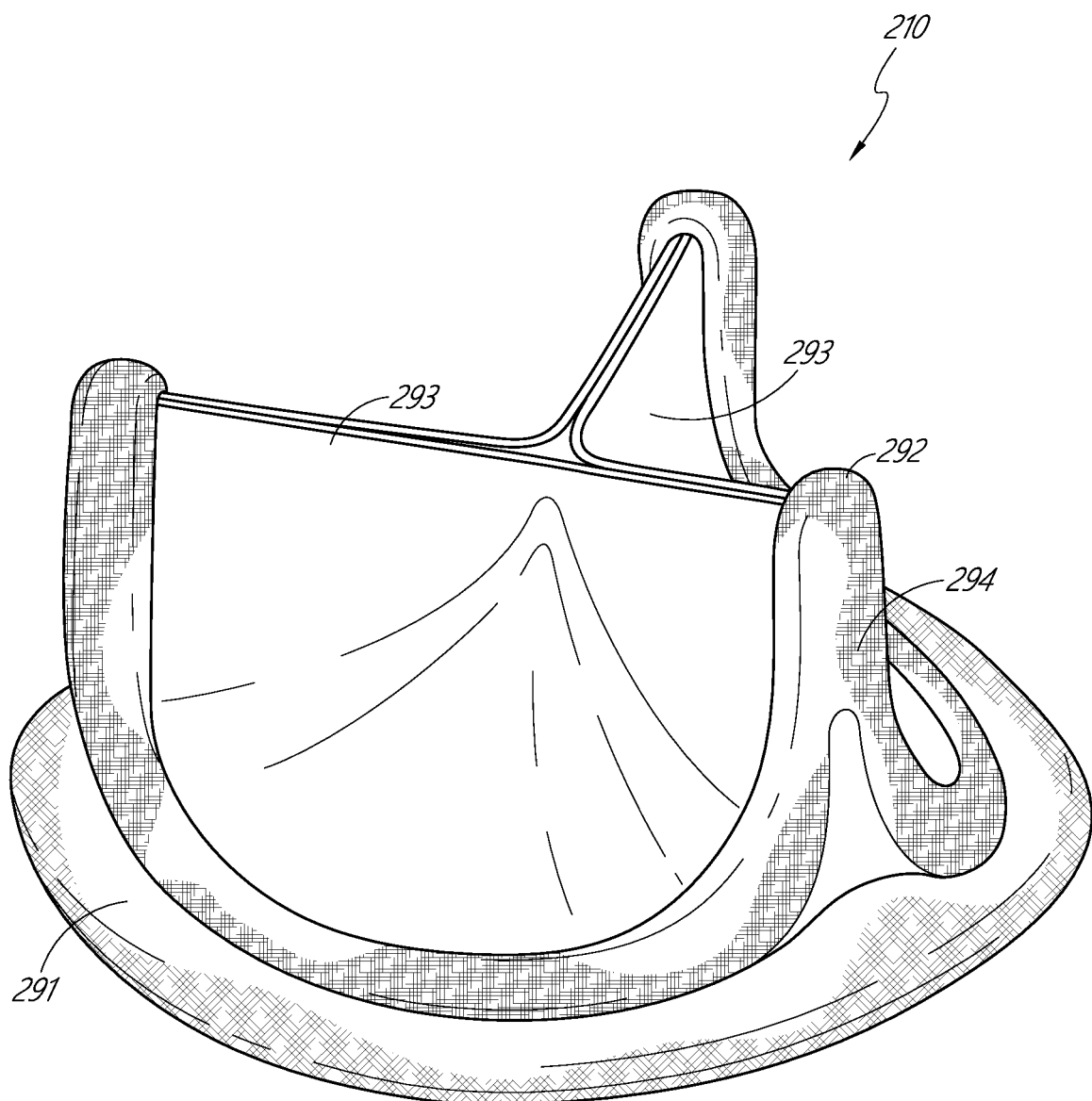
FIG. 2 illustrates a perspective view of a prosthetic heart valve in accordance with one or more embodiments.

FIG. 2 is a perspective view of a prosthetic human heart valve 210 in accordance with one or more embodiments. The heart valve 210 may include a peripheral sealing ring structure 291 configured to provide support for nesting the heart valve 210 in a heart valve cavity and/or resting upon, or attached to, an annulus or other structure of the heart. The valve 210 can further include a frame member 292, such as a metal frame, which may provide support for a plurality of flexible leaflets 293 and can define three upstanding commissure posts 294, wherein the leaflets 293 can be supported between the commissure posts 294. In one embodiment, as shown in FIG. 2, the sealing ring 291 can attach around the periphery of the frame member 294 at the inflow end of the valve 210, with the commissure posts 294 projecting in the outflow direction.

The leaflets 293 may be formed from separate flaps of material or tissue, such as, for example, xenograft tissue (e.g., bovine pericardium), or all three leaflets can be derived from a single xenograft valve (e.g., a porcine valve). The leaflets 293 can be secured and supported both by the commissure posts 294, as well as along arcuate cusps of the frame member between the commissure posts.

Figure 3A:
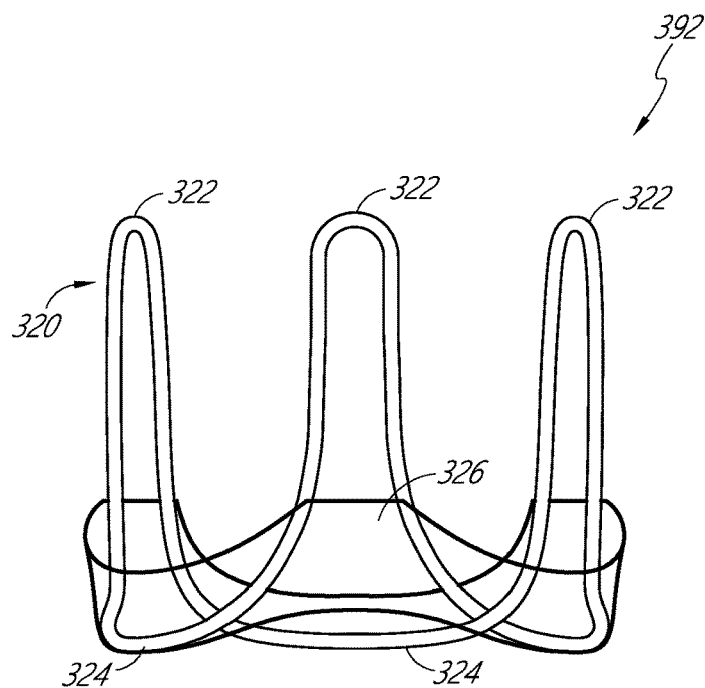
FIG. 3A illustrates a frame for a support stent for a surgical valve in accordance with one or more embodiments.

FIG. 3A shows a frame 392 for a support stent for a surgical heart valve such as the valve 210 of FIG. 2. The frame 392 can include multiple cusps curved toward an axial inflow end alternating with multiple commissures 322 projecting toward an axial outflow end, the support stent 392 defining an undulating outflow edge. The support stent 392 can comprise a wireform 320 having three upstanding commissures 322 alternating with three cusps 324 which generally circumscribe a circumference. A stiffening band 326 may be disposed within or without the wireform 320. The inflow edge of the band 326 can conform or at least partially conform to the cusps 324 of the wireform 320 and may be curved in the outflow direction in between in the region of the wireform commissures 322, e.g., as shown in FIG. 3A. In certain embodiments, the support stent 392 provides the supporting structure of a one-way prosthetic heart valve like the valve 210 of FIG. 2.

Figure 3B:
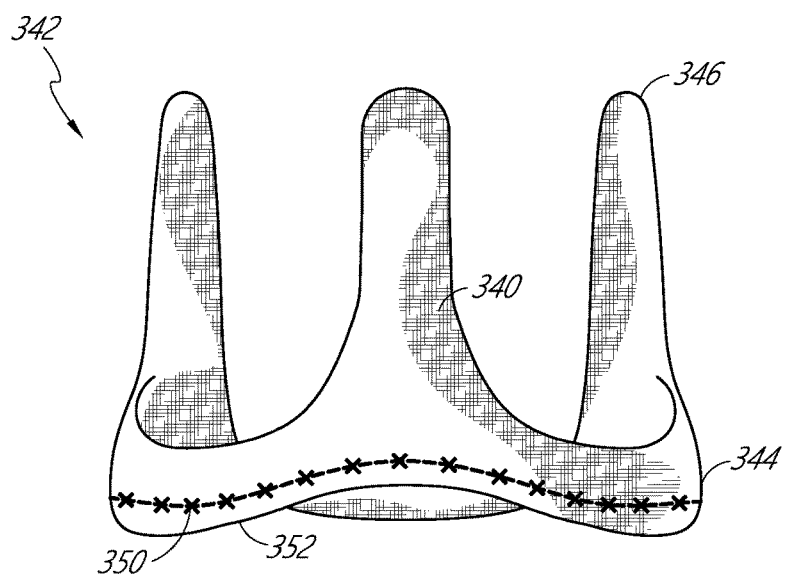
FIG. 3B illustrates the frame of FIG. 3A covered with fabric according to one or more embodiments.

FIG. 3B illustrates the frame of FIG. 3A covered with fabric 340, wherein the fabric 340 may be sutured in one or more portions to secure the fabric 340 as a covering for the frame 392. The fabric-covered support stent 342 may be generally tubular and may include multiple cusps 344 curved toward an axial inflow end alternating with multiple commissures 346 projecting toward an axial outflow end. The support stent 342 may comprise an undulating outflow edge about which the fabric 340 is secured held. In certain embodiments, a seam 350 may be sutured adjacent an inflow edge 352 that secures the fabric 340 about the support stent. The seam 350 is shown slightly axially above the inflow edge 352 for clarity, although it may be located directly at the inflow edge or even inside the support stent. In one embodiment, one or more seams may be located in other positions along the fabric. The sutures of the support stent 342 may be executed or added in multiple ways. Furthermore, although certain stitches are illustrated in FIG. 3B, the support stent 342 and/or valve implant 210 of FIG. 2 can comprise any type or number of stitches or sutures. For example, the support stent 342 and/or one or more other components of the associated implant device, can also have leaflets and/or other materials sutured thereto.

Figure 4:
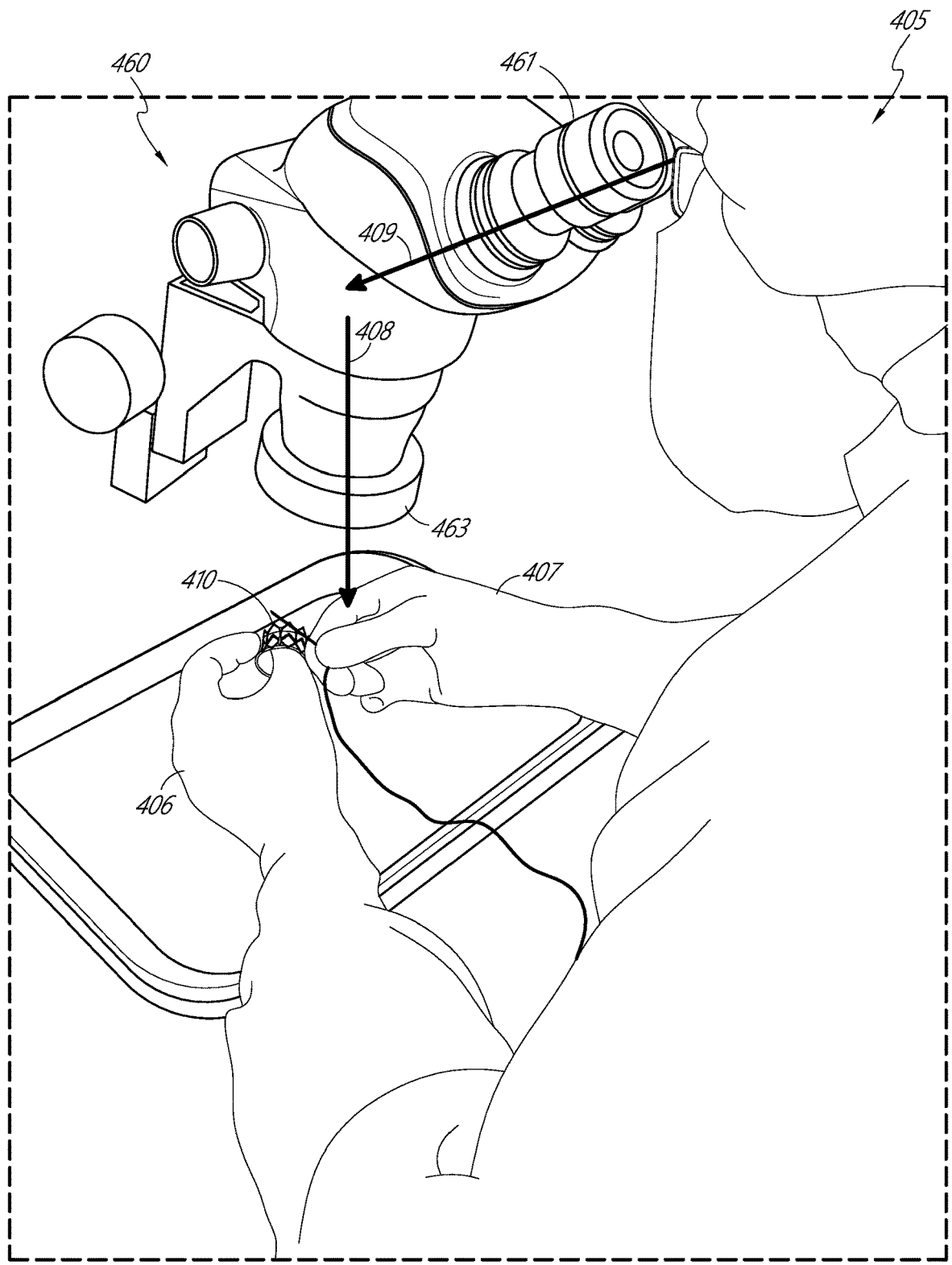
FIG. 4 illustrates an operator performing operations on an implant device in accordance with one or more embodiments.

Suturing of prosthetic heart valve devices and/or other implant devices, such as those described above, may be performed in various ways. For example, certain handheld processes for suturing prosthetic human implant devices may be implemented in which an operator utilizes both hands for holding, securing, and/or suturing the implant device. FIG. 4 illustrates an operator 405 performing operations on a prosthetic human implant device 410. For example, the operator 405 may suture an outer wireframe of the device 410 to an inner skirt or cloth, as described above, where the implant device 410 is a transcatheter heart valve device. In some embodiments, the implant device 410 may be a surgical valve device, or other type of implant device. The implant device 410 can be the same as or similar to any of the valves described herein or can be a different type of valve or implant device.

As illustrated in the diagram of FIG. 4, in some processes, an operator 405 may need to utilize both of the operator's hands for executing relevant suturing operations. For example, a first hand 406 may be used to hold and/or secure the implant device 410, wherein a second hand 407 may be used to manually operate a suturing needle or the like.

For the operator 405 to effectively execute the relevant suturing operations on the implant device 410, it may be necessary or desirable for the view of the implant device 410 to be magnified or otherwise enhanced in some manner. For example, as shown, the operator may further utilize a magnification system 460, such as a microscope, which may comprise an eyepiece component 461 as well as one or more lenses and/or refractive elements 463. In certain embodiments, the magnification system 460 may be designed such that the operator 405 may have a line of sight 409 at a first angle, wherein the magnification system 460 is configured to at least partially reflect light therein at a downward angle 408 to provide a depth of field at a targeted distance from the refractive elements 463. By holding the implant device 410, or target portion thereof, within the depth of field of the magnification system 460, the operator 405 may be able to observe an enhanced view of the implant device 410 or target portion thereof, which may be desirable or necessary to execute the precise suturing operations for effectively suturing the implant device 410.

In certain configurations, the use of a microscope as a visual aid in suturing implant devices may present ergonomic issues with respect to posture and/or vision of the operator 405. For example, the working plane presented by the microscope, with which the operator may be aligned when operating the microscope, may not adequately conform to the natural body position of the operator. To bring the operator's eyes into necessary proximity with the eyepiece 461 of the magnification system 460, undesirable neck and/or back strain or stress may be caused as the operator maintains the necessary posture for viewing the implant device 410 through the eyepiece 461. Therefore, use of a microscope, or similar magnification or viewing system, may be undesirable with respect to ergonomic and/or vision concerns.

Alternative systems and methods for visual aid in implant suturing may involve, for example, digital video systems, which may help to reduce operator neck strain, among other possible benefits. However, such systems may present difficulty with regards to focusing the implant or part being operated on under the camera associated with the video system when the implant or part is manually handled by the operator. With handheld operation, focus of the camera may be blurred and/or distorted when the implant or target part moves or is not aligned correctly with the lens axis, which may result in a loss of depth perception and/or other problems. For example, displays of a camera image can appear blurred due to slow pixel response times, refresh times, etc. when an implant or target part moves. This can be especially problematic when displaying high resolution images/video and/or magnifying the images/video. Furthermore, where the operator is required to hold the target implant, alteration of the viewing angle may further require twisting and/or contorting of the operator's hands in order to position the target implant, which may result in sub-optimal positioning. In addition, the location of the target implant may be such that a different viewing angle is required by the operator to view the target part than is required to view the monitor of the video system, which may cause eyestrain and/or other issues. Alternative solutions for visual aid in implant suturing operations may involve the use of a glass visor or the like, which may provide beneficial performance with respect to hand-eye coordination and/or neck placement. However, such tools may provide relatively poor zooming capabilities, and may cause substantial eyestrain for the operator over extended periods of time.

Figure 5:
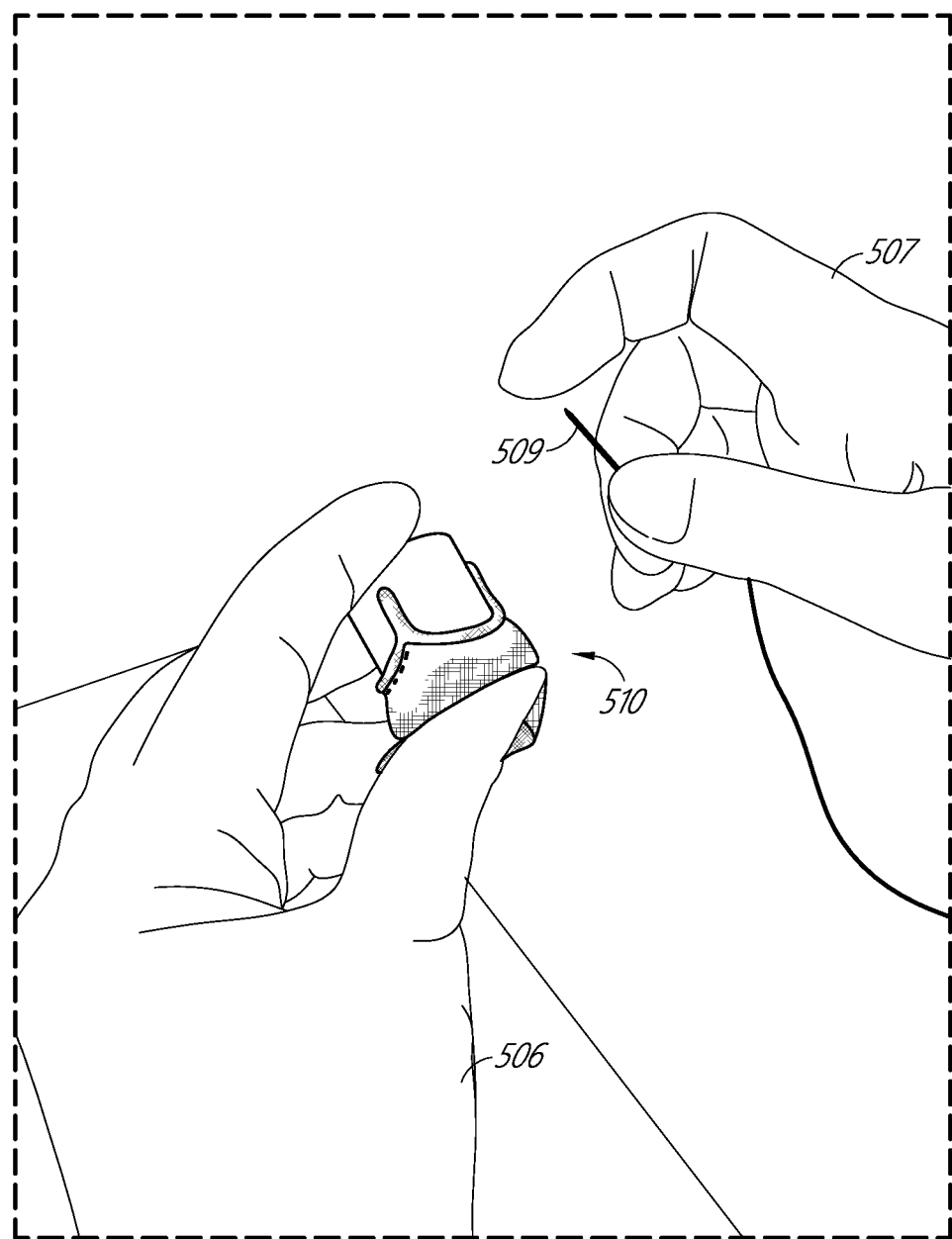
FIG. 5 illustrates a close-up view of a heart valve implant device being sutured using manual holding and suturing according to one or more embodiments.

FIG. 5 illustrates a close-up view of a prosthetic human implant device being sutured using manual holding and suturing, as described above. As shown, for handheld suturing solutions, a first hand 506 may be required to hold the target implant device 510, while a second hand 507 may be required to manipulate the suturing needle 509, or the like. According to certain processes, the operator may be required to hold one or more hands in a substantially constant position over prolonged periods of time to maintain the target implant device 510 (or desired portion thereof) within the depth of field of a microscope. Furthermore, the operator may be required to squeeze, push, pull, or otherwise exert manual force on one or more portions of the target implant device 510 and/or suture needle 509, thereby causing strain on muscles, joints, or the like, of the operator's hands and/or other anatomy. In certain embodiments, up to 20 pounds or more of force may be required to be exerted by the operator's hands in certain operations. Such forces may be required repeatedly throughout a suturing process and may result in various injuries to the operator.

Figure 6:
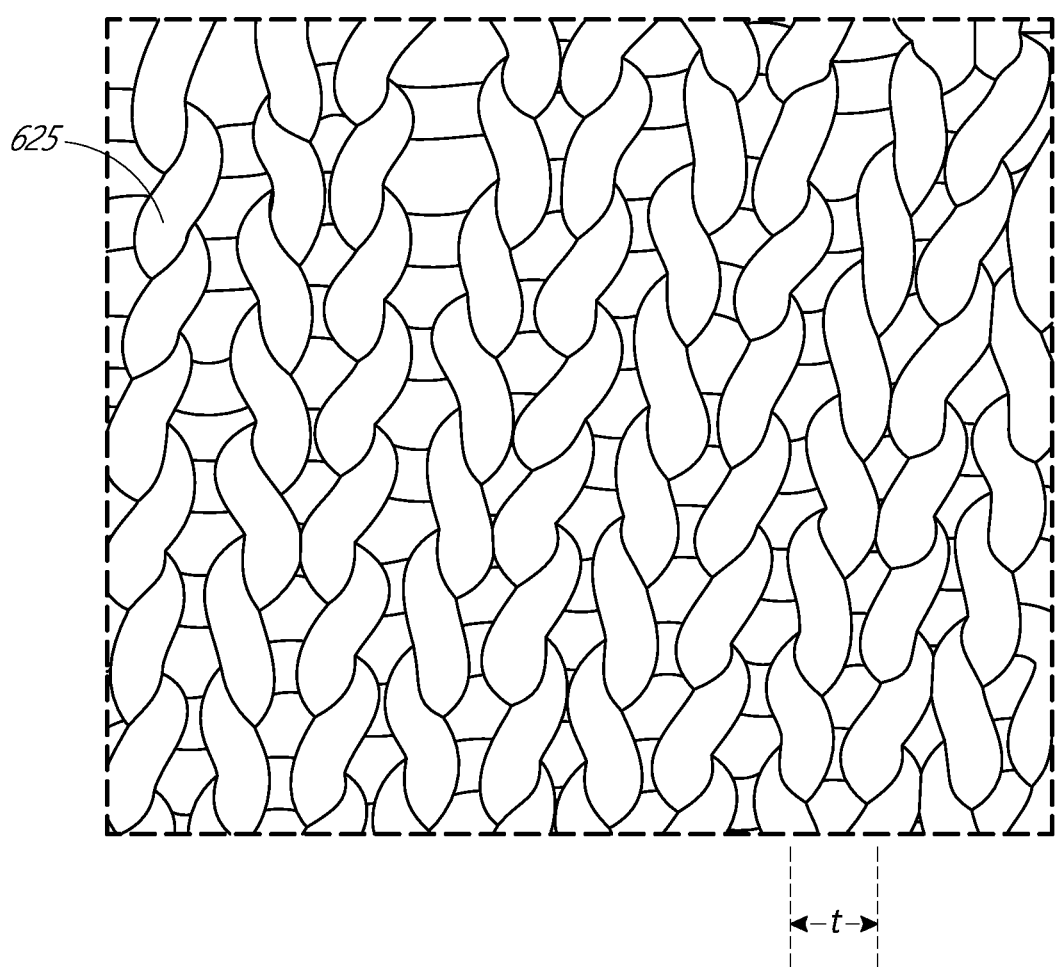
FIG. 6 illustrates a close-up view of a fabric associated with an implant device according to one or more embodiments.

Visual magnification and/or accurate positioning of an implant device may be necessary or desirable due at least in part to the dimensions of the cloth or other material being sutured in an implant suturing operation. For example, FIG. 6 illustrates a close-up view of a fabric associated with an implant device according to one or more embodiments. Such fabrics may comprise woven strands forming ribs having relatively small gaps therebetween. For example, each rib in a fabric region to be sutured may have a thickness t of approximately 0.2 mm, or less. For certain processes, the operator may necessarily or desirably wish to position and sew such a fabric within one-rib accuracy. Therefore, precise positioning and focusing of suturing components and targets is desirable.

In certain implementations, suturing (e.g., implant suturing) or other processes could be performed using one or more holder devices, such as a handheld gooseneck holder or mounted holder type device. However, such devices may not be rapidly adjustable to new locations, which may negatively impact performance efficiency or speed. Furthermore, refocusing of a microscope or other vision system to a location associated with such a holder device may be difficult. Handheld holders and tools may require operators to hold the holder or tool with one hand, thereby limiting the ability of the operator to use such holding hand to adjust the fabric or other material for tensioning and/or realignment.

Certain embodiments disclosed herein provide systems and processes for suturing components and/or devices (e.g., prosthetic human implant devices) using multi-access assist systems, such as in a direct-human-assist mode for suturing implant devices. Such systems may be configured to articulate a component or device (e.g., an implant device such as a human prosthetic heart valve device, etc.) precisely underneath an imaging system (e.g., a high-definition (HD) camera), wherein the precise positioning of the component or device may allow for necessary or desirable focusing and imaging of a desired position or targeted position (e.g., a current suture position or other position to be processed, inspected, etc.). Furthermore, the system may be further configured to reposition the component and/or imaging system to anticipate a subsequent position (e.g., a subsequent suture position, review or inspection position (e.g., for quality control inspection), or other position). In certain embodiments, a display associated with the system or implant suturing system can include visual aids to assist the operator in locating and/or interpreting an operation (e.g., a suture operation, review or inspection operation, processing operation, training operation, or other operation) to be performed. For example, such a display monitor may provide crosshairs, visual aids, overlays, comparative images, patterns, maps, and/or a type of reticle, or the like, to indicate the desired position or result (e.g., the desired suture position or completed suture).

Embodiments disclosed herein may provide improved ergonomics for operators, which may reduce medical costs and/or liabilities associated with hand, neck, shoulder, and/or vision injuries, for example. Furthermore, embodiments disclosed herein may provide improved reliability and/or repeatability for suturing processes, review or inspection, or other processes. For example, suturing an implant device or heart valve can require suture accuracy within a millimeter, half a millimeter, or less, but a suture location may be easily missed between ribs or threads, especially when implementing dual-handheld suturing procedures. Embodiments of the present disclosure can facilitate improved precision and can also provide the freedom of only requiring a single hand for certain suturing operations and/or other operations (e.g., inspection, processing, etc.).

Positional accuracy may be improved with respect to embodiments of the present disclosure through the use of systems incorporating one or more cameras, articulation arms, automated fixtures, monitors, etc., and/or a combination of more than one of these. Such systems can be used to position a targeted component or device (e.g., an implant device such as a human prosthetic heart valve device, etc.) in a desirable position with a relatively high degree of accuracy and repeatability. Such systems can also facilitate identifying desired positions (e.g., suture positions, inspection positions, etc.), such as with respect to frame and skirt suturing for a transcatheter heart valve.

Embodiments disclosed herein and the incorporation of features according to the present disclosure can provide or be used for training and/or technology transfer that may ultimately result in substantially reduced process or operation times and can help reduce the difficulty of operations and procedures. For example, it can be relatively difficult to convey training to an operator with respect to a particular procedure, and improved solutions disclosed herein can help reduce the complexity of certain procedures with enhanced training and/or by diverting certain procedures to mechanical components configured to manipulate the target device or component as necessary. Training of operators may be completed with improved efficiency, thereby potentially reducing costs and time. Embodiments can be used to guide operators through desired procedures or operations and demonstrate correct positioning and results. Quality-control feedback can also be provided to further improve quality for manufacturing and training. For example, heart valve implant suturing processes can be relatively labor-intensive and involve relatively long process times, which can result in increased costs and/or injuries. Embodiments disclosed herein and incorporation of features according to the present disclosure may provide for operator training and/or technology transfer that may ultimately result in substantially reduced process times, as well as reducing the difficulty of certain operations of implant suturing procedures. According to certain implementations, it can be relatively difficult to convey training to an operator with respect to suture locations for a particular procedure, especially where such procedures are implemented using dual-hand body mechanics to hold and manipulate the target device. Improved solutions disclosed herein can reduce the complexity of certain operations by diverting certain operations to mechanical components (e.g., automated fixtures) configured to manipulate the target device as necessary. Training of operators is simplified and may be completed with improved efficiency, thereby potentially reducing costs and time. Correct positioning and images of correct suturing may also be demonstrated and displayed to aid training. Quality-controlled feedback for further improving quality for manufacturing and training purposes can be implemented, e.g., the system may be able or programmed to move to key locations for inspection and/or recognition software may be able to detect issues, e.g., to detect whether a suture looks correct or incorrect. This can operate similar to facial recognition software with modifications to determine if the device or component appears to be correctly made or configured (e.g., has the correct shape of suture, or other features, etc.). Similar recognition software can be used for other processes as well to detect whether the target device looks like it should after a particular step, process, operation, etc. Various systems and/or devices disclosed herein may allow for fully automated processes or partially automated processes (e.g., at least partially automated implant suturing).

Suture Assist Articulation System

Figure 7A:
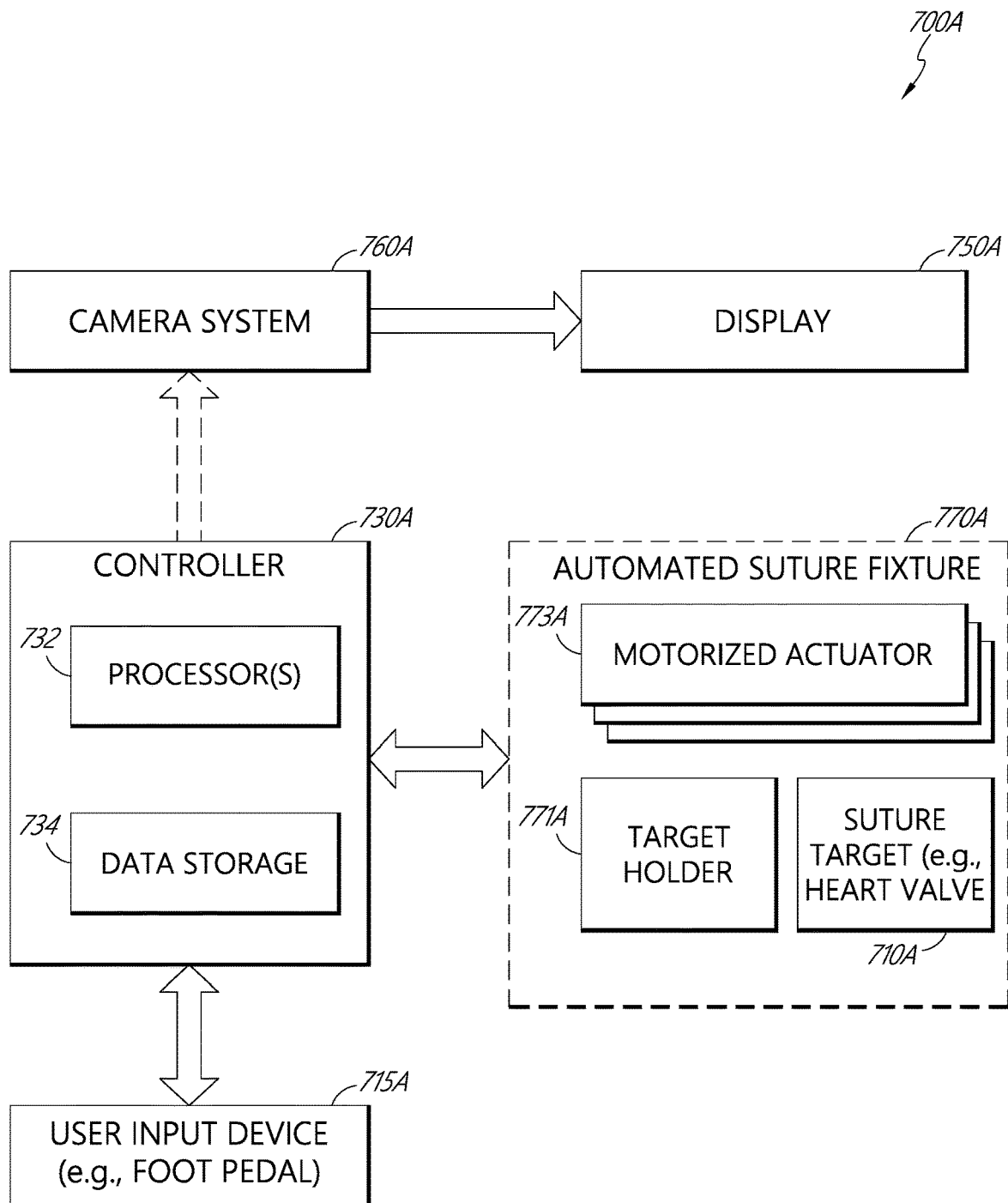
FIG. 7A illustrates a block diagram illustrating a suturing system in accordance with one or more embodiments.

Embodiments disclosed herein provide for systems, devices, methods, etc. for executing one or more operations (e.g., suturing operations, review or inspection operations, and/or other operations) for prosthetic heart valve implant devices for humans and/or other types of devices or components. FIG. 7A illustrates a suturing system 700A according to one or more embodiments. One or more components of the system 700A may be utilized for suturing heart valve devices or other implant devices, as described herein. In one embodiment, the system 700A includes a controller 730A configured to direct one or more components of an automated suture fixture assembly 770A according to a suture-assist process. In some embodiments, the automated suture fixture 770A can be an automated fixture or articulation device that is used for other or additional operations or procedures beyond suturing. The controller 730A can comprise one or more hardware and/or software components designed to generate and/or provide fixture control signals (e.g., suture fixture control signals) and/or data associated with one or more steps of a suturing process or other process. For example, the controller 730A can comprise a computing device including one or more processors 732, as well as one or more data storage devices or components 734, which can include volatile and/or nonvolatile data storage media. Although illustrated as a separate component in the diagram of FIG. 7A, the controller 730A can be a component of the automated suture fixture assembly 770A. In certain embodiments, the data storage 734 is configured to store process script data (e.g., suture process script data), which can comprise data indicating positioning of one or more components of the system 700A for various steps and/or stages of the suturing process or other process (e.g., for inspection, procedures, etc.). A process comprising a plurality of steps can be represented at least in part by numeric or other data sets representing positioning information for one or more components of the automated fixture assembly and/or one or more additional components of the system 700A for each respective step or stage of the process. For example, a suturing process comprising a plurality of suturing steps can be represented at least in part by numeric or other data sets representing positioning information for one or more components of the automated suture fixture assembly 770A and/or one or more additional components of the system 700A for each respective step or stage of the suturing process.

The automated suture fixture assembly 770A may comprise one or more components configured to articulate, operate, and/or position one or more motorized actuators 773A to present a target 710A (e.g., a heart valve or suture target), in a desirable or suitable position/presentation for convenient engagement or interaction therewith by an operator executing at least part of a process (e.g., a suturing process). In certain embodiments, the automated suture fixture assembly 770A includes a plurality of motorized actuators 773A that are mounted, attached, or connected to one another in a desirable configuration to provide a desirable range of motion for the automated fixture (e.g., automated suture fixture) for the purpose of articulating a target 710A (e.g., a suture target) associated with or held by the automated fixture 770A. In certain embodiments, a target holder component/assembly 771A can be associated with, or connected to, one or more of the motorized actuators 773A. The motorized actuators 773A can each comprise one or more rotating, translating, or otherwise articulating members driven by a motor, a piston, or the like. Examples of automated suture fixture assemblies and associated components are described in greater detail herein with reference to FIGS. 10, 11, 18-25, and 28-30.

The motorized actuators 773A can be configured to provide a number of degrees of freedom of movement for the target holder 771A and, consequently, a suture target 710A coupled to the target holder 771A. In some embodiments, the number of degrees of freedom is greater than or equal to 3, greater than or equal to 4, greater than or equal to 5, or greater than or equal to 6. The degrees of freedom can include positioning in any of the three spatial dimensions (e.g., movement in the x-axis, y-axis, and z-axis; horizontal movement, vertical movement, or a combination of horizontal and vertical movement), rotation (e.g., rotation about the x-axis, about the y-axis, and/or about the z-axis), and/or rotation of the target holder 771A around a longitudinal axis of the suture target 710A (e.g., keeping the position and pointing direction of the suture target 710A fixed while rotating the suture target 710A around its longitudinal axis to expose a different portion of the suture target 710A to an operator and/or camera system 760A).

In certain embodiments, the controller 730A can provide control signals for directing the positioning of the motorized actuators 773A based on a positioning script, suture process script, and/or user input provided by an operator. For example, the system 700A can include a user input device 715A, which can be used by an operator to provide input directing the operation of the controller 730A and/or automated suture fixture assembly 770A. For example, user input device 715A can comprise any suitable user input interface, such as a mechanism for user input in connection with a graphic user interface associated with an electronic display, wherein an operator can provide input through interaction with the interface. In some embodiments, the user input device 715A can comprise one or more physical switches, buttons, pedals, sensors, or the like, wherein a user may provide input through engagement of such mechanism(s). In some embodiments, the input can be provided using voice commands and/or voice recognition software. In some embodiments, the user input device 715A comprises a foot pedal that may be pressed or otherwise engaged by the operator substantially at the same time as the operator is interacting with one or more other components of the suturing system 700A. For example, the operator can activate the foot pedal while sitting or standing at a suturing station and engaging with the suture target 710A with one or more hands of the operator. For example, the operator can engage the foot pedal as a signal to advance from one step or stage of the present suturing operation to a subsequent step or stage, e.g., the input device 715A can provide input to the controller to advance the system through a script moving the automated fixture and target to each position in sequence.

In certain embodiments, the system 700A includes a visualization system or camera system 760A, which may be configured to perform various imaging functionality for assisting with the suturing procedure being executed by the operator. For example, the camera system 760A may be configured to generate an image, such as a close-up image and/or high definition image, of the suture target 710A (e.g., an image of a portion of the target 710A to be sutured, inspected, treated, etc.) and/or associated components of the automated suture fixture assembly 770A for the purpose of providing a visual aid for the operator in executing suturing operations, inspections, or other operations. The camera system 760A can capture image data for quality control or other purposes at various stages of the suturing procedure or other operation. The camera system 760A may operate in connection with a display system 750A, such as an electronic computer display, or the like. Therefore, in certain embodiments, the operator can view enlarged imaging of a suture target (e.g., an image of a portion of the target to be sutured) while executing suturing operations thereon, or otherwise inspecting or engaging therewith. In certain embodiments, the camera system 760A maintains a constant focus or depth of depth during multiple steps of a suturing process, while the automated suture fixture 770A articulates the suture target 710A in such a way as to bring a target portion of the suture target 710A into the depth of field of the camera 760A substantially automatically and hold it in place during each step of the process so that the suture target 710A remains in focus.

Figure 7B:
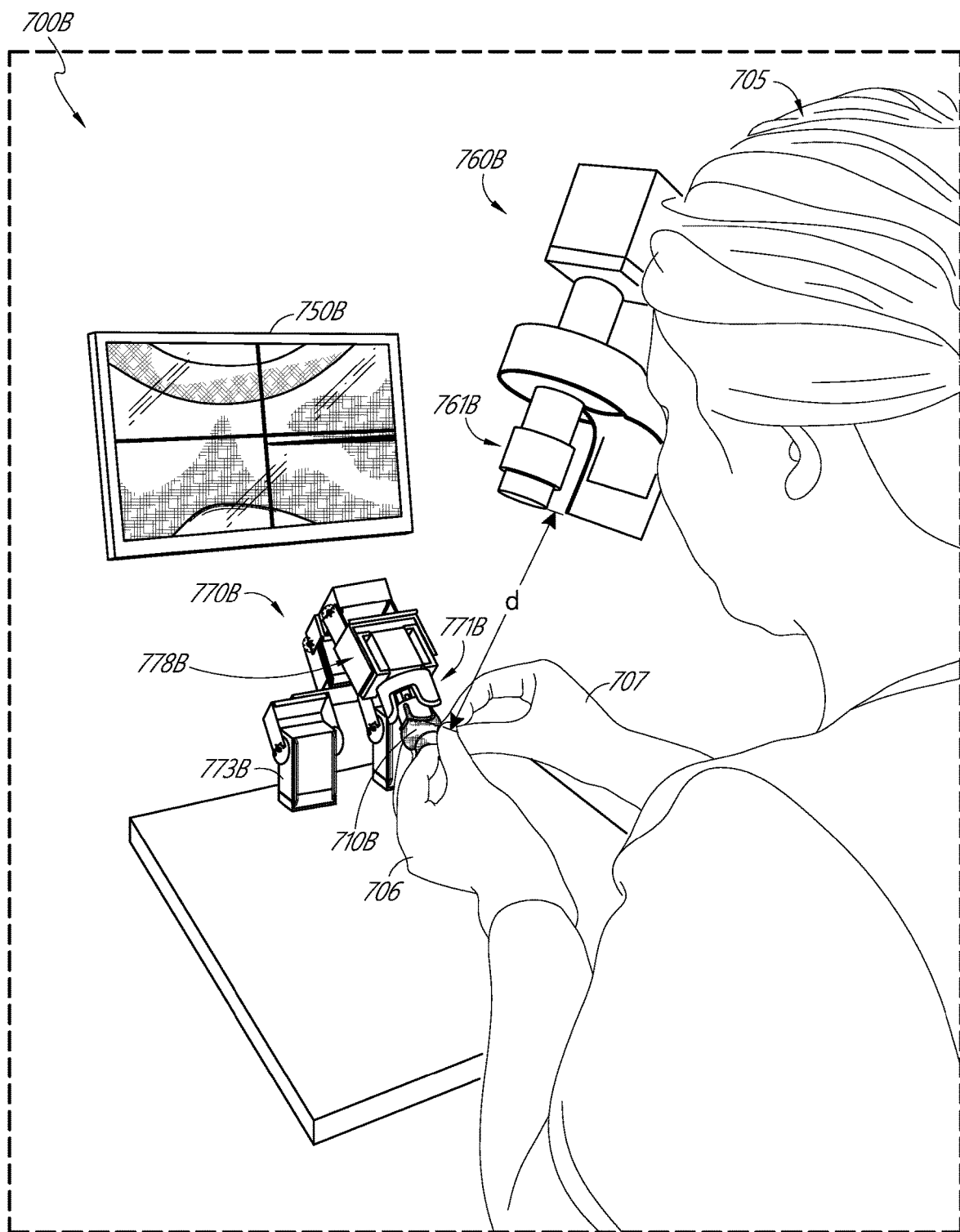
FIG. 7B illustrates an operator executing suture operations with respect to an implant device using a suture assist system in accordance with one or more embodiments.

FIG. 7B illustrates an operator 705 executing suture operations with respect to a prosthetic human implant device (e.g., heart valve) 710B using a suture assist system 700B in accordance with one or more embodiments. Although a plurality of components and devices are illustrated in the system 700B of FIG. 7B, it should be understood that suture assist functionality may be implemented in systems having one or more additional components and/or systems that omit one or more components illustrated in FIG. 7B. In certain embodiments, the system 700B includes an automated suture fixture 770B, which may comprise one or more actuator devices (e.g., servo actuator devices), which may be coupled in one of various configurations allowing for an articulation arm 778B to be articulated to provide multiple degrees of freedom when manipulating and positioning the coupled implant device 710B. For example, the automated suture fixture 770B may be configured to articulate the arm 778B towards and/or away from the operator 705, up and/or down, in a clockwise and/or counterclockwise direction relative to one or more different axes of rotation (e.g., to move or flip the inflow end and outflow end so one or the other is closer to the operator), in various directions/positions relative to x-, y-, and z-axes, and/or in other directions/movements. Furthermore, the arm 778B of the suture fixture 770B and/or an associated implant holder component 771B may be configured to rotate (e.g., rotate about a central or longitudinal axis of the holder 771A, 771B and/or of the target 710A, 710B) clockwise or counterclockwise in order to present different portions or regions of the implant device 710B to the user 705. A distal arm portion 778B of the automated suture fixture 770B can allow for the operator 705 to move the target or implant device 710B in a position to expose one or more portions of the implant device 710B (1) to a viewing assembly 760B (e.g., a camera or microscope assembly), or lens thereof and/or (2) to the operator 705 (e.g., to the operator's hand and/or eye) to perform a procedure (e.g., a suturing step, inspection step, etc.).

In certain embodiments, the automated suture fixture 770B comprises a plurality of motorized actuators (e.g., servo actuators) physically coupled to one another. By constructing the automated suture fixture 770B using a plurality of motor components (e.g., servo motor components), the system 700B may be relatively inexpensive and/or advantageously provide an enhanced range of motion, as well as multiple axes of rotation. In certain embodiments, the automated suture fixture 770B comprises a plurality of actuator devices (e.g., servo actuator devices) daisy-chained together and implemented using a software script to provide cooperative functionality for the purpose positioning the implant device 710B. For example, the actuator devices or servo actuator devices (e.g., servo motor devices) may be mounted, or configured to be mounted, horizontally or vertically or at an angle, and may be articulated in any desirable direction. For example, the automated suture fixture 770B may be configured to articulate in a snake-like and/or crane-like configuration. FIGS. 18-25 and 28-30 illustrate examples of snake-like configurations of an automated fixture that can be used in suturing procedures as an automated suture fixture and/or in other procedures.

The configuration of the automated suture fixture 770B may provide the weight and/or size for the automated suture fixture 770B that is relatively small and convenient for use in applications designed to assist in the positioning and manipulation of relatively small devices, such as the prosthetic human implant device 710B. The relatively small size of the system and automated fixture also allows for use in a more compact workspace like those often used for suturing prosthetic heart valve implants, e.g., the small size can fit and be used even on a relatively small desk/table, which allows for more efficient use of building and work areas. In certain embodiments, the individual actuator devices (e.g., the individual servo actuator devices) of the automated suture fixture 770B may comprise brushless potentiostat and/or magnetic encoder devices. In certain embodiments the actuator devices may be implemented using piezoelectric control with analog voltage signals. In certain embodiments, one or more components of the automated suture fixture 770B may be controlled using pulse width modulation control signals, such as control signals spaced by between 0 to 2 μs, for example. In certain embodiments, multiple motor components (e.g., multiple servo motor components) of the automated suture fixture 770B may share one or more common leads with a multiplex signal, such as a three-lead connection. In certain embodiments, the automated suture fixture 770B comprises four or five or more servo motor devices. Devices and fixtures disclosed herein may be remote-controllable or at least partially remote-controllable.

The automated suture fixture 770B can further comprise a suture target holder assembly 771B, which may be configured to hold or secure the suture target (e.g., the prosthetic human implant device) 710B that is the subject of the suturing process that the operator is engaged in. In certain embodiments, the suture assist system 700B comprises a camera subsystem 760B. In certain embodiments, the camera 761B remains in a substantially static configuration during execution of a suturing procedure, wherein the automated suture fixture 770B articulates the target implant device into desirable focus with the camera 761B during the procedure. In certain embodiments, the camera system 760B may be configured to manually or automatically articulate and/or focus to a target position to provide a precise image of a target suture position for the operator's benefit. For example, the positioning/configuration of the camera 760B may be controlled at least in part by a controller executing a suture process script as described herein. In certain embodiments, the system 700B includes multiple cameras configured to provide multiple-perspective imaging (e.g., a dual-perspective imaging) of the implant device 710B and/or automated suture fixture 770B, which may help to eliminate or reduced blind spots and/or improve ease of operation. The suture assist system 700 can further comprise a display monitor 750B (or multiple display monitors), which may work in concert with the camera assembly 760B and/or automated suture fixture 770B to present to the operator 705 an image identifying a target position (e.g., a target suture position) to further improve precision and ease-of-use of the system 700B.

The assist system 700B may represent a multi-access assist system for use in a direct human assist for procedures (e.g., for suturing prosthetic human implants, such as heart valves, for inspection and quality control, and/or for other procedures). In certain embodiments, the automated suture fixture 770B can hold the target device or implant device 710B and articulate the target device or implant device 710B to a desired position underneath the camera lens 761B, which may be, for example, a high-definition (HD) camera, which may provide further precision in monitoring the procedure (e.g., in the suturing procedure, inspection, or other procedure). The automated suture fixture 770B may advantageously position the implant device 710B or target device to a desired in-focus position within the depth of field of the camera 761B, e.g., with respect to a point or region on the implant device 710B that is to be sutured according to the implant suturing process.

Configuring the holder assembly 771B of the automated suture fixture 770B to hold, secure, articulate, or move the prosthetic human implant device 710B can allow for execution of suturing operations by the operator 705 using one less hand than may be required in systems in which an operator is required to manually hold the implant device in the desired suturing position. The free hand of the operator 705 may be available to perform various operations not available in procedures in which both hands of the operator are required for handling and suturing the implant device. For example, a free hand of the operator 705 may be used to adjust cloth being sutured, reposition suturing threads, assist with tying knots, push or pull the needle, and/or the like. Further, allowing the free hand to rest may beneficially reduce injuries or pain for an operator.

The automated suture fixture 770B can be configured to align the target or implant device 710B with the focal position of the camera system 760B without the need for the operator 705 to determine and execute the appropriate positioning to provide a view of the target or a portion of the target (e.g., a desired suture point) on the display device 750B. In some embodiments, the camera system 760B may further be configured to align the camera 761B with the plane of operation presented by the automated suture fixture 770B.

In certain embodiments, the gear train slop present in the automated suture fixture 770B may advantageously be less than ½ mm at a distal portion thereof. The automated suture fixture 770B may comprise one or more encoders for articulating the various components of the device. The position of the one or more encoders may be designed in order to provide satisfactory precision of position of the distal end of the actuator arm 778B to allow for precise positioning of the target device 710B for imaging thereof. In certain embodiments, one or more encoders may be connected at an output portion of the automated suture fixture 770B, such that slop in the system may be corrected to position the implant device 710B at the precise position as directed by the script by which the automated suture fixture 770B is operated. In certain embodiments, one or more magnetic encoders having, for example, 12-bit resolution or other resolutions, may be utilized in connection with the automated suture fixture 770B.

In certain embodiments, a distal articulation arm 778B of the automated suture fixture 770B may generally present a downward-angled position to allow for proper positioning of the implant device 710B with respect to the position of the operator 705, as shown in FIG. 7B. Furthermore, the camera 761B may advantageously provide an at least partial side angle of the implant device 710B, which may provide a good working view of the target suture position with respect to the operator 705 orientation shown. With the automated suture fixture 770B configured to position the implant device 710B substantially within the depth of field of the camera 761B, it may not be necessary for the camera 761B to adjust focus from one step of the suturing procedure or other procedure to the next.

The suture assist system 700B may be configured such that the articulation arm 778B of the automated suture fixture 770B may be manually or electronically altered by the operator 705 to train the automated fixture 770B to a custom position, e.g., to record/program position information so the system or automated fixture 770B can return to that position automatically during a procedure. For example, the operator 705 may manipulate the articulation arm 778B to provide accessibility to as much of the target or valve 710B as possible vis-à-vis the desired work position or posture of the operator 705. The articulation arm 778B may be mechanically moved into the desired position and frozen or held in that position, wherein in the frozen/held position, a data capture is executed representing the position of the arm 778B, such that the position can be re-created at a future time in connection with a similar operation/procedure. The position information (e.g., information representative of a position or that can be used to cause the automated fixture and/or articulation arm to move to a particular position) can be saved as part of a procedure script (e.g., a suturing procedure script, inspection script, etc.). For example, since a procedure for suturing and/or a procedure for inspecting the implant device 710B can, and generally will, involve multiple different positions of the implant device 710B, the system 700B can be configured to store a data script comprising information relating to each step and/or position of the procedure, such that the specific positions/steps may be replayed at a later time connection with the procedure (e.g., an implant suturing and/or inspection procedure associated with the implant device 710B).

Figure 8A:
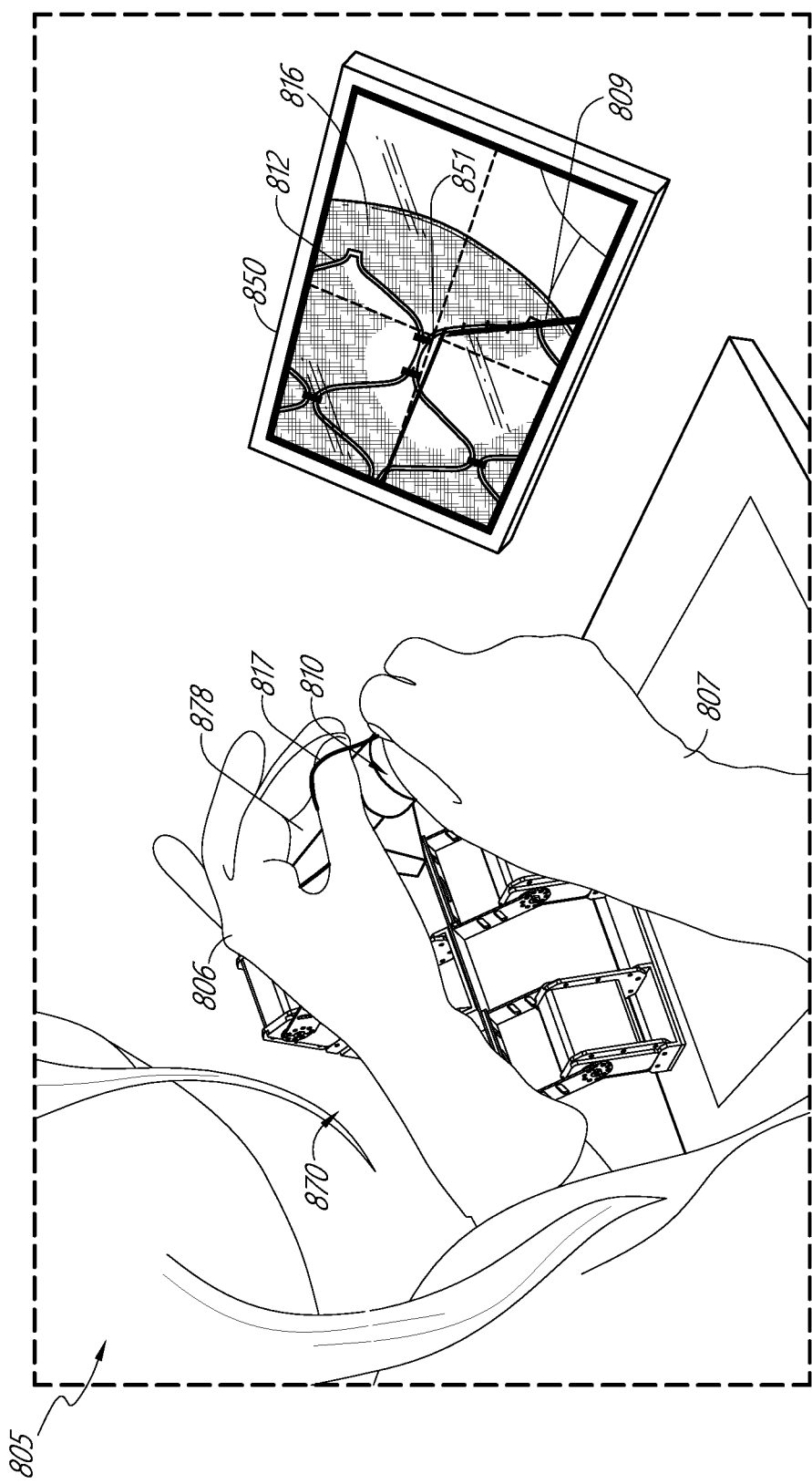
FIGS. 8A-8C illustrate respective stages of an operator executing a suturing operation on an implant device in accordance with one or more embodiments.

In certain embodiments, utilization of an automated suture fixture like that shown in FIG. 7B and described above may allow for improved quality and/or convenience associated with whip-type stitches of certain implant devices. FIG. 8A illustrates an operator 805 executing a suturing operation on a prosthetic transcatheter heart valve implant device 810 comprising a wireframe 812 disposed about a skirt component 816. The operation executed by the operator 805 can involve a whip-type stitch, wherein a needle 809 and thread 817 are passed from outside of the implant device cylinder, through the implant device cylinder, and drawn out from within the implant device cylinder. FIG. 8A shows the process step of puncturing the outside of the implant device cylinder with the needle 809, wherein an articulation arm 878 of the automated suture fixture 870 that holds the implant device 810 is in a slightly downward-angled position to thereby present the exterior surface of the implant device to the operator with the target suture position 851 focused thereon. At each stage and/or step of the suturing process represented in FIGS. 8A-8C, the display 850 may show an image (e.g., a close-up image and/or high-definition image) of the relevant target position for the respective stage/step.

Figure 8B:
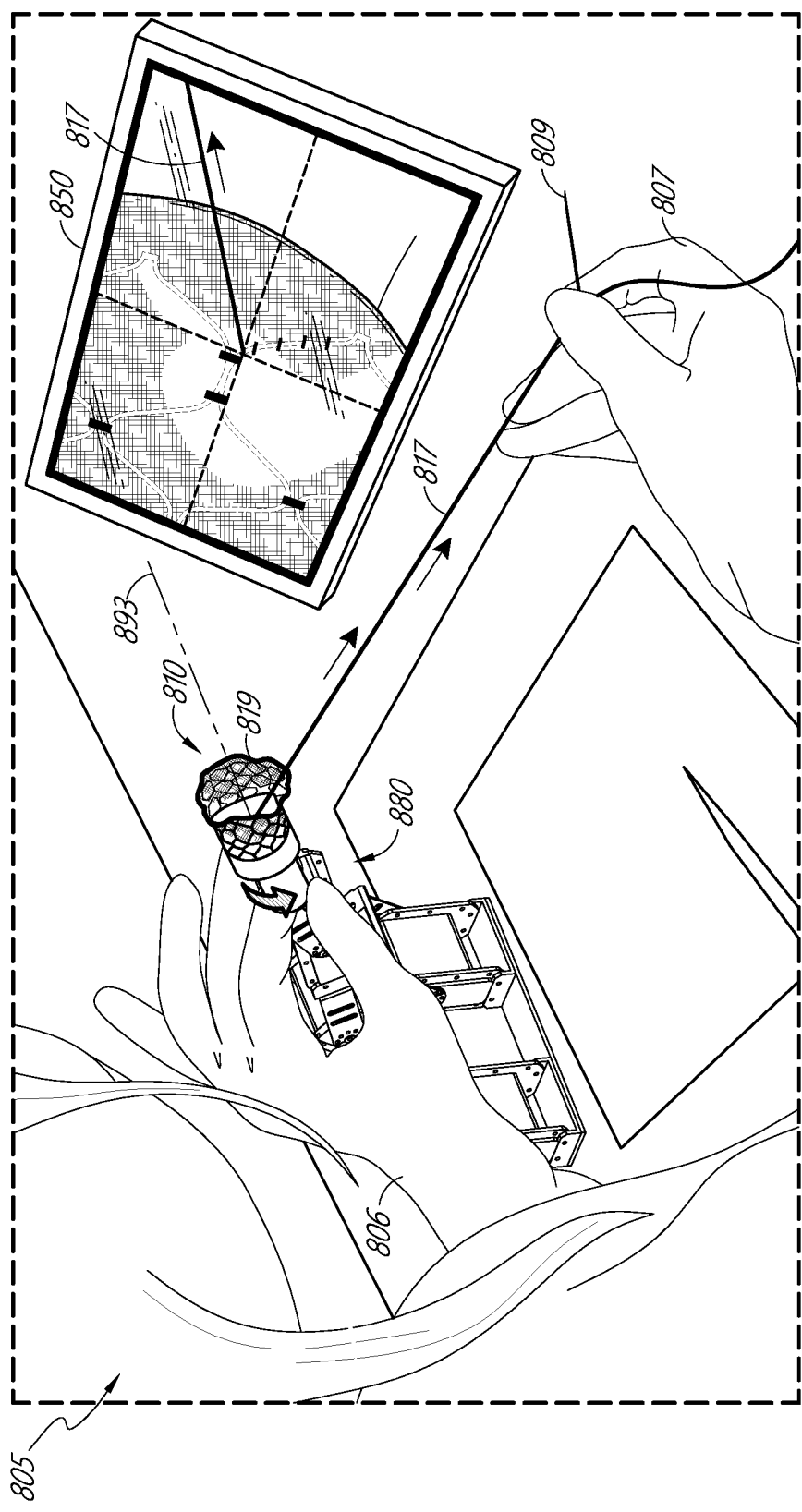

FIG. 8B illustrates the operator 805 drawing out the needle 809 and/or thread 817 from the inside 819 of the cylinder of the implant device 810 after the needle 809 has punctured the implant device 810 from the outside of the cylinder portion of the implant device 810, which is shown in FIG. 8A. When the operator 805 draws the needle 809 out of the inner cylinder 819, the articulation arm 878 may articulate to present (or make more accessible) the inside (e.g., a desired portion of the inside) of the implant device cylinder to the operator to allow the operator to more easily locate and grasp the needle 809 and/or draw the needle 809 and thread 817 out, which can reduce the risk of catching or snagging. In some embodiments, the implant device 810 can be maintained in the same position or at the generally downward projecting angle associated with the puncture operation of FIG. 8A when drawing the needle 809 and thread 817 from inside of the cylinder of the implant device 810. The display monitor 850 can remain focused on the suture position associated with the puncture of FIG. 8A to show the threaded suture formed by puncturing the outer cylinder of the implant device 810 as shown in FIG. 8A or can focus on another portion of the target or implant device 810 (e.g., on the location where the needle 809 will be pulled out). Presentation of the inside of the implant device cylinder 819 to the operator 805 can be accomplished at least in part through the rotation of the implant device 810 about a central or longitudinal axis 893 thereof. For example, the holder component 880 coupled to the articulation arm may be configured to rotate about the axis 893.

Figure 8C:
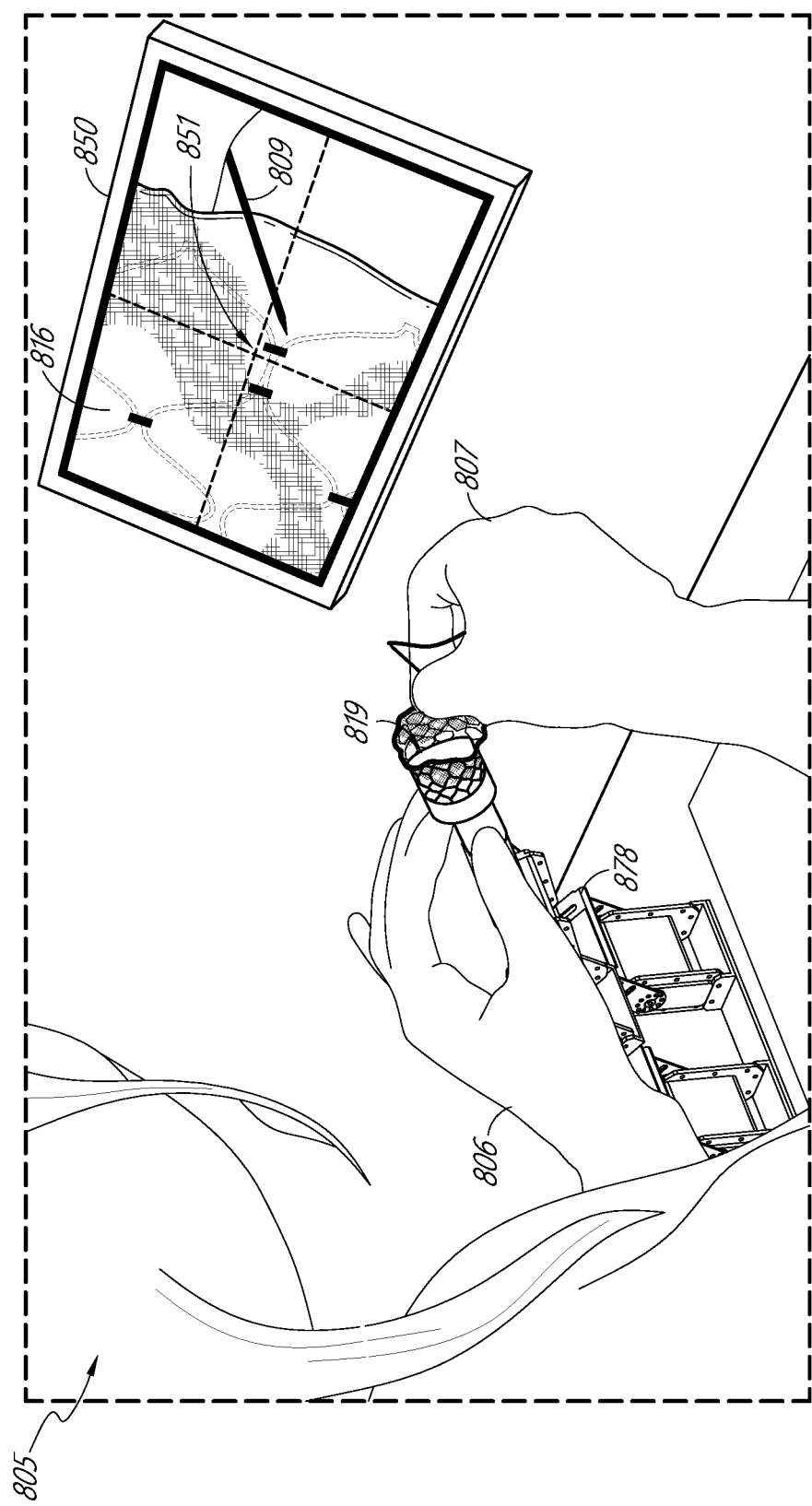

FIG. 8C illustrates the articulation arm 878 positioned in a generally upward-projecting position in order to present to the operator 805 a portion of the inside 819 of the cylinder of the implant device 810. By presenting the inner surface of the cylinder of the implant device 810 to the operator and to the camera lens 861, the articulation arm 878 can allow for the operator 805 to more conveniently access the target suture position for pulling the needle 809 through and/or using the needle 809 to puncture the inside surface of the cylinder of the implant device 810 (e.g., an inside surface of the transcatheter heart valve skirt component, as described in greater detail above). Presenting the inner surface of the cylinder of the target device or implant device 810 can also allow the camera lens 861 to be focused on the target suture position 851 and allow better display and viewing of the target suture position. With the target suture position 851 prominently displayed on the display monitor 850, the operator 805 may be instructed and/or assisted in an inside-to-outside suturing step for completing the suture wrapping around the frame 821 of the implant device 810. By providing convenient repositioning of the articulation arm 878 for exterior and interior needle puncturing operations, the system 800 may provide a means for suturing a transcatheter heart valve or other type of implant or target device requiring exterior-to-interior stitches and vice versa. The precise repositioning of the articulation arm 878 (e.g., according to a particular script or program) can reduce the risk of thread wrapping or other mis-stitching by the operator 805.

Suture Point Imaging

Figure 9:
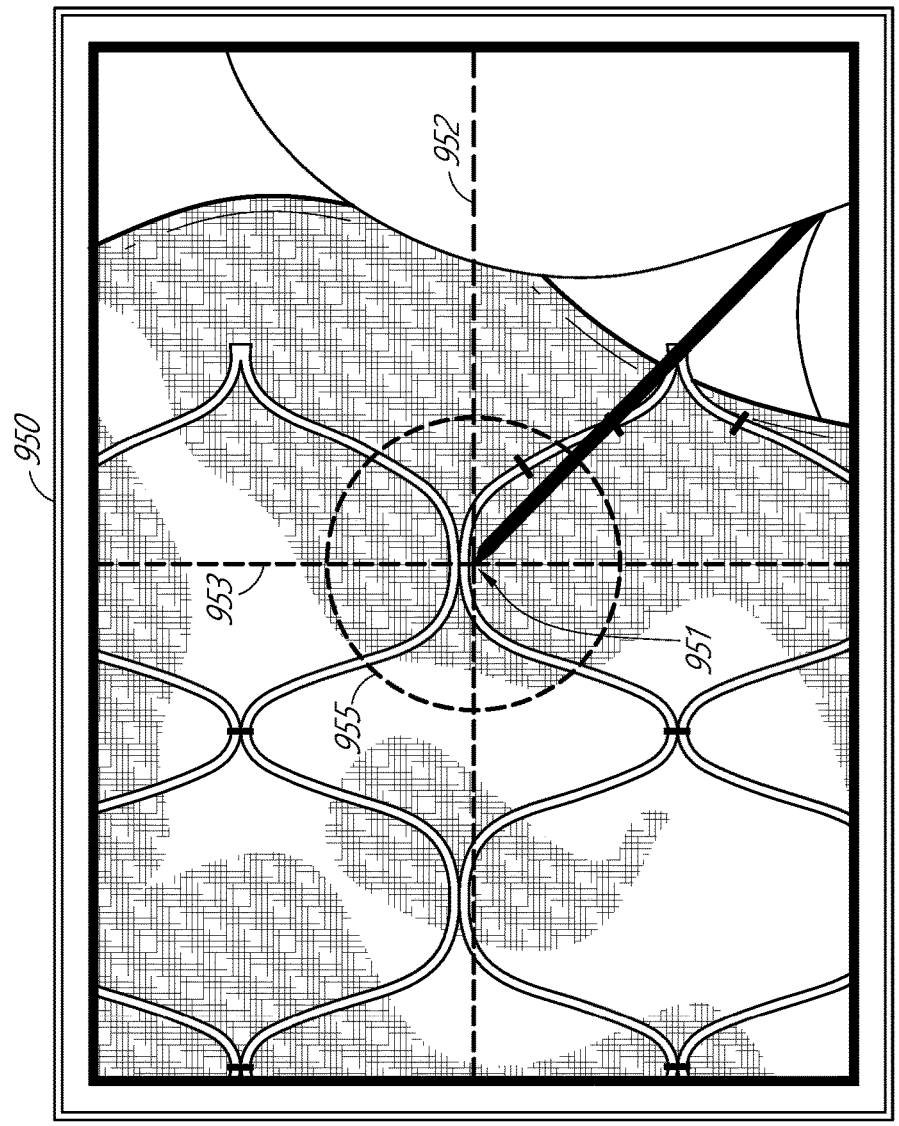
FIG. 9 illustrates a display monitor displaying and image of a target suture position for a prosthetic human implant suturing procedure in accordance with one or more embodiments.

FIG. 9 illustrates a display, screen, or monitor 950 for displaying an image of a target position or target suture position 951 of a target device or prosthetic human implant device, e.g., the image of a target suture position can be displayed for a suturing procedure in accordance with one or more embodiments. For example, the display monitor 950 may be the same as or similar in certain respects to the display monitors 750A, 750B described herein with reference to FIGS. 7A and 7B and/or display monitor 850 described herein with reference to FIGS. 8A-8C. In certain embodiments, the display 950 may be configured to display an image captured by a camera system associated therewith (not shown), such as may be similar to certain camera systems illustrated in other figures and described in detail herein (e.g., camera system 760A, 760B). The display 950 can provide visual targeting of a target location/target stitch location 951 or general area using one or more on-screen visual aids. For example, the display 950 may have disposed or projected thereon one or more crosshair guidelines 952, 953, and/or other reticle tool, such as a circular reticle 955, which may encompass the target suture point 951. With respect to embodiments comprising crosshair guides (e.g., vertical and horizontal crosshair guides), the intersection of such crosshairs may be at a target point, which can be designated as the target suture point 951. Although a circle reticle is illustrated, it should be understood that reticles and/or other visual aids associated with the display monitor 950 may comprise any suitable or desirable shape configuration, or the like. Optionally, a target location or point may be positioned at a particular location on the display 950 (e.g., the target location or point may always or sometimes be positioned at the center of the monitor or display) regardless of whether other visual aids are or are not used. Furthermore, in certain embodiments, animation overlays may be superimposed on a camera image displayed on the display 950 to further assist the operator in interpreting or identifying the target suture point and/or the associated suturing action or other procedure the operator is to take.

With the aid of the display 950, it may not be necessary for the operator to be burdened with manually focusing the implant device being sutured to specific focus points. For example, manual focus may be unnecessary when the display 950 is part of a suture assist system comprising target implant articulation mechanics and/or a camera system configured to collectively achieve the desired focus at the target suture point or other target point for a given step of a suturing procedure or other procedure. As another example, an articulation arm securing or holding the target implant device may be configured to position the suture point of the implant device within the depth of field of the associated camera system. With the focused image presented clearly on the display 950, the operator may be spared at least in part eye strain or other discomfort which may generally be associated with efforts to visually inspect and/or configure an implant device to achieve the desired focus. Further, proper positioning may make various steps and procedures easier to accomplish and easier on the hands and arms of an operator.

In certain embodiments, the visual aid(s) (e.g., crosshair 952, 953 and/or circular reticles 955) can be displayed as stitch-counting visual aids. The reticle 955 can be calibrated to a desired position. Furthermore, while the crosshair target 951 can identify the target stitch location, the circular reticle 955 can comprise additional notches or indicators providing further information with respect to a current stitch operation, such as a numbered stitch count. For example, the circular reticle 955 can rotate with each stitch as a means of identifying stitch count in certain embodiments. The reticle(s) can be used to index certain stitches accurately on the display 950. With the circular reticle 955, it may not be required for the operator to count stitches, and therefore the mental burden on the operator may be at least partially reduced and human error in the counting can be eliminated or reduced. Furthermore, with the operator able to maintain focus on stitch without relying on himself or herself to hold the position of the implant device in the desired orientation with respect to the magnification or visualization system, the operator can expend energy towards other aspects of the process, thereby potentially improving quality and/or efficiency. Markings associated with various visual aids (e.g., markings of the visual assistance reticle(s)) may be useful in alignment, placement, and/or measurement of stitches and/or other suturing operations. In certain embodiments, the field-of-view of the display monitor 950 can be adjustable to conform to the preferences of the operator, to be placed in an ergonomically beneficial position, or as appropriate for a particular suturing operation or other operation.

In certain embodiments, the display 950 may be configured to present thereon operator instructions for executing suturing operations or other operations, as well as other information which may be pertinent to the procedure or otherwise associated with the procedure (e.g., step by step instructions, reference images of correctly completed suture steps or procedure steps, warnings/cautions, tips/suggestions, FAQs, etc.). For example, the display 950 may present timing elements, which may be used to improve efficiency and/or aid the operator in determining points or periods of time during which certain operations are to be executed. In some embodiments in which the target implant device may comprise materials that are required to maintain a certain degree of moisture in order to retain desired functional properties or qualities (e.g., tissue used to form leaflets of a valve can be required to maintain a certain degree of moisture), reminders and/or instructions may be presented on the display 950 to the to the operator to remind the operator to saturate or moisten such components. Furthermore, in certain embodiments, the display 950 may present qualitative measurement or analysis information with respect to the procedure being executed by the operator, such as sensed characteristics of the implant device and/or one or more components or features thereof, such as moisture levels, tension readings with respect to certain stitches, or the like. The system can include sensors configured to detect these characteristics, e.g., moisture level sensors, tension sensors, etc. The system can include a timer, clock, or other time tracking device/operation to track how long the various steps, operations, procedures, etc. take and/or to allow an operator or other person (e.g., a supervisor) to review different times or images associated with different times.

In certain embodiments, still images can be captured as displayed on the display 950 and/or captured by the associated camera system (not shown). Such captured images may be used to provide quality-control data points. For example, image file data can be compiled and stored in association with the specific implant device of the procedure, the procedure, and/or the operator involved in the procedure, wherein such information can be used to evaluate the quality and/or other aspects of the implant device, procedure, and/or operator. The display 950 can be positionable for viewing by the operator in any desirable position, which may allow for relatively low-stress posture and/or interaction of the operator to improve ergonomics.

Automated Suture Fixture

Figure 10:
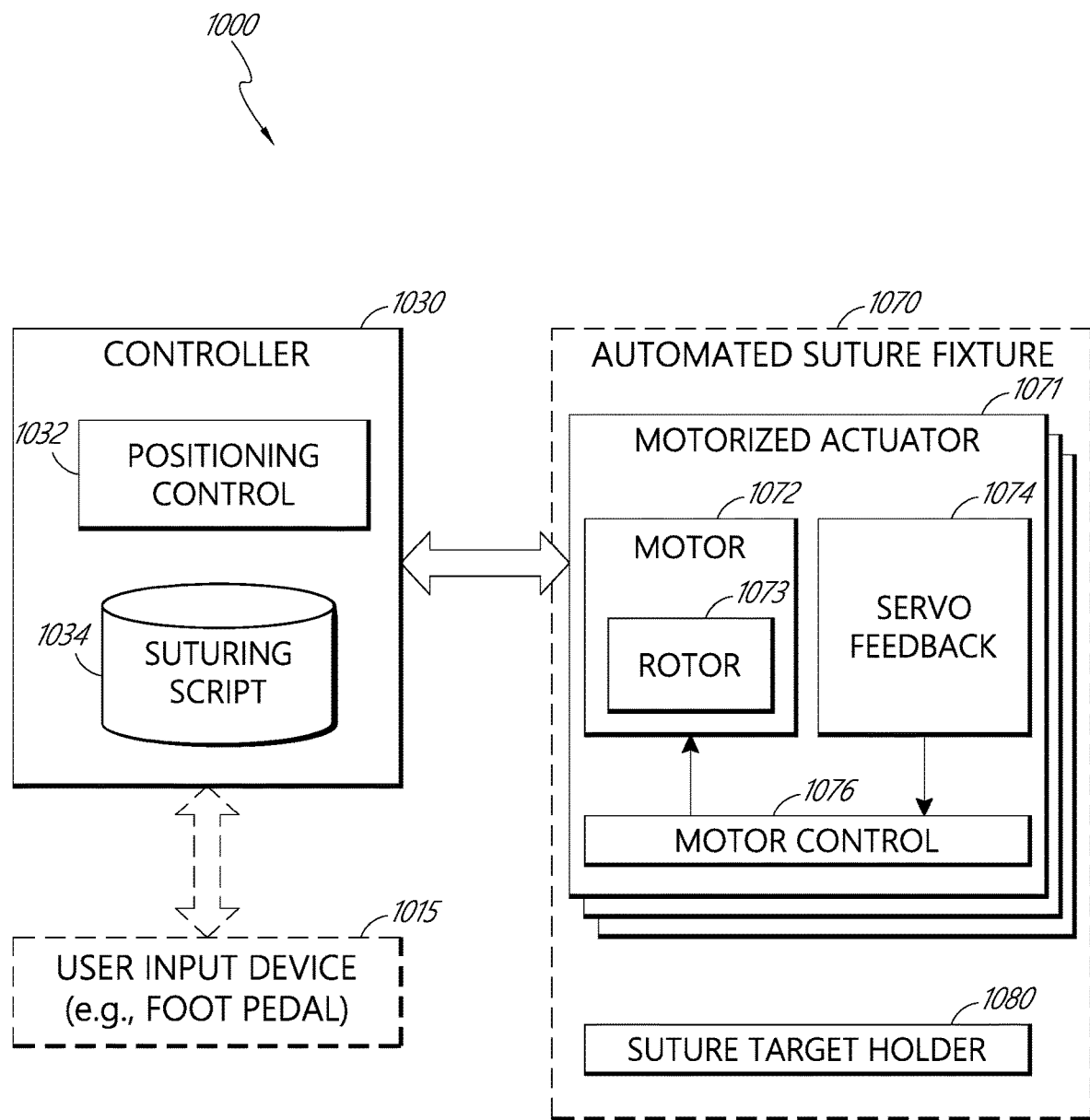
FIG. 10 illustrates a block diagram illustrating a control system for controlling an automated suture fixture according one or more embodiments.

As illustrated in FIG. 7A and described in detail herein, suture assist systems in accordance with the present disclosure may comprise an automated suture fixture for articulating a suture target (e.g., prosthetic human heart valve implant) to a desired suture position or other process position. FIG. 10 illustrates a block diagram illustrating an exemplary control system 1000 for controlling an automated suture fixture 1070 (although shown as an automated suture fixture, it may be an automated fixture used for other operations or procedures instead of or in addition to suturing) according to one or more embodiments. The system 1000 includes an automated suture fixture 1070 configured to receive control signals from a controller module 1030. The controller module 1030 may comprise a combination of software and/or hardware components configured to generate control signals for at least partially directing the operation of the automated suture fixture 1070 and/or one or more components thereof.

In certain embodiments, the controller 1030 includes one or more processors and/or controller circuitry configured to access suturing script information 1034 or other script/program information maintained by the controller in data storage thereof, or otherwise accessed by the controller 1030. The controller 1034 may include positioning control circuitry 1032 designed to interpret suturing script information or other script/program information and generate control signals for controlling the automated suture fixture 1070 based at least in part thereon.

The suturing script information 1034 or other script/program information may comprise sequential positioning information for one or more components of the automated suture fixture 1070 with respect to one or more suturing processes or other processes that the controller 1030 is designed to implement. For example, in some embodiments, the positioning control circuitry 1032 may be configured to provide position information for each step of a suturing process in a sequential manner. The advancement from one position step to another may be directed by the controller 1030 based on a timer, user input, or other mechanism. For example, user input may be received by the controller 1030 from a user input device 1015, such as a foot pedal or other input device communicatively coupled to the controller 1030. In certain embodiments, input can be provided using (e.g., pressing or clicking) an icon or electronic button on a display that can be clicked on or toggled to provide input to the controller to advance the procedure and/or move the automated fixture (e.g., to the next position). In certain embodiments, input can be provided using voice commands and/or voice recognition software to provide input to the controller to advance the procedure and/or move the automated fixture 1070 (e.g., to the next position).

The automated suture fixture 1070 can include a plurality of motorized actuators 1071, which can be communicatively coupled to the controller 1030. In certain embodiments, the motorized actuators 1071 can be coupled to one another in a daisy-chain configuration, wherein two or more of the motorized actuators 1071 are coupled or wired together in sequence.

Each of the motorized actuators 1071 can include a motor, such as a DC, AC, or brushless DC motor. The motor can be a servo motor. In certain embodiments, the motor 1072 is controlled using pulse-coded modulation (PCM), as directed by the motor control circuitry 1076. For example, the motor control circuitry 1076 can apply a pulse application for a certain period of time, wherein the angular positioning of a rotor component 1073 is determined at least in part by the length of the pulses. The amount of power applied to the motor 1072 may be proportional to the rotational distance of the rotor 1073.

In certain embodiments, the motorized actuators 1071 can be servo actuator devices including one or more servo feedback component(s) 1074, such as a position sensor (e.g., a digital encoder, magnetic encoder, laser(s), etc.). Use of servo feedback component(s) 1074 may be desirable in order to achieve a desirable level of confidence that the motorized actuators 1071 are positioned as directed by the controller 1030 with an acceptable degree of accuracy. The servo feedback component(s) 1074 may provide an analog signal to the motor control circuitry 1076 indicating a position and/or speed of the rotor 1073, which may advantageously allow for relatively precise control of position for faster achievement of a stable and accurate rotor position. Relatively accurate positioning of an implant device may be necessary or desirable due at least in part to the dimensions of the cloth of a heart valve or other implant device that is sutured in an implant suturing operation using the automated suture fixture 1070. For example, the fabric being sutured may comprise woven strands forming ribs having relatively small gaps therebetween. In certain embodiments, the automated suture fixture 1070 may be required to articulate a suture target prosthetic human implant device within 0.2 mm accuracy, or less. Although servo motor devices and components are described herein in the context of certain embodiments, in certain embodiments, one or more motorized actuators 1071 comprise stepper motors, or other types of motor subsystems.

The motorized actuators 1071 can further comprise motor control circuitry 1076, which can drive the motor 1072 according to the control signals received from the controller 1030. In certain embodiments, the motor 1072, in combination with the servo feedback mechanism 1074 and/or motor control circuitry 1076, can advantageously be configured to retain the rotor 1073 and/or attached support member in a set position for desired periods of time. The motor 1072 can provide relatively smooth commutation and/or accurate positioning of the associated rotor 1073. The motor 1072 can be relatively powerful relative to its size, and may draw power proportional to the mechanical load present on the rotor 1073 and/or associated support member.

In certain embodiments, the servo feedback component 1074 comprises a potentiometer that is connected to the rotor 1073, which may be considered the output device of the motorized actuator 1071. The rotor 1073 can link to the potentiometer and control circuitry 1076, wherein the potentiometer, coupled with signals from the control circuitry, controls the angle of the rotor 1073 (and associated support member) across a rotational range, such as between 0°-180°, or further. In certain embodiments, the rotational range of the rotor 1073 may be restricted by one or more mechanical stops, which may be built into associated gear mechanism(s). The potentiometer (or other servo mechanism, such as an internal rotary encoder) may allow the control circuitry 1076 to monitor the current angle of the motor 1072 and/or rotor 1073. When the rotor 1073 is at the correct or targeted angle or position, the motor 1072 may idle or lock in place until the next positioning signal is received from the controller 1030.

The automated suture fixture 1070 can further include a suture target holder device or assembly 1080 (although called a suture target holder or assembly herein, this can be another type of target holder device or assembly to hold target devices/components for other procedures). The suture target holder 1080 can be physically coupled to one of the motorized actuators 1071, such as to distal extension arm actuator device of the plurality of actuators. The suture target holder 1080 can be configured to hold or have mounted thereto a prosthetic heart valve device, or other prosthetic human implant device, which is desired to be sutured. The suture target holder 1080 can have any suitable or desirable shape, configuration and/or dimensions and may be configured to hold or otherwise secure a target device or implant device in a variety of different ways. Example embodiments of suture target holder devices and assemblies are described in detail below in connection with FIGS. 12-15 and 31. However, it should be understood that such embodiments are provided as examples only, and other types of suture target holders can be implemented in the system 1000. In certain embodiments, the distal motorized actuator includes a rotating support member configured to rotate about a first rotational axis. In some embodiments, the suture target holder is coupled to the support member of the distal motorized actuator and configured to rotate about an axis that is parallel to the first rotational axis of the support member. In some embodiments, the suture target holder is coupled to the support member of the distal motorized actuator and configured to rotate about an axis that is orthogonal to the first rotational axis of the support member.

Figure 11:
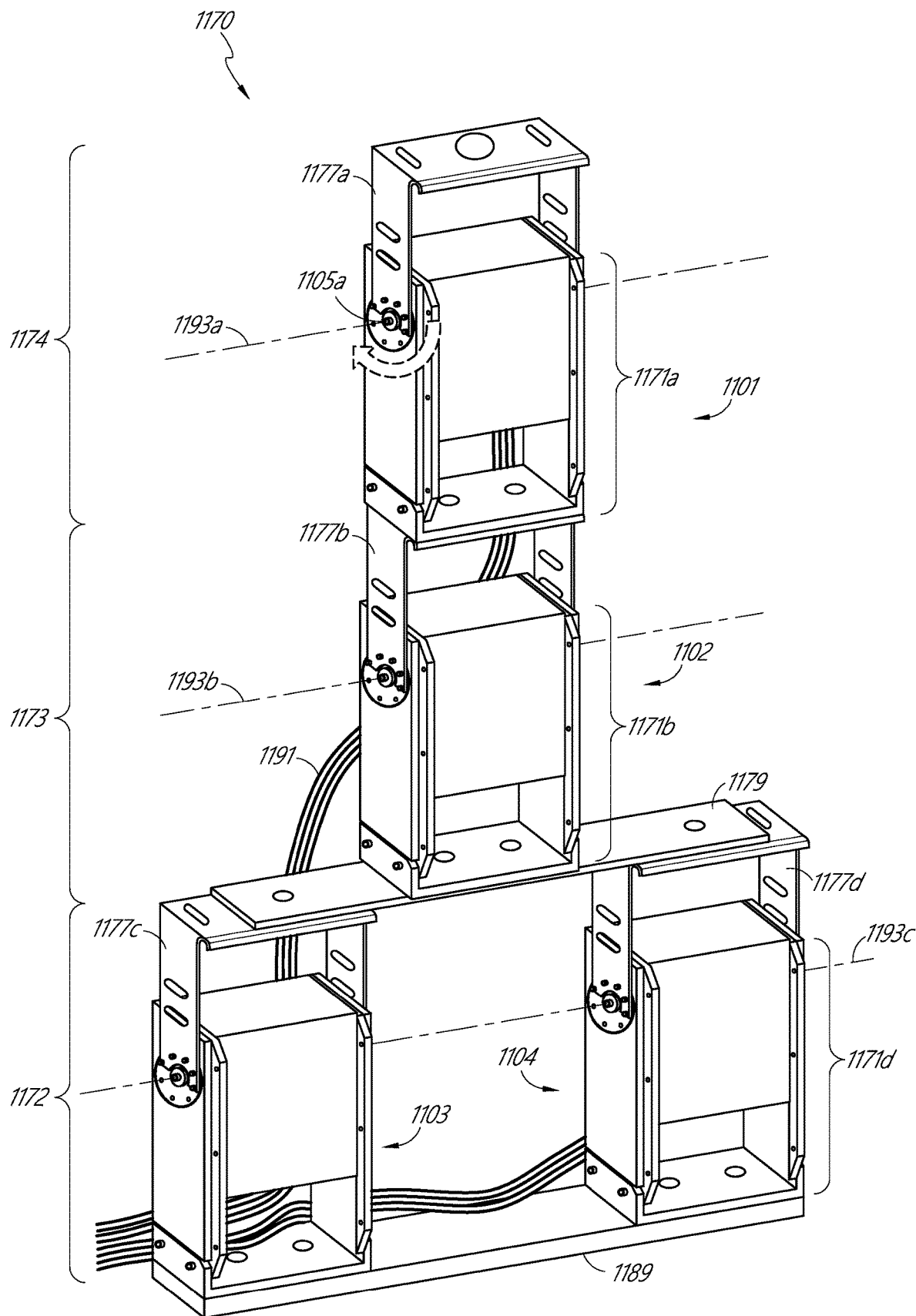
FIG. 11 illustrates a perspective view of an automated suture fixture in accordance with one or more embodiments.

FIG. 11 illustrates a perspective view of an exemplary embodiment of an automated suture fixture 1170 in accordance with one or more embodiments. The automated suture fixture 1170 includes a plurality of motorized actuators 1101, 1102, 1103, and 1104. The motorized actuators 1101-1104 can be physically and/or communicatively coupled in a desired configuration to provide a targeted range of motion and positioning for a distal actuator 1101 (referred to herein in certain contexts as a distal articulation arm) suitable for presenting a suturing target device to an operator in accordance with embodiments of the present disclosure. While four motorized actuators are shown (i.e., 1101-1104), additional motorized actuators and/or other actuators could be used to provide more degrees/types of movement and/or different types of movement (e.g., linear movement, movement in other patterns, etc.). FIGS. 18-25 and 28-30 illustrate exemplary configurations of automated fixtures that include different arrangements of motorized actuators. The automated fixtures described herein with reference to these figures can move up and down to different heights and articulate in additional directions, including horizontal directions.

An end or distal actuator can hold or comprise (or be modified to hold or comprise) a holder device or assembly (e.g., a holder device or assembly described herein with reference to FIGS. 12-15, and/or 18-31) and/or target device (e.g., valve). For example, the automated fixture shown in FIGS. 18-25 and 28-30 (and other automated fixtures described or shown herein) can be modified to include, at an end thereof, the holder assembly/device shown in FIGS. 26, 27 and/or 31. In some embodiments, bags can be configured to at least partially cover linkages from ingress.

With reference to FIG. 11, each of the motorized actuators 1101-1104 can comprise a base portion 1171 and a rotating support member 1177 mechanically fixed to a rotor component 1105. In certain embodiments, the rotor component 1105 is associated with a magnetic motor (not shown), wherein rotation of the rotor component 1105 is caused by the interaction between conductive windings and magnetic fields designed to produce a torque around the rotor's axis (e.g., 1193*a*, 1193*b*, 1193*c*, respectively). The motor may utilize a set of gears to rotate the output rotor and a potentiometer at the same time. The potentiometer, which may at least partially control the angle of the servo motor, may allow the control circuitry (not shown) to monitor the current angle of the servo motor. The motor, through a series of gears, can be configured to turn the output rotor and the potentiometer simultaneously. The potentiometer feedback signal may be fed into the servo control circuit, wherein when the control circuit detects that the position is correct, it stops the servo motor. If the control circuit detects that the angle is not correct, it can continue to turn the servo motor the correct direction until the angle is correct. While rotating actuators are described, actuators that move linearly can also be used (e.g., to raise and lower or move in and out a portion of the fixture).

In certain embodiments, the automated suture fixture 1170 includes a plurality of stages. For example, as shown, the fixture 1170 may comprise a base stage 1172 that includes motorized actuators 1103, 1104. In the illustrated embodiment, the base stage 1172 includes two separate actuators (1103, 1104) that provide base support for the fixture 1170 but it is to be understood that the number of motorized actuators can be any suitable number such as one, two, three, four, five, or more than five. In some embodiments, the actuators 1103, 1104 of the base stage 1172 can be secured mechanically to one another in any suitable or desirable way. For example, as shown, the actuators 1103, 1104 can each be mounted to a common reference structure, such as an attachment plate 1189, or other structure. Each of the actuators 1103, 1104 can comprise a rotating support member (1177*c*, 1177*d*) configured to rotate about a common rotational axis 1193*c*, as shown.

The automated suture fixture 1170 includes a second stage 1173, which can comprise one or more motorized actuators. For example, as shown, the stage 1173 can comprise a single actuator device 1102 in some embodiments. The base portion 1171*b* of the actuator 1102 can be fixed or secured to one or advantageously both of the rotating support members of the base stage actuators 1103, 1104, as shown. Where the base actuators 1103, 1104, are separated horizontally from one another by a certain distance, it may be desirable to use a support plate or structure 1179 for fixing the support members of the base stage actuators 1103, 1104 to one another, wherein the second stage actuator 1102 is fixed to the support plate 1179. That is, the support plate 1179 can be secured or fixed, such as through the use of one or more bolts, screws, nuts, and/or the like, to both of the support members of the base stage 1172, and further secured or fixed to the base of the second-stage actuator 1102 through any suitable or desirable means.

The second-stage actuator 1102 may further comprise a rotating support member 1177*b* configured to rotate about the rotor axis 1193*b*. Therefore, the second stage actuator 1102 can provide an additional degree of movement of the automated suture fixture 1170 when combined with the base-stage actuators in the attachment configuration illustrated. The automated suture fixture 1170 may yet provide an additional degree of movement through implementation of the distal actuator 1101 illustrated. Although a third stage 1174 is shown in the diagram of FIG. 11, it should be understood that in certain embodiments the fixture 1170 can include only the base stage 1172 and the second stage 1173. Furthermore, although the illustrated embodiment comprises three stages, it should be understood that embodiments disclosed herein may be implemented using automated suture fixture assemblies having more than three stages (e.g., 4, 5, 6, 7, 8 or more stages) and/or having more than four motorized actuator devices (e.g., 5, 6, 7, 8, 9, or more actuator devices).

The distal third-stage actuator 1101 may be fixed or secured at a base 1171*a* thereof to the rotating support member 1177*b* of the second-stage actuator 1102, as shown. Furthermore, the distal actuator 1101 may further comprise a rotating support member 1177*a*, which may be configured to rotate to provide yet another degree of movement for the fixture 1170. In certain embodiments, the distal actuator 1101 may have attached thereto (e.g., at the rotating support member 1077*a*) a suture target holder assembly or target holder assembly in accordance with embodiments of the present disclosure.

The automated fixture 1170 is illustrated in the diagram of FIG. 11 in a substantially erect arrangement, in which the respective support members are positioned in a vertical arrangement, such that the rotational axes of the respective actuator devices lie substantially in a single vertical plane. However, the additional degrees of movement provided by the fixture 1170 may allow for rotation of the various support members, such that the axes of rotation of the respective rotors of the second- and third-stage actuator devices may ultimately lie in separate vertical planes from the rotational axis of the support members 1177*c*, 1177*d* of the base-stage actuator devices 1103, 1104.

The various motorized actuator devices of the automated suture fixture 1170 can be controlled in any suitable or desirable way. For example, in some embodiments, the various motorized actuator devices of the fixture 1170 can be configured to receive wireless control signals over a wireless connection with a control system, device or module, such as the controller 1030 of FIG. 10 described above, or the like. In some embodiments, the actuators can be configured to receive wired control signals, such as over the various wired connections 1191 illustrated. For example, certain embodiments, two or more of the stages and/or actuator devices of the fixture 1170 can be communicatively coupled using a wired connection in a daisy-chain configuration, as described herein.

FIGS. 18-25 illustrate another example embodiment of an automated suture fixture 1970. The automated suture fixture 1970 includes an articulating arm 1978 having a plurality of actuator devices 1973A-1973D daisy chained together to provide movement of a distal target mount point 1971. The distal target mount point 1971 can be configured to secure a suture target holder device or assembly such as those illustrated in FIGS. 26, 27, and 31. The suture target holder can be physically coupled to the distal target mount point 1971 or it can be integrally formed as part of the distal target mount point 1971. The suture target holder can be configured to hold or have mounted thereto a prosthetic heart valve device, or other prosthetic human implant device, which is desired to be sutured.

The automated suture fixture 1970 also includes a vertical translation stage 1972 configured to vertically move the articulation arm 1978. This further increases the range of movement of the automated suture fixture 1970 while maintaining a desirably small footprint. The vertical translation stage 1972 includes a piston configuration that attaches to the proximal actuator device 1973A so that the vertical translation stage 1972 can cause the entire articulation arm 1978 to raise and lower. It is to be understood that the vertical translation stage 1972 can be configured to not be exactly vertical and can be tilted or angled away from perfectly vertical.

The automated suture fixture 1970 can include a base plate 1979 to support the vertical translation stage 1972 and to define a workspace for manufacturing the target device. In certain embodiments, the working zone for the fixture 1970 may be approximately 6.75" high (e.g., the articulation arm 1978 can translate about 6.75" vertically or at least 4" and/or less than or equal to about 10"). In some embodiments, the height of the vertical translation stage 1972, H, is about 26" or at least about 20" and/or less than or equal to about 36", at least about 22" and/or less than or equal to about 30", or at least about 24" and/or less than or equal to about 28". In some embodiments, the depth of the base plate 1979, D, is about 18" or at least about 12" and/or less than or equal to about 24", at least about 14" and/or less than or equal to about 22", or at least about 16" and/or less than or equal to about 20". In some embodiments, the length of the base plate 1979, L, is about 20" or at least about 12" and/or less than or equal to about 30", at least about 15" and/or less than or equal to about 26", or at least about 18" and/or less than or equal to about 24".

With respect to FIGS. 19 and 20, the illustrated positions of the fixture 1970 may correspond to a bottom of a stroke of the vertical translation stage 1972 in a z-direction. In certain embodiments, the distal target mount point 1971 can be configured to tilt approximately 54 degrees upward. With respect to FIGS. 21 and 22, the fixture 1970 can change the position and orientation of the distal target mount point 1971 while at the bottom of the stroke of the vertical translation stage 1972. This is done by actuating the articulation arm 1978.

With respect to FIGS. 23 and 24, the illustrated positions of the fixture 1970 may correspond to a top of a stroke of the vertical translation stage 1972 in the z-direction. In certain embodiments, the distal target mount point 1971 can be configured to tilt approximately 15 degrees down from horizontal. With respect to FIG. 25, the illustrated position of the fixture may represent an approximately 45-degree downward tilt for implementing a "dipping" step.

Figure 28:
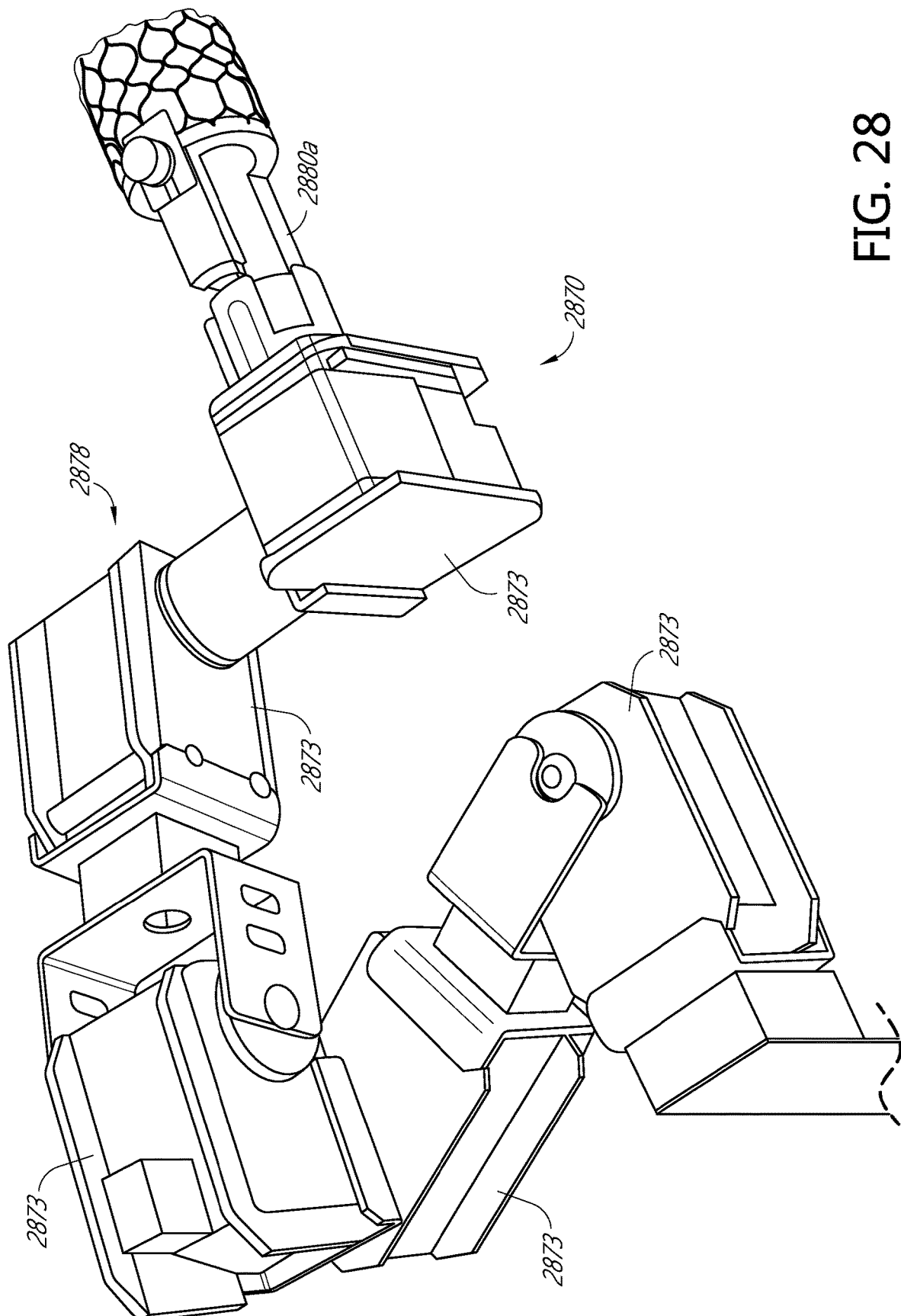
FIGS. 28 and 29 illustrate another example automated suture fixture having a different configuration for an articulation arm that includes a plurality of actuator devices that are oriented to provide additional vertical support.
Figure 29:
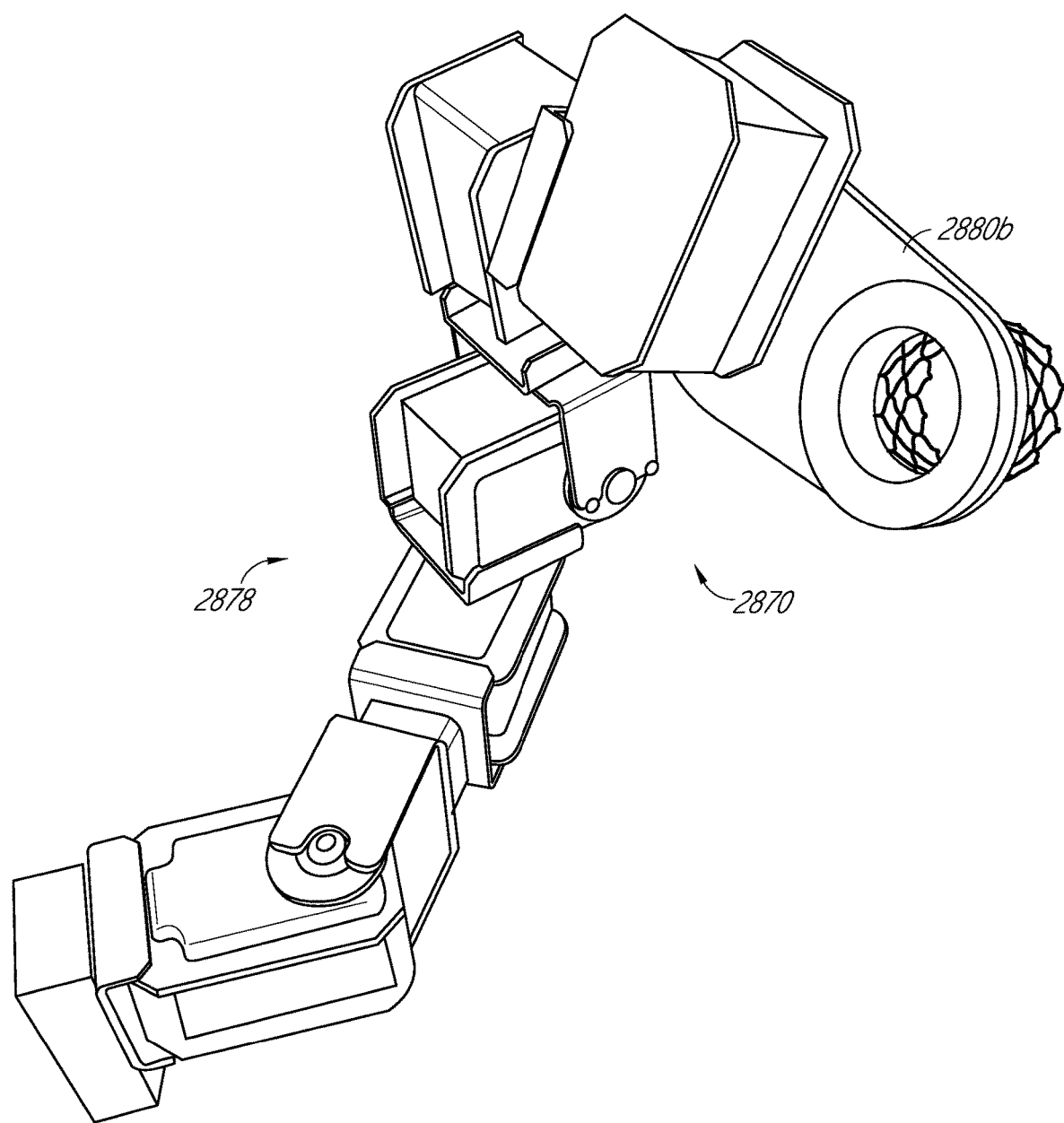

FIGS. 28 and 29 illustrate another example automated suture fixture 2870 having a different configuration for an articulation arm 2878. The fixture 2870 includes a plurality of actuator devices 2873 that are oriented to provide additional vertical support. By orienting rotors so that the axis of rotation is substantially vertical, the support members can provide additional support against downward forces as opposed to relying on the motor to resist downward forces. This may be of increased importance closer to the proximal end of the articulation arm due to the increase in torque the further from the pivot point a force is applied (e.g., a downward force at a distal end of the articulation arm 2878 can cause more torque at the proximal end than at the distal end). The automated suture fixture 2870 can be coupled to different target holders 2880*a* and 2880*b*, respectively illustrated in FIGS. 28 and 29. The target holder 2880a is similar to the target holder 3180 described herein with reference to FIG. 31.

Figure 30:
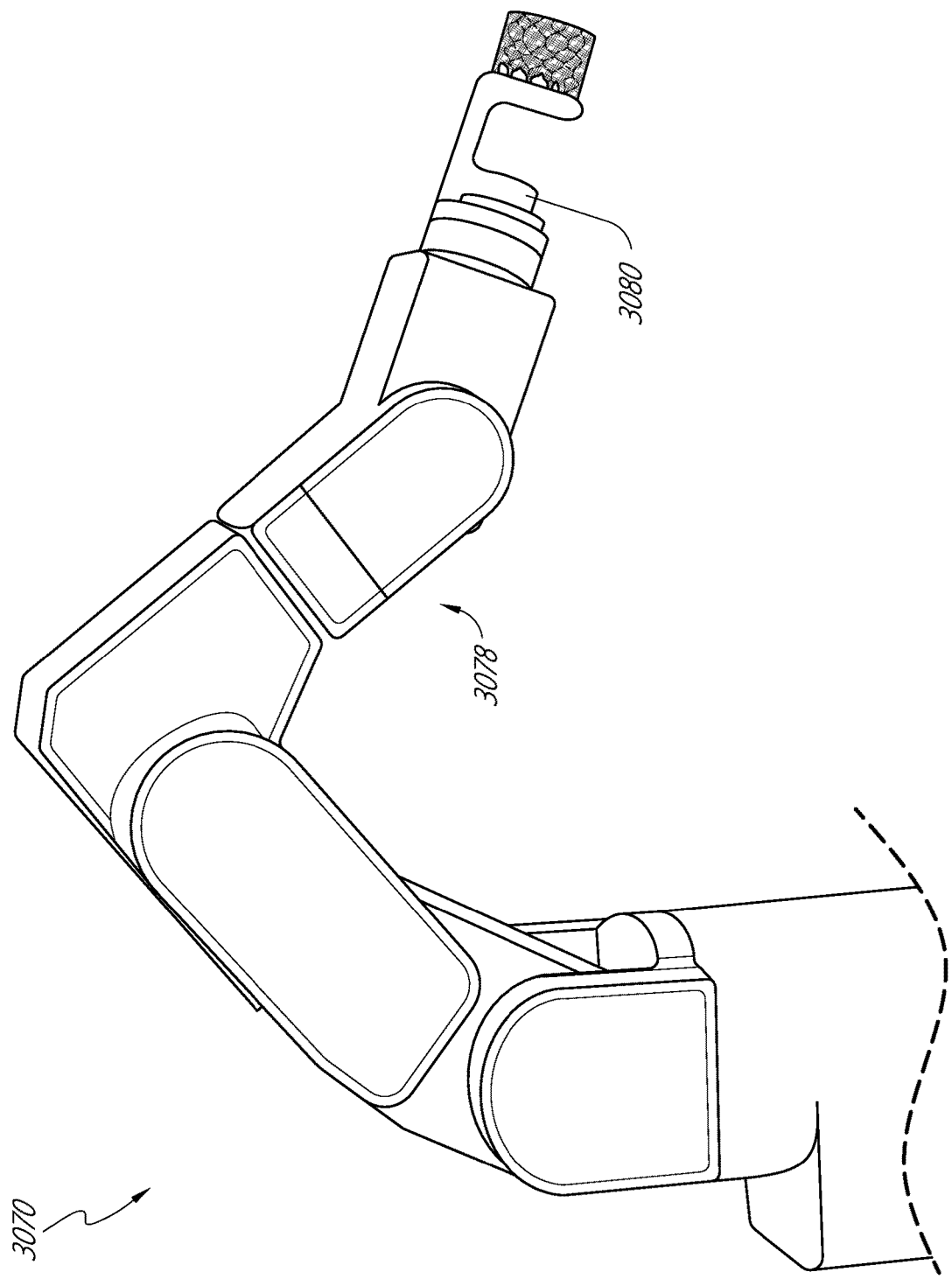
FIG. 30 illustrates another example automated suture fixture having a different configuration for an articulation arm.

FIG. 30 illustrates another example automated suture fixture 3070 having a different configuration for an articulation arm 3078. The articulation arm 3078 has a crane-like configuration and is configured to substantially enclose the actuation devices within a housing or a plurality of housings. The articulation arm 3078 secures a target assembly 3080 that is similar to the target assembly 3180 described herein with reference to FIG. 31.

Suture Target Holder

Figure 12:
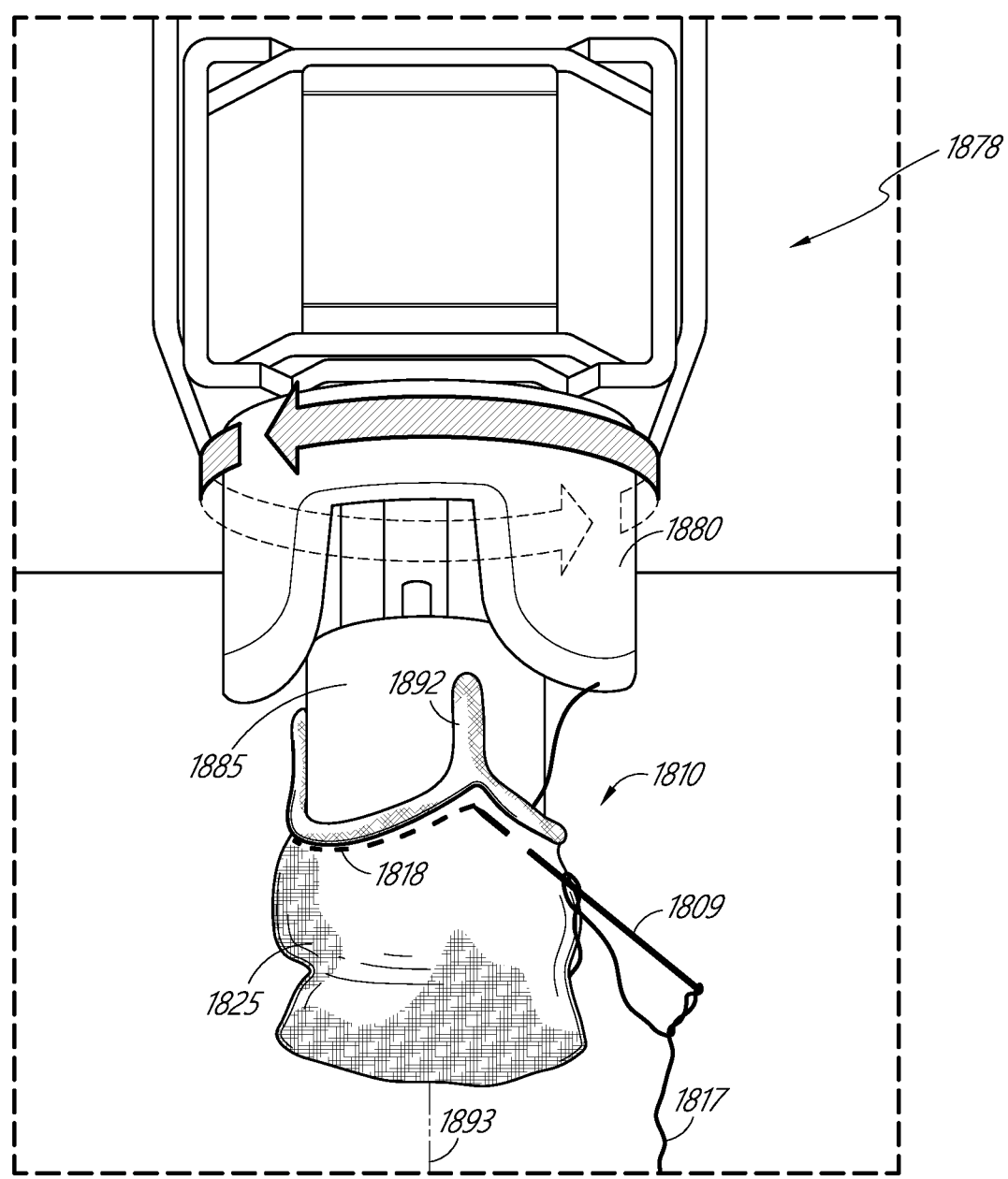
FIG. 12 illustrates a distal articulation arm of an automated suture fixture coupled to a holder component in accordance with one or more embodiments.

FIG. 12 illustrates an articulation arm 1878 coupled to an exemplary holder component 1880 according to one or more embodiments. The articulation arm 1878 can be the same as or similar to the articulation arms 778, 878 described herein with reference to FIG. 7A, 7B, 8A, 8B, or 8C and/or one or more actuators described or shown elsewhere herein. The holder component 1880 can be the same as or similar to other target holder components, devices, or assemblies (e.g., 771, 880, 1080, 1180, 1380) described elsewhere herein. In certain embodiments, the holder component 1880 can be fixed or secured to the distal articulation arm 1878 or end actuator of an automated suture fixture for the purpose of providing an interface for securing an implant device or other target form or device. The holder component/assembly 1880 can be designed or configured to hold or secure an implant device or other target device, or portion thereof, for the purpose of allowing suturing thereof according to any process or embodiment disclosed herein.

The holder component 1880 can be configured to secure or otherwise include a cylinder form 1885, which can be sized or dimensioned to have pulled thereover the target device or implant (e.g., a fabric-covered support stent for a surgical valve implant device 1818). For example, the valve implant device 1818 may comprise a plurality of commissure post portions 1892, as shown, which may be positioned such that they are oriented in a direction towards the holder component 1880, such that a seam 1818 may be stitched above what will ultimately represent an inflow edge of the implant device 1818. The cylindrical form/component 1885 may be designed in a similar manner to a handheld implant device holder, which may be used in certain embodiments in executing suturing procedures without the assistance of the articulation arm 1878 and associated components. The cloth 1825 can be disposed about a rigid wireframe structure, wherein the seam of stitches 1818 is executed in order to substantially cover the wireframe with the cloth 1825. The seam 1818 can secure the cloth 1825 about a stiffening band, as described herein with reference to FIG. 3A.

The holder component 1880 can be designed for a particular application, such as for a transcatheter heart valve suturing application, or a surgical heart valve suturing operation, or other implant suturing procedure. The valves can be for animal (e.g., for human) use. Although a surgical valve configuration is shown in FIG. 12, it should be understood that the holder device 1880 and/or other components of FIG. 12 may be designed or configured to support suturing processes and/or other processes for a transcatheter heart valve or other valve or other device. For example, while the diagram of FIG. 12 illustrates a cylindrical form 1885 designed to hold the implant device 1818 in a desired position, such cylindrical form may not be necessary with respect to a transcatheter heart valve. For example, in place of the cylindrical form 1885, the holder 1880 can instead be configured to secure a rigid cylindrical wireframe of a transcatheter heart valve, an embodiment of which is illustrated and described above in connection with FIG. 1.

With the target or implant device 1818 secured to the holder device 1880, an operator may conveniently be able to execute stitching operations using, for example, a needle 1809 and thread 1817. For example, the system can facilitate or make it easier for an operator to perform exterior circumferential stitching operations (e.g., with respect to surgical heart valves), interior-to exterior stiches, and/or exterior-to-interior stitches (e.g., for certain transcatheter heart valve stitching operations). The holder device 1880 and/or associated components can be designed to efficiently allow for the target or implant device 1818 be presented to the operator such that multiple degrees of freedom are available for the operator and articulation arm 1878 to further simplify and assist with suturing or other procedures.

In certain embodiments, the holder component 1880 and/or one or more components associated with the holder component 1880 (e.g., the cylinder form, etc.) can be configured to rotate about a central or longitudinal axis 1893 thereof. Central axis 1893 can represent a central axis of the target or implant device 1810, cylinder 1885, and/or other portion of the holder component 1880 (e.g., when the device 1810, cylinder 1885, and/or other component is connected or mounted to the holder component 1880). The rotation of the holder component 1880 and/or components associated therewith may allow for presentation of different surface areas of the target or implant device 1810 to the operator during different stages of a suturing procedure or other procedure.

The specific type of holder that is utilized for a procedure or application (e.g., for a suture assist application) may be determined on a process-by-process basis. That is, specific adapters may be suitable or desirable for each of separate operations/procedures, or for separate types of valves or other targets. In certain embodiments, a single suturing procedure of an implant device can involve use of multiple different types of holder devices.

Figure 13:
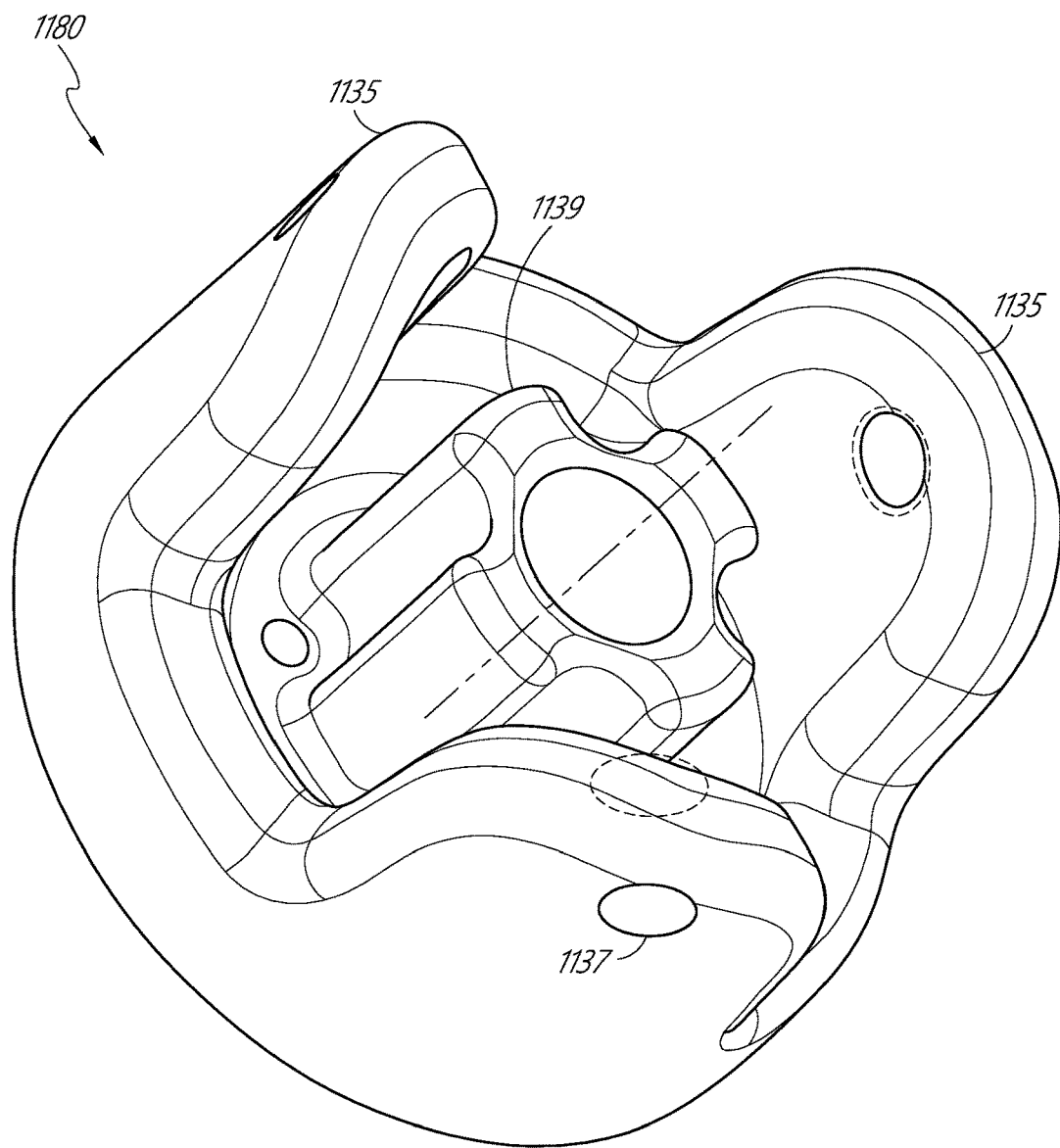
FIG. 13 illustrates a holder device in accordance with one or more embodiments.

FIG. 13 illustrates an exemplary holder component/device 1180 in accordance with one or more embodiments disclosed herein. For example, the holder device 1180 may be the same as or similar in certain respects to the holder device 1880 described herein with reference to FIG. 12 and/or other holder devices, components, assemblies, etc. (e.g., 771, 880, 1080, 1380) described elsewhere herein. The holder component 1180 can comprise one or more features or components designed to allow for a cylindrical holder and/or component of a target or implant device to be secured thereto. For example, the holder 1180 may allow for securing of a cylindrical holder and/or component of the implant device in such a manner as to provide radial symmetry for precise positioning thereof. In certain embodiments, the holder 1180 comprises a plurality of jaw or clamp forms 1135, which may be arranged in a radially symmetrical pattern about a circumference of the holder 1180. The jaws 1135 may be configured to be tightened to hold the cylindrical holder and/or target or implant device component or may comprise one or more other mechanisms for securing the cylindrical holder and/or target or implant device about a central hub component 1139. For example, the jaw forms 1135 may comprise one or more apertures for utilizing set screws therein, which may be configured to grip or secure the cylindrical holder and/or target or implant device component.

Figure 14:
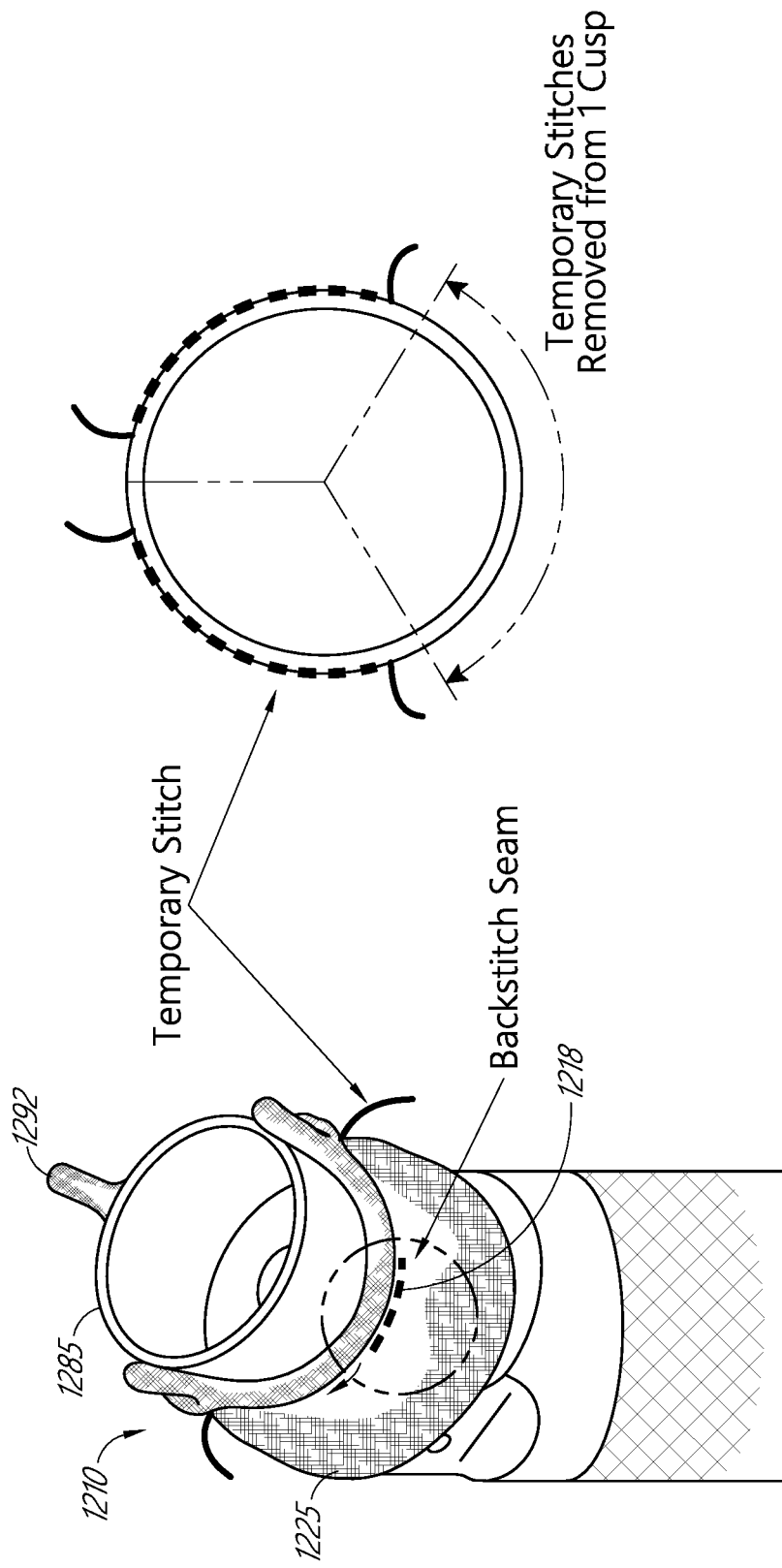
FIG. 14 illustrates an implant device disposed about a holder component in accordance with one or more embodiments.

FIG. 14 illustrates an implant device fit about a cylindrical holder 1285, the implant device comprising a plurality of commissure posts 1292 formed of a frame (e.g., a wireframe) (not shown), wherein the frame or wireframe is at least partially covered by a cloth 1225, the cloth 1225 being sutured to secure the cloth 1225 about the frame structure of the implant device 1210. FIG. 14 illustrates an exemplary back stitched seam 1218 that can be implemented to secure the cloth 1225 about the support structure, but other types of stiches and seams could also or alternatively be used. Although wireframes are described in detail and used as examples of frames herein in connection with certain surgical valves, it should be understood that any type of stiffening or support frame forms or components may be utilized, e.g., to provide the described commissure posts and/or stiffening bands associated with certain surgical valve devices. For example, one or more plastic bands, metal bands, or other stiffening or rigid support structures can be used to form the, sure posts and/or stiffening band of a surgical valve. As shown in FIG. 14, suturing of certain implant devices may involve utilizing temporary stitches that can be removed upon completion of certain stitched seams or other suturing operations.

Gimbal Mount Holder

Figure 15:
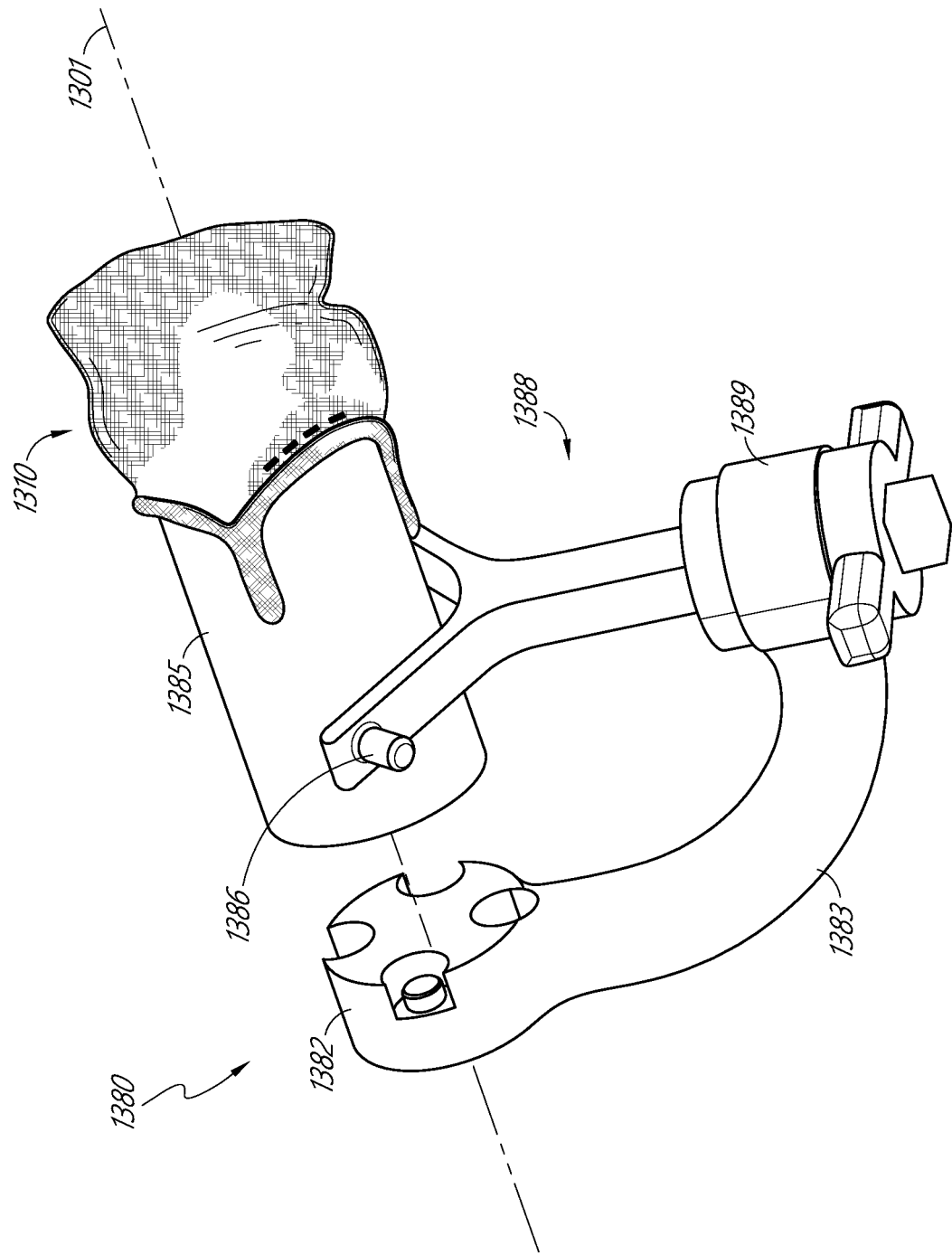
FIG. 15 illustrates a gimbal-type holder assembly in accordance with one or more embodiments.

Certain embodiments disclosed herein provide for holding and/or positioning of an implant device that is the subject of a suturing procedure using a gimbal-type holder assembly 1380, as shown in FIG. 15. Further, the automated fixture, articulation arm, and/or various actuators of the automated fixture can also or alternatively be configured to function similar to a gimbal. While certain embodiments of implant device holder components as disclosed herein may generally present one end of the implant device and/or circumferential surfaces or features of the device to the operator, certain of such embodiments may not allow for free operation by the operator about both front and back ends of the implant device and/or holder device. For example, one end of the implant or holder device may be secured at least in part to a component of an articulation arm and/or other holder device. The valve holder device of FIG. 15 and/or other portions of the automated fixture can provide a mount that allows for operational access at multiple ends of an implant device, and may essentially be configurable to float or rotate to the proper position for manufacturing, thereby relieving the operator of the burden of removing the implant device from the holder and rotating and re-securing the implant device in order to have access to both ends of the implant device during a suturing procedure or other procedure.

The gimbal assembly 1380 and/or other gimbal-like arrangements of an automated fixture can be configured to articulate a heart valve or other target or implant device to substantially any desired orientation for ease of access and use for an operator. For example, the gimbal assembly 1380 can comprise a three-axis gimbal allowing for three degrees of freedom. Furthermore, where the gimbal assembly 1380 is mounted to an articulation arm and/or device, additional degrees of freedom may be provided. For example, the combination of the gimbal assembly 1380 with the associated automated suture fixture can provide six degrees of freedom of manipulation. In certain embodiments, the gimbal assembly 1380 may be a two-axis gimbal.

When having secured thereto a target or implant device, such as a transcatheter heart valve or surgical valve implant device, the gimbal assembly 1380 and/or other gimbal-like arrangement of an automated fixture can be configured to position the target or implant device accurately in multiple orientations. For example, the gimbal assembly 1380 can be configured to execute circumferential rotation of a heart valve, while maintaining the outer surface (or a desired portion of the outer surface) of the target or implant device or valve within a focal plane or depth of field of an associated camera and/or magnification system.

The gimbal assembly 1380 includes a cylindrical implant holder 1385 having disposed thereon a surgical implant device 1310, which may represent a suturing target implant in accordance with certain embodiments. However, although a cylindrical implant holding form 1385 is illustrated in FIG. 15, it should be understood that, in certain embodiments, the gimbal assembly 1380 may not include the cylindrical implant holding form 1385, and can instead be configured to hold a different holder component (e.g., a rigid cylindrical or otherwise-shaped component) or to directly hold a heart valve or other target or implant device or portion thereof, such as a cylindrical wireframe of a transcatheter heart valve as described herein. A different holder component or target or implant device could be held where the cylindrical holder 1385 is shown. For purposes of discussion, the illustrated component or cylinder 1385 may be referred to below as a holder component and/or as the target or implant device (or valve) itself, indicating that the target or implant device to be sutured, or otherwise engaged, can be disposed and/or secured in the same position shown by the disposition of the cylinder 1385 in FIG. 15. Descriptions of the component 1385 apply to any holder or target device held in the position of component 1385, regardless of whether it is referred to as a component, device, holder, valve, etc. in the description.

Rotation of the target or implant device or valve 1385 may be implemented by rotating a hub component 1382, which can be attached or associated with a rotating servo head of an articulation arm or actuator (not shown in FIG. 15), wherein the hub component 1382 can be associated with an arm component 1383 that allows for rotation of the target or implant device or valve 1385 about a central or rotational axis 1301 of the hub component 1382 and the target or implant device 1385. That is, where the target or implant device or valve 1385 is connected to the arm 1383 via a connector form 1388, such as a Y-connector form, it may be desirable for the connector form 1388 to be adjusted such that the central or longitudinal axis of the target or implant device is aligned or substantially aligned with the rotational axis 1301 of the hub component 1382. When the target or implant device 1385 and the hub component 1382 are thus aligned, rotation of the hub component may be possible while maintaining coaxial alignment of the target or implant device 1385 with the hub 1382, thereby allowing for consistent presentation of an outer surface or region of the target or implant device 1385 in the depth of field of the associated visualization system (e.g., camera). Therefore, the target or implant device 1385 can be circumferentially rotated without moving the target or implant device, or target suture position thereof, out of focus of the camera system.

The connector form or Y-connector 1388 can be configured to nest in a base portion of the arm 1383, and can further be adjustable and provide an indexing feature to allow for movement in and out of the base component 1389 to thereby allow for precise positioning of the target or implant device 1385. In certain embodiments, the hub component 1382 may be coupled magnetically with an associated articulation arm or actuator of an automated fixture. Optionally, the connector form or Y-connector can be rotatable within the base component 1389 to provide for more degrees of movement and positioning possibilities (e.g., to allow the target device to be flipped toward or away from the hub component 1382 and/or rotated to any angle with respect to the axis 1301. The base component 1389 may include a motor or be a motorized actuator to cause movement or rotate the connector form or Y-connector 1388, e.g., so the system can be programmed or scripted to move automatically to a desired position/rotation for a procedure.

The automated fixtures and/or holders described herein can be configured such that a point (e.g., a centermost point) within a target device can remain fixed/stationary while the target device is rotated or repositioned to expose different portions of the target device for a particular operation/step in a procedure.

While various other multi-axis gimbal devices may not be designed to have manufacturing done to them, the gimbal assembly 1380 shown in FIG. 15 can advantageously provide for precise positioning of the distal end of the connector form or arm 1388 and the target or implant device 1385 in order for manufacturing to be performed thereon. Furthermore, with one or two side points of attachment 1386, multiple degrees of freedom can be presented by the gimbal assembly 1380, thereby providing convenience and ease-of-use for the operator. With the multiple-axis (e.g., three-axis) functionality of the gimbal assembly 1380 or other gimbal arrangement of the automated fixture, the target or implant device can be allowed freedom to move to a wide variety of positions and angles to make it easier for the operator to engage with (e.g., suture, inspect, etc.) the target or implant device or valve and to maneuver fingers or other items at a desired location thereon. The multiple-axis (e.g., three-axis) functionality can also make it easier for an operator to view from one side through to the other side of the target or implant device 1385 without substantial obstruction.

Rotating Mount Holder

Figure 26:
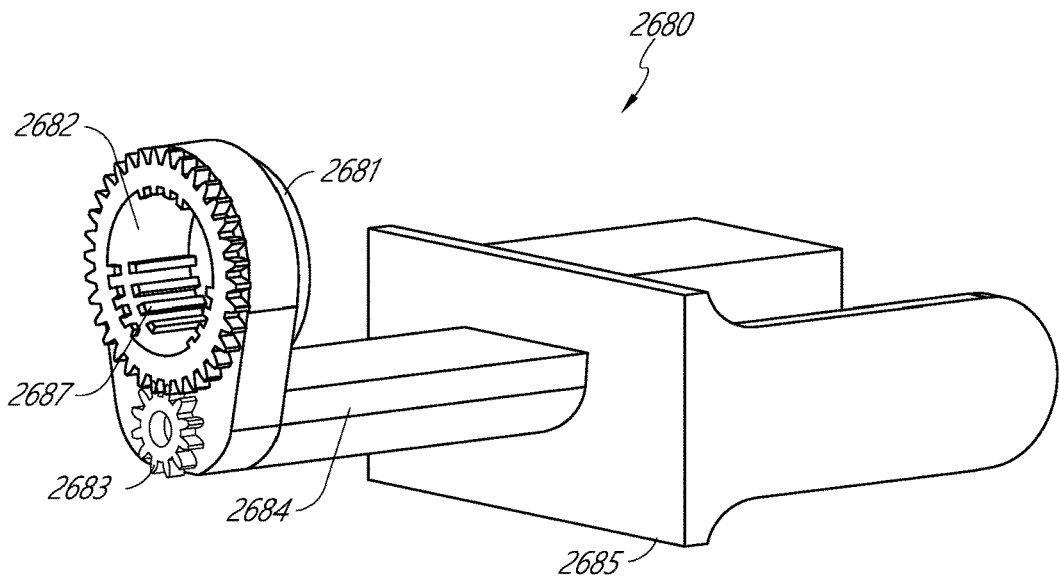
FIG. 26 illustrates a perspective view of a mount or holder device/assembly in accordance with one or more embodiments.

FIG. 26 shows an exemplary mount or holder assembly 2680 that can be used with the assist systems, automated fixtures, gimbal assemblies or arrangements, etc. disclosed herein. The holder device 2680 can be attached or connected to another holder and/or to a motorized actuator (e.g., the same as or similar to those discussed or shown elsewhere herein), e.g., at a proximal end, distal end, back end, end opposite the rotating portion or ring, etc. The holder assembly 2680 can comprise a motor and/or motorized actuator (e.g., a rotational motor/motorized actuator). The holder assembly 2680 can include a portion 2681 or mechanism configured to hold and rotate a target device (e.g., heart valve).

Figure 27:
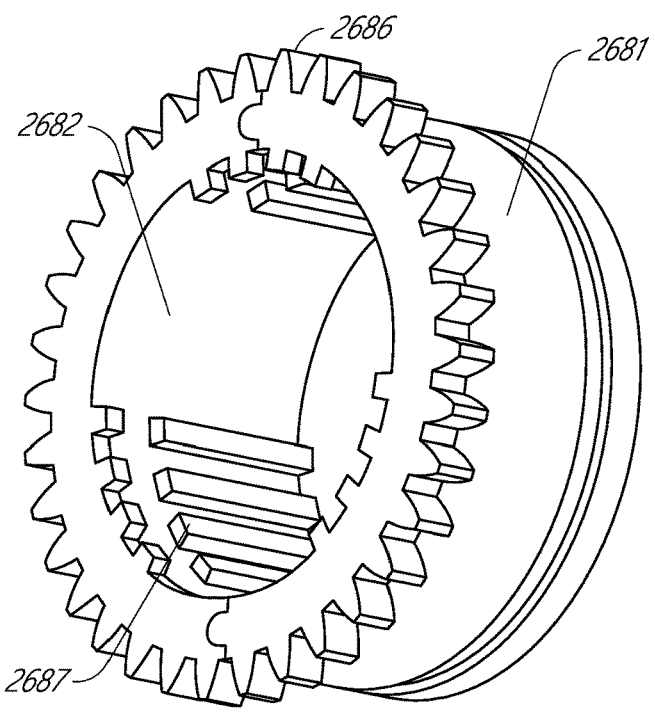
FIG. 27 shows a perspective view of a holder ring that can be used to hold and rotate a target device in accordance with one or more embodiments.

FIG. 27 illustrates an exemplary holder ring 2681 that can be used to hold and to rotate a target device (e.g., a heart valve). The holder ring 2681 can include a geared portion 2686 (e.g., with gear teeth) or other interlocking or friction-engaging portion, etc. that can interact with another gear 2683, interlocking component, friction-engaging component, etc. to cause rotation of the holder ring 2681. The other gear 2683, interlocking component, friction-engaging component, etc. can be connected to a drive shaft (not shown). The drive shaft can connect between a motor and the other gear 2683, interlocking component, friction-engaging component, etc. such that the motor can cause the gear, interlocking component, friction-engaging component, etc. to rotate. Rotation of the gear 2683, interlocking component, friction-engaging component, etc. can cause the holder ring 2681 to rotate.

The holder ring 2681 can include an inner surface 2682 configured to hold and engage the target device. Features 2687 can be included on the inner surface 2682 to improve the hold or better secure the target device. The holder ring 2681 (and/or its inner surface 2682) can be configured to cover only a small surface area of the target device, e.g., to leave portion of the target device to be operated on, treated, sutured, etc. open and unobstructed. Using a rotating holder assembly 2680 allows an automated fixture to rotate a target device without having to rotate the entire holder assembly. This allows the automated fixture to keep the target device (e.g., a portion of the target device or surface thereof) within a depth of field of a visualization system (e.g., a camera) throughout 360-degree rotation of the target device without requiring movement of the visualization system or adjustment of the focus, and without ever having an arm or other portion of the holder assembly 2680 rotate into the visualization system's (e.g., camera's) view.

While an exemplary implementation is shown in FIGS. 26 and 27, other implementations of the concepts described are also possible that may include additional elements or components, different elements or components, or not include some elements or components.

Example Extended Holder Assembly

Figure 31:
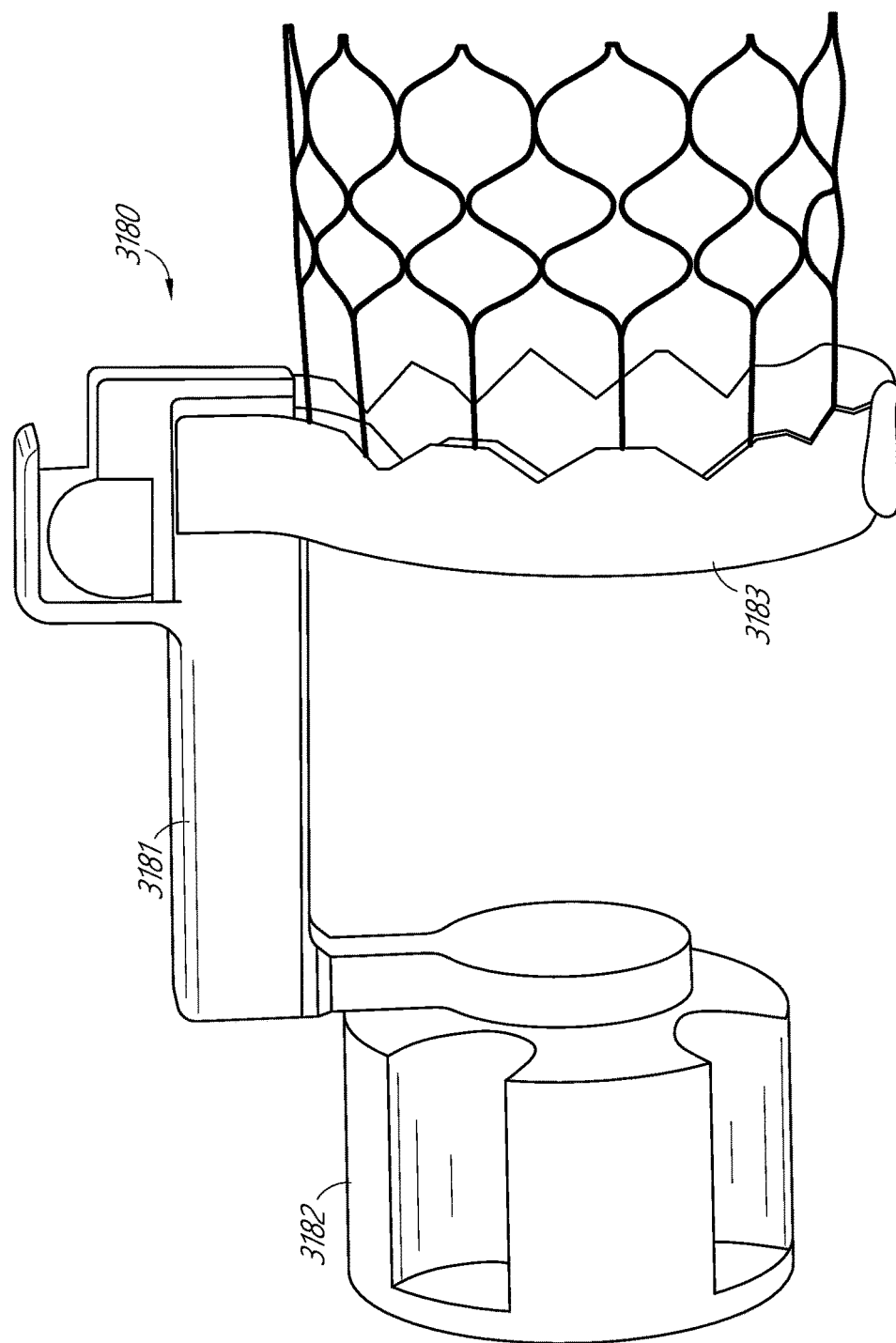
FIG. 31 illustrates another example holder assembly that extends distally from an articulation arm to allow access to an internal portion of a target device from an in-flow or out-flow approach.

FIG. 31 illustrates another example holder assembly 3180 that extends distally from an articulation arm to allow access to an internal portion of a target device (e.g., a valve) from an in-flow or out-flow approach. The holder assembly 3180 includes a support arm 3181 that extends from a base 3182 that couples to an articulation arm, examples of which are described herein. In some embodiments, the articulation arm and/or base 3182 are configured to rotate about a central or longitudinal axis of a cylinder support 3183 of the holder assembly 3180. The cylinder support 3183 is coupled to the support arm 3181 and is configured to secure the target device to the holder assembly 3180 in the same or similar manner as other holder assemblies described herein.

Point-By-Point Suture Assistance

Figure 16:
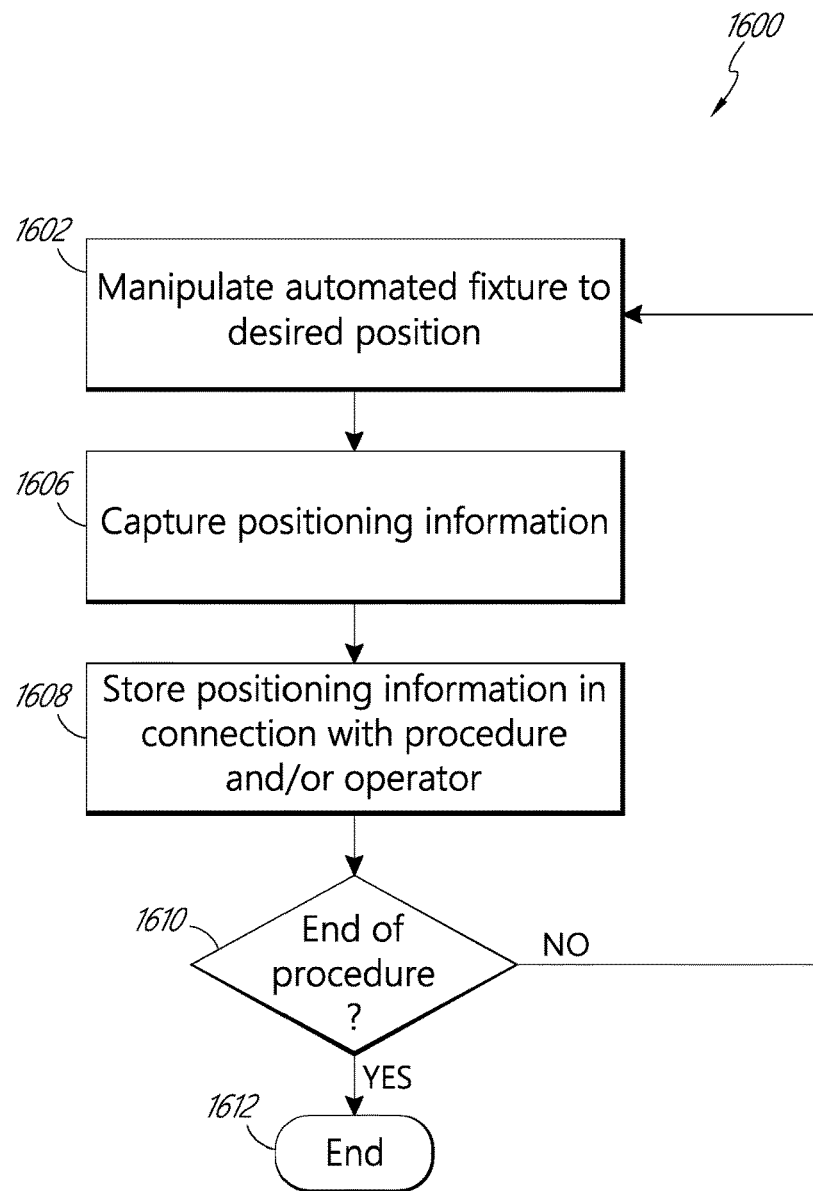
FIG. 16 illustrates a flow diagram illustrating a process for training a suture assist system to implement a suture assist procedure according to one or more embodiments.

Embodiments disclosed herein provide for systems, devices, and methods for providing point-by-point assistance (e.g., point-by-point suture assisting) functionality in connection with procedures (e.g., the suturing of implant devices, inspection, or other procedures). For example, a suture assist system in accordance with the present disclosure may provide point-by-point (e.g., step-by-step) assistance to an operator through the use of one or more of an automated suture fixture, a visualization system (e.g., a microscope and/or magnification system, and/or an image display system), and/or other associated systems, devices, or components. FIG. 16 illustrates a flow diagram of an exemplary process 1600 for training/programming a system to implement and/or facilitate implementation of a particular procedure. For example, the steps in the process 1600 can be used to train/program a suture assist system to implement a suture assist procedure or suturing procedure according to one or more embodiments. The process 1600 may provide a programmable process, wherein a computing system, in combination with hardware systems as disclosed herein, can be configured to read positioning of an automated fixture or automated suture fixture, store position information according to a desired script or program, and/or play the stored script/program back for the purpose of allowing an operator to execute the procedure associated with the script/program. The process 1600 may allow for relatively easy programming of the suture assist procedure script/program through the positioning and/or recording of positioning of an articulation device and/or visualization system (e.g., a microscope or camera system). For example, at block 1602, the process 1600 may involve an operator manipulating an automated fixture or automated suture fixture to a desired position associated with a first step of an implant suturing procedure or other procedure in accordance with the present disclosure. For example, the operator may exert or cause to be exerted torque or other force on one or more portions of the automated fixture or automated suture fixture, such as an articulation arm or distal end portion thereof to bring the distal end into a position associated with a suturing operation or step or other operation or step.

The automated fixture or automated suture fixture may be manipulated and/or repositioned in any suitable or desirable manner. For example, in certain embodiments, the operator may manually manipulate at least a portion of the automated fixture or automated suture fixture, such as an articulation arm thereof, to a desired position. In certain embodiments, manipulation of the automated fixture or automated suture fixture and/or articulation arm thereof may be effected through the use of a control signal, which may be generated using a joystick, buttons, or other operator input device, or through the use of any type of software command/instruction entry or other programming (e.g., using numeric position representation), or the like. In certain embodiments, manipulation of the automated fixture or automated suture fixture may be achieved through the manipulation of a corresponding fixture which may be configured such that movement or manipulation thereof is at least partially mirrored by the automated fixture or automated suture fixture, or wherein the automated fixture or automated suture fixture is configured to be repositioned in response to movement of the mirroring device or system.

In certain embodiments, the process 1600 may involve focusing a visualization system (e.g., a camera or magnification system) to a target position or point associated with the automated fixture or automated suture fixture, such as to a portion of a target or implant device that may be held or secured by the automated fixture or automated suture fixture. However, it should be understood that in certain embodiments, camera focusing may not be required where the process step 1602 involves manipulating the automated fixture or automated suture fixture in order to bring the target position into focus with a stationary visualization system or a camera. That is, the manipulation of the automated fixture or automated suture fixture in step 1602 can involve proper placement of the target implant device, or target portion thereof, into the focal plane of the camera or magnification system, as desired.

At block 1606, the process 1600 can involve capturing the position information associated with the manipulated automated fixture or automated suture fixture, or portion thereof, as executed in accordance with process step 1602. For example, capturing the position information may involve saving one or more values or data representative of a position of the automated fixture or automated suture fixture and/or portion thereof, and/or positioning or focusing of the visualization system (e.g., camera or magnification system).

At block 1608, the process 1600 can involve storing the positioning information in connection with the procedure associated with the position of the automated fixture or automated suture fixture. The position information may be stored along with or be associated/correlated with additional metadata indicating various parameters associated with the position information, such as operator information, patient information, timing information, or the like. The additional metadata or other information can be stored, associated, or applied to the script at the time the positioning information is stored in step 1608. Also, the script can be stored without the additional metadata or other information in step 1608, and the additional metadata or other information can optionally be applied to the script at a later time, e.g., to customize the script for different operator, for example to allow adjustment of the script positioning to accommodate operators of different sizes/heights or other characteristics (e.g., to flip the script positioning for left vs. right handed operators).

At decision block 1610, the process 1600 may involve determining whether additional steps of the procedure remain to be programmed, or whether the position programmed in the preceding steps represents a final position or whether the set of positions programmed previously represent a full set of steps of the procedure. If so, the process 1600 may come to an end, as represented by block 1612. If additional positions or steps in the procedure remained to be program, the process 1600 may proceed back to block 1602, where an additional positioning of the automated suture fixture may be programmed in accordance with blocks 1602 through 1608. In certain embodiments, the storing process represented at block 1608 may not be performed until after all steps of the procedure have been programmed. In certain embodiments, each of the manufacturing steps or positions of the automated suture fixture and/or camera/magnification system may be recorded in sequential order in order to retain such order when playing back the stored procedure. In certain embodiments, where operator-specific metadata is recorded in connection with the process 1600, different operators may be able to store modified versions of the procedure that are specific to the particular operator. That is, an individual operator may be able to train the implant articulation system to his or her desired ergonomics or preferences. Optionally, individual operator information (e.g., profiles) can be applied at a later time to a process script to adjust the script to individual operator characteristics and/or preferences.

In certain embodiments moving from one step of the process 1600 to another or looping back to program a new position at block 1602, may be triggered through the use of a foot pedal, other operator-input triggered device, voice commands, and/or other electronic input.

Figure 17:
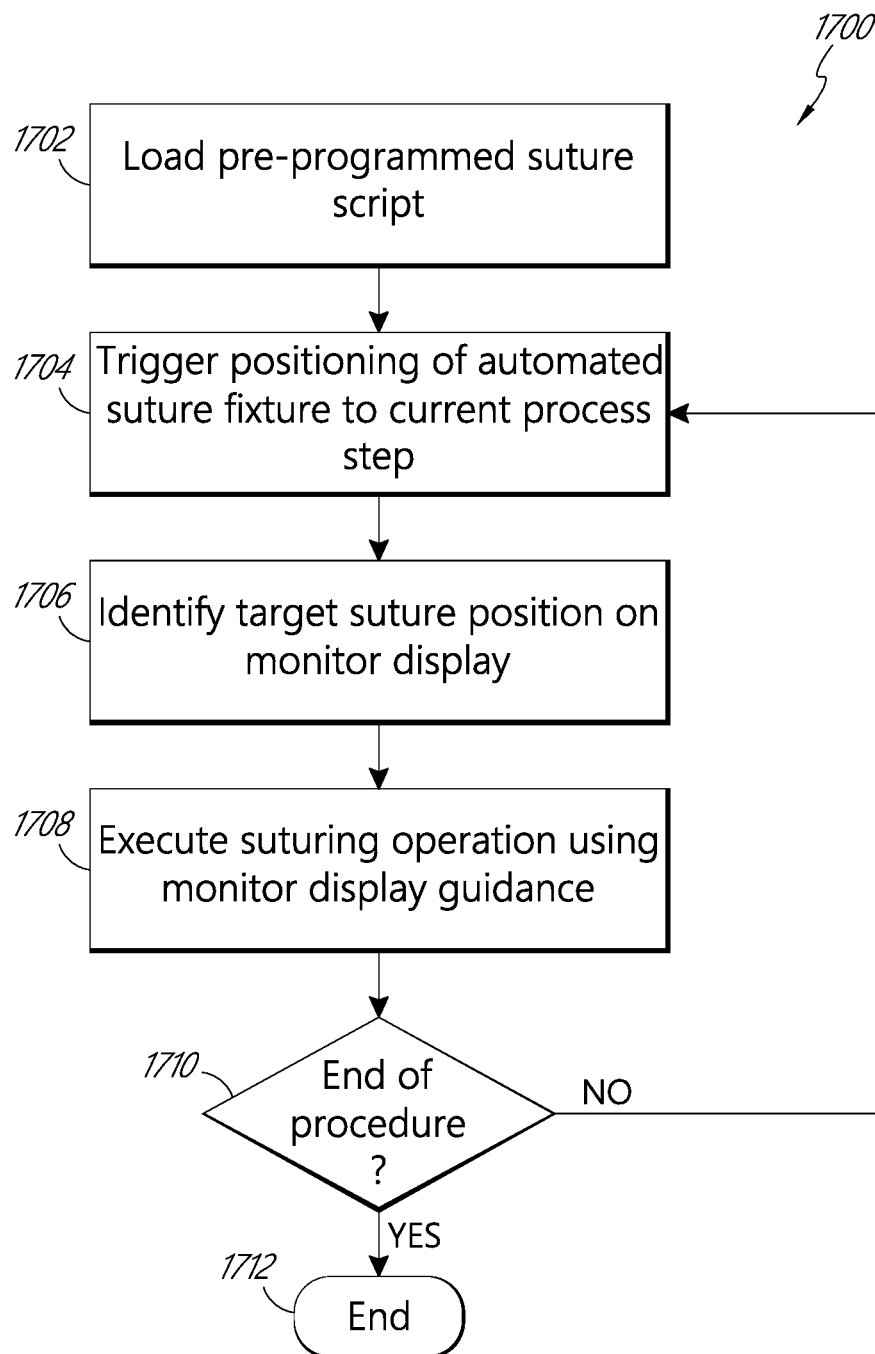
FIG. 17 illustrates a flow diagram illustrating a process for executing a suturing procedure in accordance with one or more embodiments.
Figure 18:
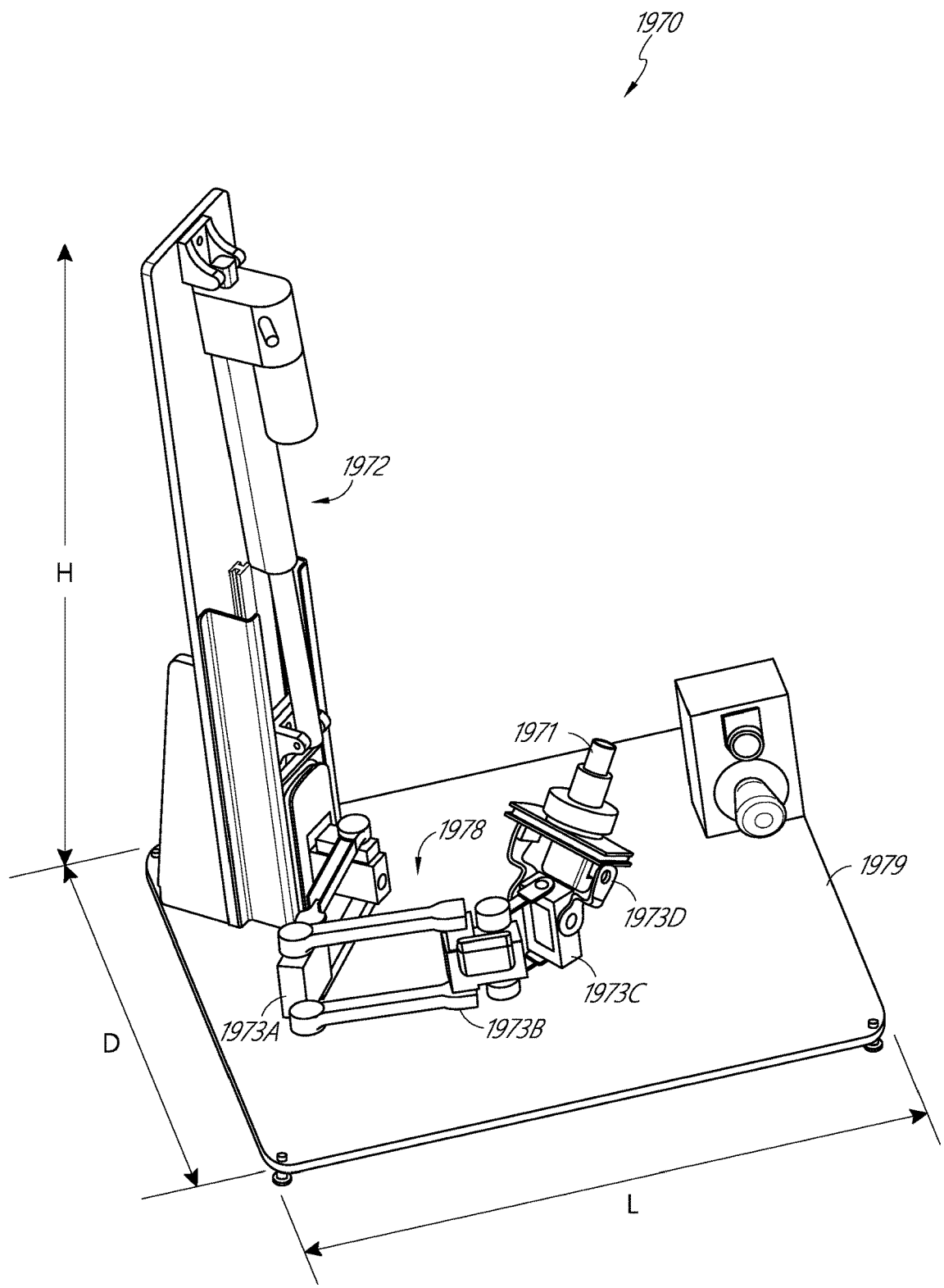
Figure 25:
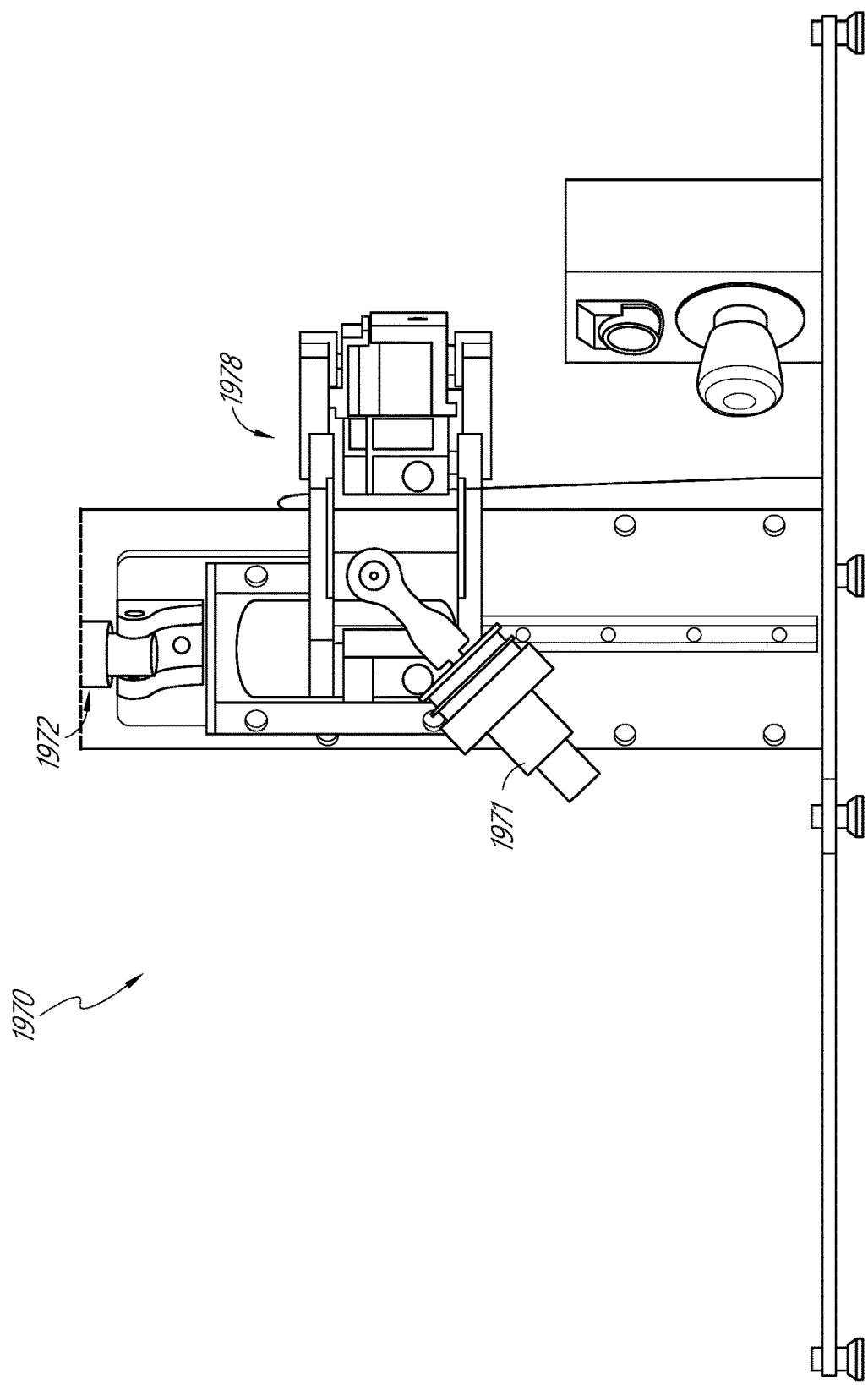

FIG. 17 illustrates a process 1700 for executing a suturing procedure according to one or more embodiments. While described in terms of a suturing procedure, similar steps can be used for other procedures (e.g., for inspection procedures, other treatment or processing procedures, etc.) For example, the process 1700 may be performed after a suture assist system has been preprogrammed with a certain procedure, program, or script, such as can be created using to the training/programming process 1600 described above in connection with FIG. 16. One or more computer components, such as one or more processors and/or memory devices, may be utilized to store and execute a procedure-directing script/program, such that a procedure script/program may be played back for an operator on-demand.

At block 1702, the process may involve loading a preprogrammed suturing process script or program, which may have been previously programmed in connection with the training/programming process as described above. The desired script/program can be loaded in various ways, e.g., by providing input to the system or a computer of the system to load the desired script/program from storage or memory (e.g., stored memory, internal memory, external memory, portable memory, disk, thumb drive, download, etc.), loading the desired script/program from an external source, inputting or providing a code (e.g., scanning a barcode on the target device or materials associated with the target device) such that the system automatically loads the correct script/program for the target device (e.g., based on the input code, scanned barcode, etc.), providing voice commands to load a script/program, and other ways of loading the desired script/program. In certain embodiments, the process 1700 involves selectively loading either a right-handed or left-handed version of the process script based on a preference of the operator or based on an operator profile, or applying operator information to a script to adjust the script to individual operator preferences (e.g., to flip the script positioning for left vs. right handed operators, to adjust positioning for other operator characteristics, for example, size, height, etc.). In certain embodiments, the operator may alternate between right- and left-handed versions as desired, even mid-procedure, which may beneficially allow the operator to rest a fatigued hand, for example. This could be done by applying different information or parameters to the script at different times.

At block 1704, the process involves triggering the positioning of an automated suture fixture (or automated fixture) and/or associated visualization system (e.g., camera or magnification system) to a current process position associated with a current step of the suturing procedure or other procedure. It should be understood that in certain embodiments, performance of step 1704 does not involve positioning, or triggering the positioning of, a visualization system or a camera. For example, an associated camera or other visualization/imaging system can be substantially static, wherein the articulation device controls positioning of the target device at the proper focus or focal length for the visualization/imaging system or camera. The triggering of the automated suture fixture can be input or implemented in a suitable or desirable manner. For example, the operator can activate a foot pedal, other switch, physical trigger button, mechanism, voice command, and/or electronic input (e.g., a touchscreen icon/button, etc.) in order to trigger the set-up of the suture assist system to the next step in the suturing procedure.

At block 1706, the process 1700 can involve identifying a target suture position or other position (e.g., inspection position, other treatment or processing position, etc.) on a monitor display. For example, the target suture position may be identified using one or more visual aids or reticles, or the like, as described above. In addition, identification of the target suture position may be achieved using instructions, or other visual overlays, examples, and/or guidance displayed on the monitor display. The target position can be identified by the operator (e.g., by clicking on a target position, dragging a visual aid to the target position, entering coordinates, or in other ways), and/or the target position can be identified by the script or program automatically to sense and/or indicate where the next step, operation, suture, inspection, etc. should occur.

At block 1708, the process 1700 can involve executing a suturing operation or other operation or step using the monitor display (or other visualization system viewing area) as guidance. For example, the visualization system (e.g., the monitor display, in combination with the operation of an associated camera or magnification system), can present the target suture position in focus, wherein the operator may visually evaluate the suturing position and execution of the operation/step using the monitor display (or other visualization system viewing area).

Once the suturing operation or other operation/step has been executed at block 1708, if the relevant suturing operation or other operation/step represents a final operation/step of the suturing procedure or other procedure, the process 1700 may end as shown at block 1712. However, if additional steps of the suturing operation/procedure or other operation or procedure remain, the process 1700 may return to block 1704, where a subsequent step of the suturing process or other process may be triggered, such that the process 1700 may involve completion of subsequent step(s). In certain embodiments, the process 1700 may involve capturing an image of the suture target prior to the repositioning of the automated suture fixture. For example, image capture may be triggered by user input or other event indicating the completion of a step of the process 1700. Such captured images can be used for a variety of purposes including training and inspection. Optionally, the entire procedure can be recorded (e.g., as a movie file) for training, inspection, quality control, and/or other purposes. Bookmarks or indicators can be stored at times when an operation/step is completed to allow an operator, supervisor, or other person to jump through the video to key times/frames, e.g., for inspection, training, or other purposes. Additionally, the images, video, frames, etc. can be sent/transmitted and graphically displayed on another device (e.g., phone, computer, mobile device, etc.), e.g., sent to a device of a manager and/or quality control person for review.

Where the suture assist system has been programmed to implement, or direct the implementation of, a suturing procedure or other procedure, such procedure may be repeatable over many iterations, thereby providing improved efficiency and completion of procedures (e.g., improved suturing of implant devices).

In certain embodiments, the process 1700 can allow for the operator to make modifications at a given step of the suturing procedure to the positioning of the automated suture fixture and/or camera system in order to further customize such step. In certain embodiments, such altering by the operator can be programmed back into the procedural script executed by the suture assist system in connection with the particular procedure, such that future execution of the procedure can incorporate the modifications implemented by the operator during the process 1700. Furthermore, in certain embodiments, the process 1700 can allow for the operator to temporarily pause the process 1700 prior to completion thereof. For example, the operator may wish to step away from the operating environment, such as for a break or other purpose, wherein the process 1700 can allow for the operator to reinsert him or herself into a stage of the process at which the process was paused. Therefore, such availability of pausing and reentering the process may allow for the operator to reduce strain or burden associated with prolonged engagement with the suture assist system.

Certain suturing procedures (or other procedures) may involve suturing (or other processing, treatment, etc.) of implant devices that have certain requirements with respect to moisture and/or other parameters associated with one or more components of the implant device. For example, with respect to prosthetic heart valves, suturing operations or other operations associated with valve leaflets may require that such leaflets not become dried out, because drying out can adversely affect the physical properties thereof. For example, where the valve leaflets comprise biological material, such as pericardial leaflets, it may be necessary or desirable to periodically expose such leaflets to moisture, such as in the form of a liquid solution, gas, or the like. In certain embodiments, the process 1700, and/or other processes or procedures disclosed herein, can be implemented in connection with a mechanism for allowing the operator or system (e.g., an automated portion of the system) to periodically, or on an as-needed basis, moisturize one or more components of the implant device being sutured. For example, the system can allow the operator to immerse or otherwise saturate or cover at least a portion of the implant device in, for example, glutaraldehyde, or other or liquid. In certain embodiments, an articulation arm in a suture assist system can be configured to implement, as part of an automated procedure, the dipping or immersion, spraying, or other means of exposure, of an implant device or portion thereof in a moisturizing solution. For example, such immersion or other type of moistening of the implant device can be performed substantially automatically and may or may not require engagement by the operator. In certain embodiments, a timer can be implemented in connection with a suturing procedure in accordance with the present disclosure, wherein the timer indicates and/or notifies an operator of moisturizing requirements for an implant device being operated on. For example, with respect to the process 1700 of FIG. 17, an interrupt routine may be implemented which is designed to interrupt the operator and/or the process executed by the suture assist system when it is determined that it is necessary or desirable for the operator to moisturize the implant device or portion thereof. In certain embodiments, sensors, light, lasers, and/or other techniques can be used to detect the moisture level or other characteristics of the target or implant device or leaflets. In certain embodiments, the process 1700 may not continue until the operator has performed the moisturizing step, or alternatively the articulation positioning device that holds the implant device may execute the moisturizing operation in response to the interrupt routine.

Suture Tension Management

Certain embodiments disclosed herein provide for systems, devices and methods for assisting in suturing operations through the use of tensioning functionality, which may be useful with respect to improvement in quality, efficiency, and/or quality control evaluation. For example, where suturing involves the puncturing of a needle through one or more layers of material of an implant device, varying pinch forces may be required in order to penetrate the layers with the proper amount of tension. Certain systems involve the use of an automated suture fixture that is designed to present to the operator varying tension settings in one or more stages of the articulation device, such as at an articulation arm or at a base of the automated suture fixture. The tension management of the system may promote consistent force of needles and puncturing certain materials of the implant device, and can be used in combination with an automated needle delivery system, to thereby improve the tensioning execution by the automated needle delivery system.

In certain embodiments, tension management can be implemented through the use of a pressure-sensitive pressure plate, device, or structure, which can be disposed on or in physical contact with a base portion of the automated suture fixture, or other portion of the automated suture fixture. The pressure sensitive device can be configured to provide a readout of tensions experienced by the automated suture fixture, which may indicate whether the operator has exacted excessive torque or pressure on the implant device, or not enough force, which may provide an indication of quality of operator performance.

Articulation and/or tensioning of the articulation arm may be designed to present a desired sewing angle or sewing tension and/or resistance for a specific stitch. Tensioning of the articulation arm or other component of the automated suture fixture may provide controlled pinch forces for penetrating, for example, heart valve implant device leaflets. Tension management may be used to provide consistent force for needle delivery, wherein tighter tension may be desirable for certain punctures, while looser tension may be desirable or others.

Fully Automated System

In certain embodiments, a fully or mostly automated system can be used. The fully or mostly automated system could include one or multiple automated fixtures (e.g., one, two, three, four, five, six, or more than six automated fixtures). For example, a first automated fixture (which can be the same as or similar to the automated fixtures or automated suture fixtures described and shown herein) could be used to articulate and move an implant device to various desired positions for processing operations/step (e.g., suturing, treatment, applications, etc.), while a second and/or third automated fixture or device could be used to perform the processing operations/steps at the various desired positions. For example, a second automated fixture could act similar to a sewing machine that moves a needle in and out (e.g., which can be done in a single plane, along a linear path, in three-dimensional space, etc.) to add the sutures to a target or implant device while the first automated fixture moves the target or implant device to the correct position to receive the desired suture in the correct location on the target or implant device. A second automated fixture and a third automated fixture could work together to move and receive a needle in a sewing operation, e.g., passing the needle from the second fixture to the third fixture and from the third fixture to the second fixture after passing the needle through the desired portion of a target device held and moved to the desired positions by the first fixture, etc. Suture tensioning management could also be used, which could, for example be similar to that described above to maintain and use proper tensioning. Optionally, the second automated fixture (or an additional third automated fixture) could be configured and used to apply another material (e.g., a polymer, coating, or other material) to the target or implant device (e.g., the full device or a portion thereof) without suturing, e.g., in a sputtering procedure, electrospinning procedure, treatment procedure, coating procedure, and/or other procedure.

The automated system desirably is programmable such that multiple fixtures can be coordinated with each other to follow or implement a previously specified or programmed operation on a target device (e.g., a previous specified or programmed sewing pattern for a heart valve).

Multi-Tool Assistance

Certain embodiments disclosed herein provide for systems, devices, and methods for assisting in suturing procedures or other procedures, wherein an automated fixture or automated suture fixture and/or other system components are utilized in order to allow for execution of suturing operations or other operations by an operator using a single hand to operate, for example, a needle. In other words, in certain embodiments, the assist systems described herein may replace (or be used instead of) one of the operator's hands, thereby allowing the operator to perform operations or sutures with only one hand. Where only a single hand is required for executing suturing operations or other operations, systems, devices, and methods disclosed herein may allow for additional operations and functions to be performed by the operator using a free hand not required for holding the target or implant device being sutured or processed or operated on, which can advantageously instead be held by an articulation arm of the automated suture fixture, as described herein. For example, the free hand of the operator may be utilized for pre-drilling, pre-punching, or pre-dimpling of fabric or material, or the like, which may be executed using any suitable or desirable tool for such purposes, such as a mechanical tool, laser, or the like.

Furthermore, the free hand of the operator can be used for tensioning control or other operations. The free hand of the operator can be utilized to operate any type of hand tool, such as hand tools requiring only a simple trigger pull, for example. For example, a pistol-grip punch tool can be used by the operator with the operator's freehand. With the operator's free hand being used for other suture-related activities, stitch quality can be improved, and the precision of various operations of a suturing procedure can be improved.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

While many of the specific examples and embodiments described herein focus on suturing assist systems, automated suture fixtures, suturing operations/steps/procedures, etc. the invention is not limited to suturing applications and the same or similar systems, fixtures, devices, features, components, principles, operations/steps/procedures, etc. to those discussed with respect to suturing can be used for other operations/steps/procedures/treatments, etc. For example, the system may be used to apply material to a frame using sputtering, electrospinning, rivets, staples, fasteners, fastener guns, clamps, or in other ways without involving suturing. While much of the discussion focuses on implant devices (e.g., human prosthetic heart valve implants) or other specific examples, the same or similar systems, fixtures, devices, features, components, principles, operations/steps/procedures, etc. to those discussed with respect to the examples above can be applied to other types of target devices.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments do include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Components, aspects, features, etc. of the systems, assemblies, devices, apparatuses, methods, etc. described herein may be implemented in hardware, software, or a combination of both. Where components, aspects, features, etc. of the systems, assemblies, devices, apparatuses, methods, etc. described herein are implemented in software, the software may be stored in an executable format on one or more non-transitory machine-readable mediums. Further, the software and related steps of the methods described above may be implemented in software as a set of data and instructions. A machine-readable medium includes any mechanism that provides (e.g., stores and/or transports) information in a form readable by a machine (e.g., a computer). For example, a machine-readable medium includes read only memory (ROM); random access memory (RAM); magnetic disk storage media; optical storage media; flash memory devices; DVD's, electrical, optical, acoustical or other forms of propagated signals (e.g., carrier waves, infrared signals, digital signals, EPROMs, EEPROMs, FLASH, magnetic or optical cards, or any type of media suitable for storing electronic instructions. Information representing the units, systems, and/or methods stored on the machine-readable medium may be used in the process of creating the units, systems, and/or methods described herein. Hardware used to implement the invention may include integrated circuits, microprocessors, FPGAs, digital signal controllers, stream processors, and/or other components.

What is claimed is:

1. A suturing assistance system comprising:
   an automated suture fixture comprising a plurality of motorized actuator devices and a suture target holder, the automated suture fixture being configured to rotate a target suture device mounted to the holder;
   a camera system configured to generate an enlarged image of the target suture device; and a suture target display configured to display the enlarged image, the suture target display indicating a target suture position associated with the target suture device.

2. The suturing assistance system of claim 1, wherein the target suture device is a heart valve.

3. The suturing assistance system of claim 1, further comprising a controller configured to direct the camera system to capture image data associated with a suturing procedure and store the image data with metadata identifying at least one of the suturing procedure and an operator associated with the suturing procedure.

4. The suturing assistance system of claim 1, wherein the automated suture fixture is configured to adjust a tension of the automated suture fixture.

5. The suturing assistance system of claim 1, wherein the automated suture fixture includes a pressure plate component configured to adjust a tension of the automated suture fixture.

6. The suturing assistance system of claim 1, wherein the suture target display comprises a reticle.

7. The suturing assistance system of claim 6, wherein the reticle comprises crosshairs.

8. The suturing assistance system of claim 6, wherein the reticle comprises a circular reticle.

9. The suturing assistance system of claim 8, wherein the circular reticle includes notches for stitch counting.

10. The suturing assistance system of claim 1, wherein the target suture device holder is a gimbal holder assembly.

11. The suturing assistance system of claim 10, wherein the gimbal holder assembly comprises a three-axis gimbal.

12. The suturing assistance system of claim 1, wherein the automated suture fixture is configured to move the target suture device in at least four directions.

13. The suturing assistance system of claim 1, wherein the automated suture fixture comprises a plurality of servo motor devices daisy-chained together.

14. The suturing assistance system of claim 1, wherein the camera system comprises a first camera and a second camera, the first and second cameras collectively configured to provide images of two different views of the target suture device.

15. The suturing device of claim 1, wherein the automated suture fixture comprises an encoder associated with an articulation arm, the encoder configured to provide position information for the articulation arm.

16. An automated suture fixture comprising:
a plurality of motorized actuator devices, each comprising a motor and a rotating support member coupled to a rotor component of the motor; and
a suture target holder assembly attached to the rotating support member of a distal actuator device of the plurality of motorized actuator devices and configured to hold a prosthetic heart valve device;
wherein each of the plurality of motorized actuator devices is fixed to one or more other motorized actuator devices of the plurality of motorized actuator devices; and
wherein the automated suture fixture is configured to receive control signals and rotate the rotating support members of one or more of the plurality of motorized actuator devices based on the control signals.

17. The automated suture fixture of claim 16, wherein each of the plurality of motorized actuator devices further comprises a servo feedback component configured to generate a signal indicating a position of a respective rotor component.

18. The automated suture fixture of claim 16, wherein the plurality of motorized actuator devices comprises one or more base actuator devices and at least one intermediate-stage actuator device fixed at a base thereof to the rotating support members of the one or more base actuator devices, wherein the distal actuator device is fixed at a base thereof to the rotating support member of the intermediate-stage actuator device.

19. The automated suture fixture of claim 18, wherein the base of the intermediate-stage actuator device is fixed to the rotating support members of the one or more base actuator devices via a connector plate mounted to the rotating support members of the one or more base actuator devices.

20. The automated suture fixture of claim 19, wherein the suture target holder assembly comprises one or more components configured to rotate about an axis substantially tangent to an axis of rotation of the rotating support member of the distal actuator device.

* * * * *